(12) United States Patent
Lee

(10) Patent No.: US 10,232,050 B1
(45) Date of Patent: Mar. 19, 2019

(54) MULTI-FUNCTIONAL PARTICLES AND METHODS OF USING THE SAME

(71) Applicant: Clemson University, Anderson, SC (US)

(72) Inventor: Jeoung Soo Lee, Clemson, SC (US)

(73) Assignee: Clemson University, Clemson, SC (US)

( * ) Notice: Subject to any disclaimer, the term of this patent is extended or adjusted under 35 U.S.C. 154(b) by 138 days.

(21) Appl. No.: 14/966,614

(22) Filed: Dec. 11, 2015

Related U.S. Application Data

(60) Provisional application No. 62/091,190, filed on Dec. 12, 2014.

(51) Int. Cl.

| *A61K 48/00* | (2006.01) |
|---|---|
| *A61K 31/337* | (2006.01) |
| *A61K 47/48* | (2006.01) |
| *A61K 31/713* | (2006.01) |
| *A61K 31/4015* | (2006.01) |
| *C07K 16/28* | (2006.01) |

(52) U.S. Cl.
CPC ........ *A61K 47/488* (2013.01); *A61K 31/4015* (2013.01); *A61K 31/713* (2013.01); *A61K 47/482* (2013.01); *A61K 47/48561* (2013.01); *C07K 16/286* (2013.01)

(58) Field of Classification Search
CPC .............. A61L 2300/416; A61L 29/085; A61L 2300/62; A61L 29/16; C08L 2666/20; C08L 79/02; C08L 77/02; C08L 77/06; A61K 9/0019; A61K 31/337; A61K 47/34; A61K 47/48192; A61K 48/0041; A61K 9/08
USPC .......... 514/44 R, 1.1, 44 A, 449, 772.3, 788; 424/450, 488, 489
See application file for complete search history.

(56) References Cited

U.S. PATENT DOCUMENTS

| 4,501,729 | A | 2/1985 | Boucher et al. |
|---|---|---|---|
| 6,410,057 | B1 | 6/2002 | Kweon-Choi et al. |
| 6,569,528 | B2 | 5/2003 | Nam et al. |
| 7,018,655 | B2 | 3/2006 | Lele et al. |
| 7,060,498 | B1 | 6/2006 | Wang |
| 7,371,781 | B2 | 5/2008 | Bae et al. |
| 7,507,859 | B2 | 3/2009 | Grinstaff et al. |
| 7,534,449 | B2 | 5/2009 | Saltzman et al. |
| 8,128,959 | B2 | 3/2012 | Maeda et al. |
| 8,173,167 | B2 | 5/2012 | Kwon et al. |
| 8,263,664 | B2 | 9/2012 | Kim et al. |
| 8,263,665 | B2 | 9/2012 | Sill et al. |
| 8,299,178 | B2 | 10/2012 | Hsiue et al. |
| 8,349,306 | B2 | 1/2013 | Seo et al. |
| 8,349,991 | B2 | 1/2013 | Colton et al. |
| 8,519,051 | B2 | 8/2013 | Bobe et al. |
| 8,545,830 | B2 | 10/2013 | Lowe et al. |
| 2008/0260725 | A1 | 10/2008 | Naik et al. |
| 2009/0136583 | A1 | 5/2009 | Park et al. |
| 2011/0223669 | A1 | 9/2011 | Yamanaka et al. |
| 2011/0237686 | A1 | 9/2011 | Ng et al. |
| 2016/0184443 | A1* | 6/2016 | Lu ............... A61K 47/48192 514/44 R |

FOREIGN PATENT DOCUMENTS

| CN | 20111439336 | 12/2011 |
|---|---|---|
| WO | WO 2011/119995 A2 | 9/2011 |
| WO | WO 2013/135360 A1 | 9/2013 |

OTHER PUBLICATIONS

Lee et al. (Clemson University, Bioengineering Department, (1 page) (2010).*
Lee e tal. Macromolecular Research, 19(7): 688-693 (2010).*
Lee et al. (Clemson University, Bioengineering Department, (1 page) (2010), obtained from the following URL: http://abstracts.biomaterials.org/data/papers/2010/917.pdf.*
Abdallah et al. "A Powerful Nonviral Vector for In Vivo Gene Transfer into the Adult Mammalian Brain: Polyethylenimine" *Human Gene Therapy* 7:1947-1954 (1996).
Abdanipour et al. "Intraspinal transplantation of motoneuron-like cell combined with delivery of polymer-based glial cell line-derived neurotrophic factor for repair of spinal cord contusion injury" *Neural Regeneration Research* 9(10):1003-1013 (2014).
Bauknight et al. "Convection enhanced drug delivery of BDNF through a microcannula in a rodent model to strengthen connectivity of a peripheral motor nerve bridge model to bypass spinal cord injury" *Journal of Clinical Neuroscience* 19(4):563-569 (2012) (Abstract only).
Blits et al. "Direct Gene Therapy for Repair of the Spinal Cord" *Journal of Neurotrauma* 23(3/4):508-520 (2006).
Boussif et al. "A versatile vector for gene and oligonucleotide transfer into cells in culture and in vivo: Polyethylenimine" *Proceedings of the National Academy of Sciences USA* 92(16):7297-7301 (1995).
Gonda, I. "Aerosols for delivery of therapeutic and diagnostic agents to the respiratory tract" *Critical Reviews in Therapeutic Drug Carrier Systems* 6(4):273-313 (1990) (Abstract Only).
Green et al. "Polymeric Micelle as a Delivery Carrier for Brain Tumor" *Bioengineering Dept. 4D Lab, Clemson University* (1 page) (2015).
Guerra-Crespo et al. "Polyethylenimine improves the transfection efficiency of primary cultures of post-mitotic rat fetal hypothalamic neurons" *Journal of Neuroscience Methods* 127(2):179-192 (2003) (Abstract only).
Guo et al. "Nanoparticles Escaping RES and Endosome: Challenges for siRNA Delivery for Cancer Therapy" *Journal of Nanomaterials* 2011:1-12 (2011) (Abstract only).
Gwak et al. "Development of polymeric micelle as a combinatorial delivery system for central nervous regeneration" *Department of Bioengineering, Clemson University* (1 page) (2015).

(Continued)

*Primary Examiner* — Janet L Epps-Smith
(74) *Attorney, Agent, or Firm* — Myers Bigel, P.A.

(57) ABSTRACT

Provided herein are multi-functional particles. The particles may include poly(lactide-co-glycolide)-g-polyethylenimine (PLGA-g-PEI (PgP)), at least one targeting moiety, at least one therapeutic agent, and/or at least one nucleic acid. Also provided herein are methods of using the multi-functional particles.

41 Claims, 33 Drawing Sheets

(56) References Cited

OTHER PUBLICATIONS

Gwak et al. "Cationic, amphiphilic copolymer micelles as nucleic acid carriers for enhanced transfection in rat spinal cord" *Acta Biomaterialia* 35:98-108 (2016).
Gwak et al. "Polymeric micelle as therapeutic RhoA siRNA carrier for axonal regeneration in spinal cord injury" *Department of Bioengineering, Clemson University* (1 page) (2016).
Heidemann et al. "The culture of chick forebrain neurons" *Methods in Cell Biology* 71:51-65 (2003) (Abstract only).
Jeon et al. "Synthesis and Characterization of Polyethylenimine-Graft-Poly (L-Lactide-Co-Glycolide) Block Copolymers for Gene Delivery" *Key Engineering Materials* 342-343: pp. 521-524 (2007) (Abstract only).
Kabanov et al. "Pluronic block copolymers as novel polymer therapeutics for drug and gene delivery" *Journal of Controlled Release* 82(2-3):189-212 (2002) (Abstract only).
Kabanov et al. "Pluronic block copolymers: novel functional molecules for gene therapy" *Advanced Drug Delivery Reviews* 54(2):223-233 (2002) (Abstract only).
Kataoka et al. "Block copolymer micelles for drug delivery: design, characterization and biological significance" *Advanced Drug Delivery Reviews* 47(1):113-131 (2001) (Abstract only).
Kim et al. "Physicochemical characterization of poly(L-lactic acid) and poly(D,L-lactide-co-glycolide) nanoparticles with polyethylenimine as gene delivery carrier" *International Journal of Pharmaceutics* 298:255-262 (2005).
Kim et al. "Enhanced transfection of primary cortical cultures using arginine-grafted PAMAM dendrimer, PAMAM-Arg" *Journal of Controlled Release* 114(1):110-117 (2006) (Abstract only).
Kwon et al. "Soluble Self-Assembled Block Copolymers for Drug Delivery" *Pharmaceutical Research* 16(5):597-600 (1999).
Lee et al. "Neuron-specific Polymeric Micelle Nanotherapeutics for CNS Regeneration" *Clemson University, Bioengineering Department* (1 page) (2010).
Lee et al. "Polyethylenimine-g-Poly(lactic-co-glycolic acid) as Non-Toxic Micelle-Type Carrier for Gene Delivery" *Macromolecular Research* 19(7):688-693 (2011).
Li et al. "Stealth nanoparticles: high density but sheddable PEG is a key for tumor targeting" *Journal of Controlled Release* 145(3):178-181 (2010).
Macks et al. "Combinatorial Therapy of Rolipram and pNGF for Traumatic Brain Injury" *Department of Bioengineering 4D Lab, Clemson University* (1 page) (2015).
Macks et al. "Polymeric micelle delivery system for combinatorial therapy after traumatic brain injury" *Drug Design, Development, and Delivery (4D) Laboratory, Department of Bioengineering, Clemson University* (20 pages) (2016).
Mishra et al. "Reconstitutable Charged Polymeric $(PLGA)_2$-b-PEI Micelles for Gene Therapeutics Delivery" *Biomaterials* 32(15):3845-3854 (2011).
Nice et al. "Polymeric Micelle Delivery System for Neural Regeneration" *Bioengineering Dept. 4D Lab, Clemson University* (1 page) (2010).
Ohki et al "Improving the transfection efficiency of post-mitotic neurons" *Journal of Neuroscience Methods* 112(2):95-99 (2001) (Abstract only).
Osada et al. "Polymeric micelles from poly(ethylene glycol)-poly(amino acid) block copolymer for drug and gene delivery" *Journal of the Royal Society Interface* 6:S325-S339 (2009).
Owen et al. "Polymeric micelle stability" *Nano Today* 7(1):53-65 (2012) (Abstract only).
Raeburn et al. "Techniques for drug delivery to the airways, and the assessment of lung function in animal models" *Journal of Pharmacological and Toxicological Methods* 27:143-159 (1992) (Abstract only).
Poulsen et al. "Gene therapy for spinal cord injury and disease" *Journal of Spinal Cord Medicine* 25(1):2-9 (2002) (Abstract only).
Temples et al. "Folate-mediated Polymeric Micelle Delivery System for Drug Resistant Cancer" *4D Lab, Bioengineering Dept. Clemson University* (1 page) (2014), Jun. 26, 2017.
Temples et al. "Multi-functional Polymeric Micelle Delivery System for Drug Resistant Cancer Treatment" *Bioengineering Dept. 4D Lab, Clemson University* (1 page) (2014).
Temples et al. "Folate-functionalized Polymeric Micelle for Combinatorial Therapy to Overcome Drug Resistant Breast Cancer" *Drug Design, Development and Delivery Laboratory, Department of Bioengineering, Clemson University* (1 page) (2015).
Thomas et al. "Enhancing polyethylenimine's delivery of plasmid DNA into mammalian cells" *Proceedings of the National Academy of Sciences USA* 99(23):14640-14645 (2002).
Tyle, Praveen "Iontophoretic Devices for Drug Delivery" *Pharmaceutical Research* 3(6):318-326 (1986).
Wang et al. "Polymer-DNA Hybrid Nanoparticles Based on Folate-Polyethylenimine-block-poly(L-lactide)" *Bioconjugate Chemistry* 16 391-396 (2005).
Zhang et al. "Neuron-specific Polymeric Micelle as a siRNA Delivery Carrier for CNS Regeneration" *Bioengineering Department, Clemson University* (1 page) (2011).

* cited by examiner

* P<0.05 compared to control
# P<0.05 compared to PEI and Naked
## P<0.05 compared to N/P ratio 5

*P<0.05 compared to untreated
P<0.05 compared to PgP i) 2 hrs   ii) 4 hrs   iii) 6 hrs
iv) 24 hrs   v) 72 hrs   vi) 120 hrs i) 2 hrs   ii) 6 hrs
iii) 1 day   iv) 3 days
v) 5 days   vi) 5 days (Photo)

MULTI-FUNCTIONAL PARTICLES AND METHODS OF USING THE SAME

RELATED APPLICATION INFORMATION

This application claims the benefit of and priority to U.S. Provisional Application Ser. No. 62/091,190, filed Dec. 12, 2014, the disclosure of which is hereby incorporated by reference herein in its entirety.

STATEMENT OF GOVERNMENT SUPPORT

This invention was made with government support under Grant Nos. P20GM103444 and 5P20GM103444-07 awarded by National Institutes of Health. The government has certain rights in the invention.

FIELD OF THE INVENTION

The present invention is directed to multi-functional particles and methods of using the same.

BACKGROUND

Spinal cord injury (SCI) damages ascending and descending axons that are unable to regenerate and re-establish functional connections with their targets. In addition to paralysis and loss of sensory function below the level of the lesion, SCI may also lead to chronic pain, spasticity, respiratory impairment, loss of bowel or bladder control, and sexual dysfunction. Currently, there is no clinically effective therapy available. In addition, therapeutic strategies are needed to treat cancer.

Gene therapy involves the intracellular delivery of a vector containing genetic material capable of expressing a therapeutic gene. Delivery of therapeutics and/or nucleic acids capable of changing gene expression levels may be desirable.

SUMMARY OF THE INVENTION

A first aspect of the present invention is a particle comprising poly(lactide-co-glycolide)-g-polyethylenimine (PLGA-g-PEI (PgP)). The particle may include at least one targeting moiety, at least one therapeutic agent, and/or at least one nucleic acid. In some embodiments, the PgP particle includes at least one targeting moiety, at least one therapeutic agent, and at least one nucleic acid.

Another aspect of the present invention includes a method of delivering at least one therapeutic agent and/or at least one nucleic acid to a target. The method may include administering a particle of the present invention to the target, thereby delivering the at least one therapeutic agent and/or the at least one nucleic acid to the target.

A further aspect of the present invention includes a method of promoting axonal regeneration and/or treating a central nervous system (CNS) injury in a subject, the method including administering a particle of the present invention to the subject, thereby promoting axonal regeneration and/or treating a CNS injury in the subject.

Another aspect of the present invention includes a method of treating cancer in a subject, the method including administering a particle of the present invention to the subject, thereby treating cancer in the subject. In some embodiments, the cancer is breast cancer. In some embodiments, the cancer is brain cancer.

A further aspect of the present invention includes a method of increasing the therapeutic efficiency of a therapeutic agent and/or nucleic acid in a subject, the method including administering a particle of the present invention to the subject, thereby increasing the therapeutic efficiency of the therapeutic agent and/or nucleic acid in the subject. In some embodiments, the systemic side effects associated with administering the particle are reduced compared to a conventional therapy administering the at least one therapeutic agent and/or at least one nucleic acid.

DETAILED DESCRIPTION OF EMBODIMENTS

Figure 1:
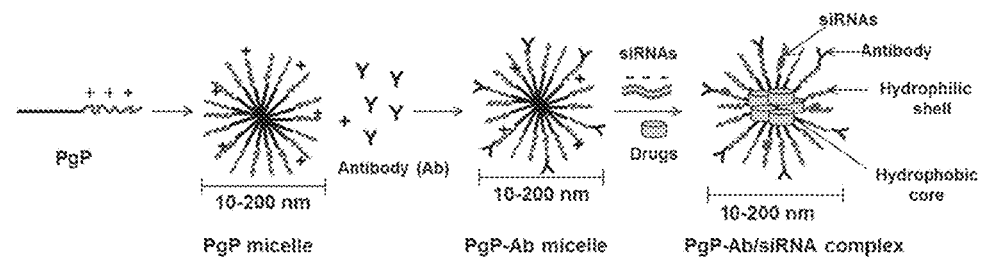
FIG. 1 shows a schematic of an example particle and method of making the same according to an embodiment of the present invention.

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value such as an amount or concentration and the like, is meant to encompass variations of ±10%, ±5 %, ±1%, ±0.5%, or even ±0.1% of the specified value as well as the specified value. For example, "about X" where X is the measurable value, is meant to include X as well as variations of ±10%, +5%, ±1%, ±0.5%, or even ±0.1% of X. A range provided herein for a measurable value may include any other range and/or individual value therein.

According to some embodiments of the present invention, provided herein are multi-functional particles and methods of using the same. The particles may comprise an amphiphilic graft copolymer, such as, for example, poly(lactide-co-glycolide)-g-polyethylenimine (PLGA-g-PEI (PgP)). A multi-functional particle of the present invention may comprise at least one targeting moiety, at least one therapeutic agent, and/or at least one nucleic acid. Thus, a particle of the present invention may be specific for and/or directed to a particular target, may deliver a therapeutic agent, and/or may deliver a nucleic acid, such as, for example, a therapeutic nucleic acid. In some embodiments, a particle may comprise PLGA-g-PEI, at least one targeting moiety, at least one therapeutic agent, and at least one nucleic acid. In some embodiments, the particle may provide for the simultaneous delivery of a therapeutic agent and/or a nucleic acid to a target (e.g., a cell and/or tissue), optionally in a subject.

Some embodiments include that a particle of the present invention has low cytotoxicity to a cell and/or tissue. In some embodiments, a particle of the present invention may have a cytotoxicity of less than about 70%, such as, for example, less than about 65%, 60%, 55%, 50%, 45%, 40%, 35%, 30%, 25%, 20%, 15%, 10%, or 5%. Cytotoxicity may be determined using methods known to those of skill in the art, such as, for example, by using a MTT assay. In some embodiments, the particle may be non-toxic to the subject, tissue, and/or cell to which it is delivered.

In some embodiments, a particle of the present invention may comprise a shell having an interior surface and an exterior surface. In some embodiments, at least a portion of the interior surface of the shell is hydrophobic and at least a portion of the exterior surface of the shell is hydrophilic. The particle may comprise a core. The core of the particle may be formed from the interior surface of the shell. Thus, a particle of the present invention may have a hydrophobic core and a hydrophilic exterior surface. In some embodiments, the exterior surface of the shell comprises a plurality of primary amines.

In some embodiments, an amphiphilic graft copolymer (e.g., PLGA-g-PEI (PgP)) forms the particle structure and/or the shell of the particle. In some embodiments, the hydrophobic portion of the amphiphilic graft copolymer makes up the interior of the particle and the hydrophilic portion of the amphiphilic graft copolymer makes up the exterior of the particle.

Some embodiments include that the particle comprises PLGA-g-PEI and at least a portion of PLGA of the PLGA-g-PEI forms at least a portion of the interior of the particle (e.g., an interior surface of the shell and/or the core) and at least a portion of PEI of the PLGA-g-PEI forms at least a portion of the exterior of the particle (e.g., an exterior surface of the shell).

The particle may comprise a targeting moiety, such as, for example, 1, 2, 3, 4, 5, 6, 7, 8, 9, 10, 20, 30, 40, 50, 100, or more targeting moieties. When two or more targeting moieties are present, they may be the same as and/or different than another targeting moiety. In some embodiments the particle comprises a plurality of targeting moieties that may be the same and/or different from one another. The one or more targeting moieties may be present on and/or in the particle in any suitable concentration or amount. In some embodiments, the one or more targeting moieties may be present on and/or in the particle in an amount or concentration sufficient to direct and/or target the particle to a desired target, such as, for example, a cell and/or tissue. In some embodiments, the targeting moiety comprises at least one cell and/or tissue-specific targeting moiety, such as, for example, a targeting moiety specific for a central nervous system tissue (e.g., spinal cord, brain, etc.), neuron, cancerous tissue and/or cell, muscle tissue, etc. Example targeting moieties include, but are not limited to, proteins (including cell adhesion molecules such as, e.g., L1 and other neural cell adhesion molecules, antibodies and/or fragments thereof that recognize target antigens such as, e.g., protein tyrosine phosphatase sigma receptor, Nogo receptor (NgR1), human epidermal growth factor receptor (Her2), and estrogen receptor), hormones, peptides, nucleic acids (e.g., aptamers), and/or small molecules (e.g., glucose, sugar, folic acid, and transferrin).

In some embodiments, the targeting moiety is attached to a portion of the exterior of the particle (e.g., an exterior surface of the shell). Some embodiments include that the targeting moiety is covalently conjugated to the particle. In some embodiments, the targeting moiety is covalently conjugated to a portion of PEI of PLGA-g-PEI. In some embodiments, the exterior of the particle comprises a primary amine and the targeting moiety is covalently conjugated to the primary amine.

The particle may comprise one or more therapeutic agent(s), such as, for example, 1, 2, 3, 4, 5 or more different therapeutic agent(s). In some embodiments, the core of the particle comprises the one or more therapeutic agent(s). In some embodiments, the one or more therapeutic agent(s) comprise a hydrophobic therapeutic agent. The one or more therapeutic agent(s) may be present in and/or on the particle in any suitable concentration or amount. In some embodiments, the one or more therapeutic agent(s) are present in a therapeutically effective amount. As used herein, the term "therapeutically effective amount" refers to an amount of a therapeutic agent and/or nucleic acid that elicits a therapeutically useful response in a subject. Those skilled in the art will appreciate that the therapeutic effects need not be complete or curative, as long as some benefit is provided to the subject. Example therapeutic agents include, but are not limited to, a phosphodieserase inhibitor (e.g., Rolipram, Ibudilast, and Piclamilast), doxorubicin, temozolomide (TMZ), vincristine, oxaliplatin, doxetacel, and/or paclitaxel.

The particle may comprise a nucleic acid, such as, for example, 1, 2, 3, 4, 5, 6, 7, 8, 9, 10, 20, 30, 40, 50, 100, or more nucleic acids. When two or more nucleic acids are present, they may be the same as and/or different than another nucleic acid. In some embodiments, the particle comprises a plurality of nucleic acids that may be the same and/or different from one another. The nucleic acid may be present in and/or on the particle in any suitable concentration or amount. In some embodiments, the nucleic acid may be present in a therapeutically effective amount. In some embodiments, the nucleic acid may comprise a therapeutic gene (e.g., pDNA), antisense oligonucleotides (ODN), and/or small interfering RNA (siRNA). Example nucleic acids include, but are not limited to, RhoA siRNAs, PKC siRNAs, EGFR siRNAs, PTP sigma, RPN2 siRNAs, O-6-methlygunaine-DNA methyl transferase (MGMT) siRNAs, and/or P-glycoprotein (multidrug resistant gene:MDR1) siRNAs.

In some embodiments, the nucleic acid is attached to a portion of the exterior of the particle (e.g., an exterior surface of the shell). Some embodiments include that the nucleic acid is electrostatically bound to a portion of the exterior of the particle. In some embodiments, the nucleic acid is electrostatically bound to a portion of PEI of PLGA-g-PEI.

In some embodiments, the particle is a polymeric micelle. As shown in FIG. 1, in some embodiments, a polymer (e.g., PLGA-g-PEI (PgP)) as described herein may be used to form a particle (e.g., a PgP micelle) of the present invention. The particle may spontaneously self-assemble in an aqueous solution to form a micelle. In some embodiments, a targeting moiety (e.g. an antibody, protein, peptide, sugar, folic acid), at least one therapeutic agent (e.g., drug), and/or at least one nucleic acid (e.g., pDNA, ODN, siRNA) may be added and/or attached to the particle as shown in FIG. 1. As shown in FIG. 1, the particle comprises PLGA-g-PEI and at least a portion of PLGA of the PLGA-g-PEI forms at least a portion of the interior of the particle (e.g., an interior surface of the shell and/or the core) and at least a portion of PEI of the PLGA-g-PEI forms at least a portion of the exterior of the particle (e.g., an exterior surface of the shell). Thus, a particle of the present invention may comprise a micelle that has an interior core and a shell having an exterior surface.

In some embodiments, at least a portion of the interior core is hydrophobic and at least a portion of the exterior surface of the shell is hydrophilic. In some embodiments, PLGA-g-PEI may form the micelle, and at least a portion of PLGA of PLGA-g-PEI may form at least a portion of the core of the micelle and at least a portion of PEI of PLGA-g-PEI may form at least a portion of the exterior surface of the shell of the micelle. In some embodiments, the exterior surface of the shell may be positively charged. A targeting moiety may be covalently conjugated to a portion of the exterior surface of the shell and/or a nucleic acid may be electrostatically bound to a portion of the exterior surface of the shell (e.g., to the positively charged exterior surface of the shell).

Some embodiments include that the particle is a nanoparticle. The particle may have any suitable diameter. In some embodiments, the particle may have a diameter in a range of about 1 nm to about 500 nm, such as, for example, in a range of about 10 nm to about 200 nm, about 100 nm to about 500 nm, about 10 nm to about 100 nm, about 1 nm to about 50 nm, or about 50 nm to about 150 nm. In some embodiments, the particle may have a diameter of about 1, 5, 10, 15, 20, 30, 40, 50, 60, 70, 80, 90, 100, 125, 150, 175, 200, 225, 250, 275, 300, 325, 350, 375, 400, 425, 450, 475, 500 nm or more. In some embodiments, a particle may have a diameter of less than about 200 nm.

The particle may have a uniform size and/or shape. In some embodiments, the size and/or shape of the particle may change and/or vary by less than about ±20% (e.g., less than about +15%, 10%, 5%, or 1%). In some embodiments, the diameter of the particle may change and/or vary in size and shape by less than about ±20% (e.g., less than about ±15%, 10%, 5%, or 1%). Size, shape, and/or diameter may be measured by methods known to those of skill in the art, such as, for example, transmission electron microscopy, scanning electron microscopy, atomic force microscopy, and/or dynamic laser light scattering. The change and/or variance in size, shape, and/or diameter may be determined by measuring the particles size, shape, and/or diameter at two or more (e.g., 2, 3, 4, 5, etc.) different points in time (e.g., after the particle is formed and a period of time after the initial measurement (e.g., 1 month later)). In some embodiments, the size, shape, and/or diameter of a particle may be determined before, during, and/or after administration and/or delivery to a subject, tissue, and/or cell.

A polymer used to prepare a particle of the present invention may have any suitable molecular weight. In some embodiments, the polymer may have a molecular weight in a range of about 10 kDaltons to about 125 kDaltons, such as, for example, a molecular weight in a range of about 30 kDaltons to about 85 kDaltons, about 10 kDaltons to about 50 kDaltons, about 50 kDaltons to about 90 kDaltons, about 10 kDaltons to about 100 kDaltons, about 100 kDaltons to about 125 kDaltons, or about 45 kDaltons to about 60 kDaltons. In some embodiments, the polymer may have a molecular weight of about 10, 20, 30, 40, 50, 60, 70, 80, 90, 100, 110, 120, 125 kDaltons or more. The molecular weight of a polymer used to prepare a particle of the present invention may be determined using methods known in the art, such as, for example, by NMR and/or GPC. The particle may comprise linear and/or branched PEI. In some embodiments, the particle may comprise branched PEI. The particle may comprise PEI (linear and/or branched) having any suitable molecular weight. In some embodiments, the particle may comprise PEI having a molecular weight in a range of about 1 kDalton to about 60 kDaltons, such as, for example, a molecular weight in a range of about 2 kDaltons to about 25 kDaltons, about 15 kDaltons to about 35 kDaltons, about 10 kDaltons to about 50 kDaltons, or about 20 kDaltons to about 30 kDaltons. In some embodiments, the particle may comprise PEI having a molecular weight of about 5, 10, 15, 20, 25, 30, 35, 40, 45, 50, 55, 60 kDaltons or more.

The particle may comprise PLGA having any suitable molecular weight. In some embodiments, the particle may comprise PLGA having a molecular weight in a range of about 1 kDalton to about 100 kDaltons, such as, for example, a molecular weight in a range of about 1 kDalton to about 60 kDaltons, about 4 kDaltons to about 50 kDaltons, about 5 kDaltons to about 15 kDaltons, about 15 kDaltons to about 35 kDaltons, about 20 kDaltons to about 30 kDaltons, about 40 kDaltons to about 60 kDaltons, or about 50 kDaltons to about 100 kDaltons. In some embodiments, the particle may comprise PLGA having a molecular weight of about 5, 10, 15, 20, 25, 30, 35, 40, 45, 50, 55, 60, 65, 70, 75, 80, 85, 90, 95, 100 kDaltons or more.

The particle may comprise a polymer with PLGA and PEI in any suitable ratio. For example, the particle may comprise a polymer with PLGA and PEI in a ratio of 1:1, 2:1, 3:1, 4:1, 5:1, 6:1, 1:2, 1:3, 1:4, 1:5, 1:6 (PLGA: PEI) and/or any ratio therein. In some embodiments, PLGA and PEI are present in a polymer in a 1:1 (PLGA:PEI) ratio. In some embodiments, PLGA and PEI are present in a polymer in a 3:1 (PLGA:PEI) ratio.

Some embodiments may provide a particle comprising PLGA-g-PEI that comprises PEI having a molecular weight of 25 kDa and 3 PLGA having a molecular weight of 4 kDa (e.g., PgP-12k). In some embodiments, the PLGA-g-PEI comprising 4 kDa PLGA and 25 kDa PEI may have a molecular weight of in a range of about 35 kDa to about 45 kDa as determined by NMR and GPC.

Some embodiments may provide a particle comprising PLGA-g-PEI that comprises PEI having a molecular weight of 25 kDa and PLGA having a molecular weight of 25 kDa (e.g., PgP-25k). In some embodiments, the PLGA-g-PEI comprising 25 kDa PLGA and 25 kDa PEI may have a molecular weight in a range of about 45 kDa to about 55 kDa as determined by NMR and GPC.

Some embodiments may provide a particle comprising PLGA-g-PEI that comprises PEI having a molecular weight of 25 kDa and PLGA having a molecular weight of 50 kDa (e.g., PgP-50k). In some embodiments, the PLGA-g-PEI comprising 50 kDa PLGA and 25 kDa PEI may have a molecular weight in a range of about 70 kDa to about 80 kDa as determined by NMR and GPC.

A particle of the present invention may comprise any polymer with a suitable hydrophilic lipophilic balance (HLB). In some embodiments, the polymer may have a HLB in a range of about 4 to about 16, such as, for example, a HLB in a range of about 6 to about 14 or about 8 to about 12. In some embodiments, the polymer may have a HLB of about 4, 5, 6, 7, 8, 9, 10, 11, 12, 13, 14, 15, or 16. In some embodiments, the polymer may have a HLB in a range of about 8.5 to about 16, about 9 to about 15, about 10 to about 14, or about 12 to 14. The HLB of a polymer may be determined using methods known to those of skill in the art. In some embodiments, a particle may comprise a polymer with a HLB of 13.51 (e.g., PgP-12k), a polymer with a HLB of 10 (e.g., PgP-25k), and/or a polymer with a HLB of 6.67 (e.g., PgP-50k). While not wishing to be bound to any particular theory, the HLB of a polymer may influence micelle stability and may be important in delivering a nucleic acid and/or therapeutic agent into a cell in serum conditions. In some embodiments, the HLB of a polymer (e.g., an amphiphilic copolymer) may be determined by dividing the molecular weight of the hydrophilic portion of the polymer by the molecular weight of the whole polymer, then multiplying the product by twenty. Micelle stability can refer to and/or describe the ability of a particle and/or micelle to remain intact upon dilution. In some embodiments, micelle stability may be determined by the critical micelle concentration (CMC) of the particle and/or micelle. In some embodiments, a particle of the present invention may have a CMC in a range of about 0.05 mg/mL to about 1 mg/mL. In some embodiments, the particle may have a CMC in a range of about 0.1 mg/mL to about 0.75 mg/mL, about 0.25 mg/mL to about 0.5 mg/mL, about 0.1 mg/mL to about 0.3 mg/mL, about 0.3 mg/mL to about 0.6 mg/mL, about 0.5 mg/mL to about 0.8 mg/mL, or about 0.75 mg/mL to about 1 mg/mL. In some embodiments, a particle may have a CMC that is less than 0.7 mg/mL. In some embodiments, a lower CMC value may indicate that the particle is more stable (e.g., more thermodynamically and/or kinetically stable). The critical micelle concentration of a particle may be determined using methods known to those of skill in the art, such as, for example, by using a dye dissolution method.

In some embodiments, a particle of the present invention may have high transfection efficiency in serum and/or in vivo. The inventors of the present invention unexpectedly discovered that a particle of the present invention may have high transfection efficiency in serum and/or in vivo. Particles of the present invention may comprise PEI, and branched PEI (MW 25000) is not efficient in vivo because the polyplex can interact with negatively charged serum proteins and then be removed from the body by reticulo-endothelial cells such as macrophages. However, a particle of the present invention may have high transfection efficiency in vivo and/or in serum conditions, such as, for example, in 10% serum conditions, optionally in which the total protein content is about 7%. Some embodiments include that a particle of the present invention may have transfection efficiency in serum and/or in vivo of at least about 5% or more, such as, for example, about 10%, 15%, 20%, 25%, 30%, 35%, 40%, 45%, 50%, 55%, 60%, 65%, 70%, 75%, 80%, 85%, 90%, 95%, 98%, 99% or more. Transfection efficiency in serum and/or in vivo may be measured by methods known to those of skill in the art, such as, for example, by using flow cytometry, e.g., using flow cytometry with green fluorescent protein as a reporter gene.

In some embodiments, the particle may have an increased transfection efficiency in serum compared to a commercially available non-viral vector. A particle of the present invention may have an increased transfection efficiency in serum compared to a commercially available non-viral vector of at least about 5%, 10%, 15%, 20%, 25%, 30%, 35%, 40%, 45%, 50%, 55%, 60%, 65%, 70%, 75%, 80%, 85%, 90%, 95%, 98%, 99% or more.

In some embodiments, a particle of the present invention may exhibit stability during storage for a given period of time. That is, the particle may have a shelf-life for a particular length of time when stored under recommended storage conditions. For example, the particle may be stable for at least about 1, 2, 3, 4, 5, 6, 7 or more day(s), or 1, 2, 3, 4, or more week(s), or 1, 2, 3, 4, 5, 6, 7, 8, 9, 10, 11, 12, or more month(s) at a temperature in a range of about 1° C. to about 30° C. In some embodiments, stability is determined at a temperature of about 4° C. or at about 25° C. Stability may be determined by the size and/or shape of the particle. For example, a stable particle may change and/or vary in size and/or shape by less than about ±20% (e.g., less than about ±15%, 10%, 5%, or 1%) compared to another measurement at a different point in time. In some embodiments, stability may be determined by particle size, gel retardation assay, and/or the transfection efficiency of a particle. For example, a stable particle may have a transfection efficiency that changes and/or varies by less than about ±20% (e.g., less than about ±15%, 10%, 5%, or 1%) compared to another measurement at a different point in time. In some embodiments, a particle of the present invention (e.g., a particle comprising a targeting moiety, therapeutic agent, and/or nucleic acid) may exhibit stability characterized by retardation of electrophoretic mobility and retention of transfection efficiency during storage in solution at 4° C. for at least 6 months.

Provided according to some embodiments of the present invention are methods of using a particle of the present invention.

In some embodiments, a method of delivering at least one therapeutic agent and/or at least one nucleic acid to a target is provided. The method may comprise administering a particle of the present invention to a target, thereby delivering the at least one therapeutic agent and/or the at least one nucleic acid to the target. Some embodiments include administering the particle to a subject, tissue, and/or cell. In some embodiments, the particle comprises at least one targeting moiety and the at least one targeting moiety is directed to and/or specific for the target (e.g., a cell and/or tissue). Some embodiments include that the at least one therapeutic agent and the at least one nucleic acid are simultaneously delivered to the target, and the at least one targeting moiety may direct and/or bind the particle to the target.

Some embodiments include a method of promoting axonal regeneration and/or treating a CNS injury in a subject. The method may comprise administering a particle of the present invention to the subject, thereby promoting axonal regeneration and/or treating a CNS injury in the subject. The particle may comprise at least one targeting moiety and the at least one targeting moiety may comprise a neuron-specific targeting moiety, such as, for example, a NgR1 (Nogo receptor) antibody and/or L1 neural cell adhesion molecule. The particle may comprise at least one therapeutic agent that may comprise a phosphodieserase inhibitor (e.g., Rolipram). The particle may comprise at least one nucleic acid that may comprise RhoA siRNAs, PKC siRNAs, EGFR siRNAs and/or PTP sigma. In some embodiments, the at least one therapeutic agent and/or at least one nucleic acid directly and/or indirectly promote axonal regeneration in the subject. In some embodiments, the at least one therapeutic agent and/or at least one nucleic acid target and/or interact with at least one mechanism (e.g., 1, 2, 3, 4, or more mechanisms) that inhibits axonal regeneration.

In some embodiments, a method of treating cancer in a subject is provided. The method may comprise administering a particle of the present invention to the subject, thereby treating cancer in the subject. The cancer may be a drug resistant cancer. In some embodiments, the cancer may be breast cancer, brain cancer, prostate cancer, ovarian cancer, colon cancer, and/or pancreas cancer. The particle may comprise at least one targeting moiety that may comprise a cancer tissue-specific targeting moiety. In some embodiments, the at least one targeting moiety comprises folic acid and/or an antibody (e.g., Her2 (Human epidermal growth factor receptor) antibody). The particle may comprise at least one therapeutic agent that may comprise a hydrophobic anticancer drug. In some embodiments, the at least one therapeutic agent comprises doxorubicin and/or paclitaxel. The particle may comprise at least one nucleic acid that may comprise a nucleic acid that is involved in drug resistance.

In some embodiments, the at least one nucleic acid is complementary to a drug resistance responsible gene. In some embodiments, the at least one nucleic acid comprises, MGMT siRNAs, RPN2 siRNAs, and/or P-glycoprotein (MDR1) siRNAs.

"Treat," "treating" or "treatment of" (and grammatical variations thereof) as used herein refer to any type of treatment that imparts a benefit to a subject and may mean that the severity of the subject's condition is reduced, at least partially improved or ameliorated and/or that some alleviation, mitigation or decrease in at least one clinical symptom is achieved and/or there is a delay in the progression of the disease or disorder.

Some embodiments include a method of increasing the therapeutic efficiency of a therapeutic agent and/or nucleic acid in a subject. The method may comprise administering a particle of the present invention to the subject, thereby increasing the therapeutic efficiency of the therapeutic agent and/or nucleic acid in the subject.

A method of the present invention may provide reduced side effect(s) in a subject compared to a conventional therapy, such as, for example, a conventional therapy administering the same therapeutic agent and/or nucleic acid to a subject. In some embodiments, systemic side effects associated with administering a particle of the present invention comprising a therapeutic agent and/or nucleic acid may be reduced compared to a conventional therapy. In some embodiments, a method of the present invention may provide reduced side effect(s) (e.g., systemic side effects) in a subject by about 5%, 10%, 20%, 30%, 40%, 50%, 60%, 70%, 80%, 90%, 95%, 98%, 99% or more compared to a conventional therapy.

Provided herein are compositions comprising a particle of the present invention. In some embodiments, the composition may be a pharmaceutical composition. In some embodiments, a pharmaceutical composition of the present invention may comprise a particle of the present invention and a pharmaceutically acceptable carrier. Any suitable pharmaceutically acceptable carrier known to those of skill in the art may be used in a pharmaceutical composition of the present invention. A composition (e.g., a pharmaceutical composition and/or formulation) of the present invention for administration to a subject may provide a concentration of the particle in a range of about 0.1 mg of the particle/kg of the subject to about 50 mg of the particle/kg of the subject, such as, for example, in a range of about 2.5 mg/kg to about 50 mg/kg, about 5 mg/kg to about 30 mg/kg, or about 10 mg/kg to about 25 mg/kg. In some embodiments, a composition of the present invention for administering to a subject may provide a concentration of the particle in a range of about 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg of the particle/kg of the subject. In some embodiments, a composition of the present invention may be administered to a subject via systemic injection.

A medicament may be provided according to some embodiments of the present invention. In some embodiments, a medicament of the present invention may comprise a particle of the present invention and an acceptable carrier. Any suitable carrier known to those of skill in the art may be used in a medicament of the present invention. A medicament of the present invention for administration to a subject may provide a concentration of the particle in a range of about 0.1 mg of the particle/kg of the subject to about 50 mg of the particle/kg of the subject, such as, for example, in a range of about 2.5 mg/kg to about 50 mg/kg, about 5 mg/kg to about 30 mg/kg, or about 10 mg/kg to about 25 mg/kg. In some embodiments, a medicament of the present invention for administering to a subject may provide a concentration of the particle in a range of about 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg of the particle/kg of the subject. In some embodiments, a medicament of the present invention may be administered to a subject via systemic injection.

"Pharmaceutically acceptable carrier" and "acceptable carrier" as used herein refer to a carrier that is compatible with other ingredients in the pharmaceutical composition or medicament and that is not harmful or deleterious to the subject, i.e., the carrier can be administered to a subject without causing any undesirable biological effects such as toxicity. The carrier may be a solid or a liquid, or both, and may be formulated with a composition of this invention as a unit-dose formulation, which may contain a particle of the present invention in an amount of about 0.01% or 0.5% to about 95% or 99% by weight of the composition.

The compositions and medicaments of the invention may optionally comprise medicinal agents, pharmaceutical agents, carriers, adjuvants, dispersing agents, diluents, and the like.

A particle of the present invention may be formulated for administration and/or delivery in a pharmaceutical carrier in accordance with known techniques. See, e.g., Remington, *The Science And Practice of Pharmacy* (9$^{th}$ Ed. 1995). In the manufacture of a pharmaceutical formulation according to the invention, a particle of the present may be admixed with, inter alia, an acceptable carrier. One or more particles may be incorporated in a formulation of the invention, which may be prepared by any of the well-known techniques of pharmacy.

Formulations of the invention include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the liver, into the brain for delivery to the central nervous system, into the pancreas, or into a tumor or the tissue surrounding a tumor). The most suitable route in any given case will depend on the nature and severity of the condition being treated and on the nature of the particular particle that is being used.

In some embodiments, a pharmaceutical composition and/or medicament of the present invention may be suitable for intrathecal delivery and/or may be administered to a patient in need thereof intrathecally. In certain embodiments, a pharmaceutical composition and/or medicament of the present invention may be administered by intrathecal injection and/or by a pump providing intrathecal delivery.

For injection, the carrier may be a liquid, such as sterile pyrogen-free water, pyrogen-free phosphate-buffered saline solution, bacteriostatic water, or CREMOPHOR® EL[R] (BASF, Parsippany, N.J.). For other methods of administration, the carrier may be either solid or liquid.

For oral administration, the particle may be administered in solid dosage forms, such as capsules, tablets, and powders, or in liquid dosage forms, such as elixirs, syrups, and suspensions. Particles may be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like.

Similar diluents may be used to make compressed tablets. Both tablets and capsules may be manufactured as sustained release products to provide for continuous release of medication over a period of hours. Compressed tablets may be sugar coated or film coated to mask any unpleasant taste and protect the tablet from the atmosphere, or enteric-coated for selective disintegration in the gastrointestinal tract. Liquid dosage forms for oral administration may contain coloring and flavoring to increase patient acceptance.

Formulations suitable for buccal (sub-lingual) administration include lozenges comprising the particle in a flavored base, usually sucrose and acacia or tragacanth; and pastilles comprising the particle in an inert base such as gelatin and glycerin or sucrose and acacia.

Formulations suitable for parenteral administration comprise sterile aqueous and non-aqueous injection solutions comprising the particle, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit/dose or multi-dose containers, for example sealed ampoules and vials, and may be stored in a freeze-dried (lyophilized) condition requiring only the addition of the sterile liquid carrier, for example, saline or water-for-injection immediately prior to use.

Extemporaneous injection solutions and suspensions may be prepared from sterile powders, granules and tablets of the kind previously described. For example, in one aspect of the present invention, there is provided an injectable, stable, sterile composition comprising a particle of the invention, in a unit dosage form in a sealed container. The particle may be provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the particle. An emulsifying agent that is pharmaceutically acceptable may be employed in sufficient quantity to emulsify the particle in an aqueous carrier. One such useful emulsifying agent is phosphatidyl choline.

Formulations suitable for rectal administration are preferably presented as unit dose suppositories. These may be prepared by admixing the particles with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, Tyle, *Pharm. Res.* 3:318 (1986), which is incorporated by reference herein in its entirety) and typically take the form of an optionally buffered aqueous solution of the particle. Suitable formulations comprise citrate or bis/tris buffer (pH 6) or ethanol/water and contain from 0.1 to 0.2M of the particle.

The particle may alternatively be formulated for nasal administration or otherwise administered to the lungs of a subject by any suitable means, e.g., administered by an aerosol suspension of respirable particles comprising a particle of the present invention, which the subject inhales. The respirable particles may be liquid or solid. The term "aerosol" includes any gas-borne suspended phase, which is capable of being inhaled into the bronchioles or nasal passages. Specifically, aerosol includes a gas-borne suspension of droplets, as may be produced in a metered dose inhaler or nebulizer, or in a mist sprayer. Aerosol also includes a dry powder composition suspended in air or other carrier gas, which may be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising a particle of the present invention may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising a particle of the present invention may likewise be produced with any solid particulate medicament aerosol generator, by techniques known in the pharmaceutical art.

Alternatively, one may administer particles, compositions, and/or medicaments of the present invention in a local rather than systemic manner, for example, by injection, in a depot or sustained-release formulation.

According to some embodiments of the present invention, a particle, composition (e.g., pharmaceutical composition), and/or medicament of the present invention may be administered to a subject and/or used to treat a subject. For example, in some embodiments, a method of the present invention may comprise administering a particle, composition, and/or medicament according to embodiments of the present invention to promote axonal regeneration, treat a central nervous system (CNS) injury, to treat cancer, and/or to increase the therapeutic efficiency of a therapeutic agent and/or nucleic acid in a subject.

The present invention finds use in both veterinary and medical applications. Subjects suitable to be treated with a method of the present invention include, but are not limited to, mammalian subjects. Mammals of the present invention include, but are not limited to, canines, felines, bovines, caprines, equines, ovines, porcines, rodents (e.g. rats and mice), lagomorphs, primates (e.g., simians and humans), non-human primates (e.g., monkeys, baboons, chimpanzees, gorillas), and the like, and mammals in utero. Any mammalian subject in need of being treated according to the present invention is suitable. Human subjects of both genders and at any stage of development (i.e., neonate, infant, juvenile, adolescent, adult) may be treated according to the present invention. In some embodiments of the present invention, the subject is a mammal and in certain embodiments the subject is a human. Human subjects include both males and females of all ages including fetal, neonatal, infant, juvenile, adolescent, adult, and geriatric subjects as well as pregnant subjects. In particular embodiments of the present invention, the subject is a human adolescent and/or adult.

The methods of the present invention may also be carried out on animal subjects, particularly mammalian subjects such as mice, rats, dogs, cats, livestock and horses for veterinary purposes, and/or for drug screening and/or drug development purposes.

In some embodiments, the subject is "in need of" a method of the present invention, e.g., the subject has been diagnosed with, is at risk for, and/or is believed to have a disease, disorder, or condition that may be treated using a method of the present invention. In some embodiments, the subject has cancer and/or a CNS injury.

In order that the invention described herein may be more fully understood, the following examples are set forth. It should be understood that these examples are for illustrative purposes only and are not to be construed as limiting this invention in any manner.

EXAMPLES

Example 1

Spinal cord injury commonly leads to permanent motor and sensory deficits due to the limited regenerative capacity of the adult central nervous system (CNS). In this study, cationic amphiphilic block copolymers, poly (lactide-co-glycolide)-graft-polyethylenimine (PgP), were synthesized by grafting low molecular weight PLGA (4 kDa) to bPEI (25 kDa) at approximately a 3:1 ratio as an efficient nonviral vector. It is shown that PgP micelle is capable of efficiently transfecting plasmid DNA (pDNA) and siRNA in the presence of 10% serum in neuroglioma (C6) cells, neuroblastoma (B35) cells, and primary E8 chick forebrain neurons (CFN) with pDNA transfection efficiencies of 58.8%, 75.1%, and 8.1%, respectively. It is also shown that PgP provides high-level transgene expression in the rat spinal cord in vivo that is substantially greater than that attained with bPEI. The combination of improved transfection and reduced cytotoxicity in vitro in the presence of serum and in vivo transfection of neural cells relative to conventional bPEI provides support that PgP may be a promising nonviral vector for therapeutic nucleic acid delivery for neural regeneration.

Materials and Methods:

Materials

Poly (lactide-co-glycolide) (PLGA 4 kDa, 50:50) with a carboxylic end group was purchased from Durect Corporation (Pelham, Ala.). Branched poly (ethylenimine) (bPEI) (Mw 25 kDa), dicyclohexylcarbodiimide (DCC), and N-hydroxysuccinimide (NHS) were purchased from Sigma (Milwaukee, Wis.). Dialysis tubing (MWCO=50,000) was purchased from Spectrum (Houston, Tex.). QIAgen maxi plasmid purification kit was purchased from QIAgen (Valencia, Calif.). Plasmid DNA encoding the Monster Green Fluorescent Protein (phMGFP Vector: pGFP), plasmid DNA encoding beta-galactosidase (pSV40-β-gal, p β-gal), and marker dye for gel electrophoresis (Blue/Orange 6× Loading Dye) were purchased from Promega (Madison, Wis.). Albumin standard and BCA protein assay kit were obtained from Pierce (Rockford, Ill.). A molecular weight ladder of pDNA (1 kb DNA Ladder) was purchased from Gibco BRL (Grand Island, N.Y.). Dulbecco's Modification of Eagle's Medium/Ham's F-12 50/50 mix with L-glutamine (DMEM/F12), 100× stock solution of penicillin/streptomycin, and 0.05% trypsin/0.53 mM EDTA in Hank's Balanced Salt Solution were purchased from Mediatech Inc (Manassas, Va.). Bovine growth serum (BGS) was obtained from Hyclone (Logan, Utah). Basal Medium Eagle (BME) was obtained from Life Technologies (Grand Island, N.Y.). Other reagents were commercial special-grade, used without further purification.

Synthesis of Poly (Lactide-Co-Glycolide)-g-Poly (Ethylenimine) (PgP)

To synthesize PgP-12k, PgP-25k, and PgP-50k, the carboxylic end group on the PLGA (MW: 4 kDa, 25 kDa or 50 kDa) was activated by NHS and DCC for two hours in DMF (Scheme 1). PgP-12k was synthesized by using a 4:1 mole ratio of PLGA-4 kDa to bPEI (25 kDa) and PgP-25k and PgP-50k were synthesized by using a 1.2:1 mole ratio of PLGA-25 kDa and PgP-50 kDa to PEI. Briefly, PLGA was dissolved in dried anhydrous DMF. N-hydroxysuccinimide (NHS) and N,N'-Dicyclohexylcarbodiimide (DCC) were added to the reaction solution and this mixture was stirred for 2 hrs to activate the carboxylic end group of PLGA. The resulting precipitate, dicyclohexyl urea (DCU), was removed by filtration. bPEI was dissolved in dried DMF. The activated PLGA solution was added dropwise to the bPEI solution over 30 min, and then the mixture was allowed to react for 24 hrs at room temperature with stirring. Poly (lactide-co-glycolide)-g-poly (ethylenimine) (PgP) was purified by dialysis against deionized water using a membrane filter (MWCO=50,000), centrifuged at 5,000 rpm for 10 minutes to remove unreacted PLGA precipitate, and lyophilized. The structure of PgP was determined by FT-IR and $^1$H-NMR (300 MHz, Bruker) using $D_2O$ as a solvent. The molecular weight was determined by gel permeation chromatography (GPC, Waters, Milford, Mass.) using an Ultrahydrogel 250 column (7.8×300 mm) and guard column—6×40 mm with water as the mobile phase. PgP solution (3 mg/ml, 20 µl) was injected by auto-injector and the flow rate was 0.7 ml/minute. A Waters 1525 HPLC pump and Waters 2414 Refractive Index Detector were used. Dextrans at molecular weights of 5, 12, 25, 50, and 80 kDa were used as standards.

Scheme 1: Synthesis of PgP

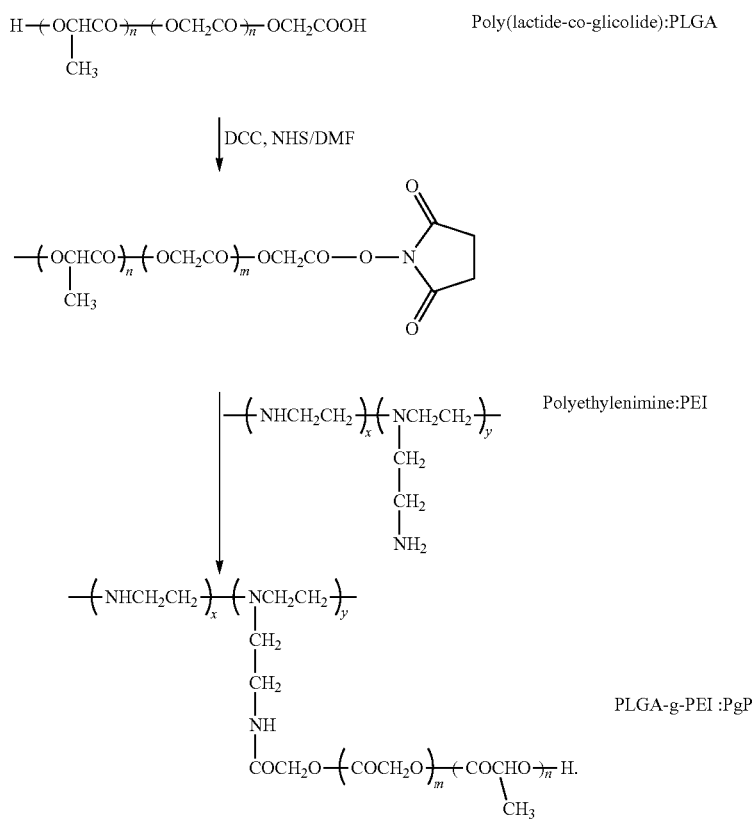

The structure and molecular weight (MW) of the PgP used to prepare the particles was determined using 1H-NMR and GPC, and the HLB (Hydrophilic and lipophilic balance) value of the polymer used to prepare the particles was calculated (Table 1) based on MW of PLGA and PEI to synthesize PgP-12k, PgP-25k, and PgP-50k.

TABLE 1

Molecular weight and HLB of the polymer used to prepare the particles.

| PgP Polymer | NMR | GPC | HLB |
|---|---|---|---|
| PgP-12k | 39,480 | 38,168 | 13.11 |
| PgP-25k |  | 48,791 | 10.24 |
| PgP-50k |  | 75,000 | 6.67 |

Critical Micelle Concentration

The critical micelle concentration (CMC) of particles was determined using a dye solubilization method. Ten µl of 0.4 mM DPH (1, 6-diphenyl-1,3,5-hexatriene) was added to 1 ml solutions of various concentration of 3 different PgPs (PgP-12k, PgP-25k, and PgP-50k) and incubated in the dark at room temperature for 6 hrs. Absorbance at 356 nm was plotted against the polymer concentration and the CMC was determined as the point of intersection between linear extrapolations of the absorbance in low- and high-concentration regions (Table 2).

TABLE 2

Critical micelle concentration of the particles.

| PgP polymers | CMC |
|---|---|
| PgP-12k | 0.69 mg/ml (18.6 × $10^{-6}$ M) |
| PgP-25k | 0.45 mg/mL (9.39 × $10^{-6}$ M) |
| PgP-50k | 0.16 mg/mL (2.07 × $10^{-6}$ M) |

Plasmid Amplification and Purification

Plasmids encoding the Monster Green Fluorescent Protein (pGFP) and beta-galactosidase (pβGal) were transformed into *Escherichia coli* DH5a and amplified in LB medium at 37° C. overnight with shaking at 250 rpm. pGFP and pβGal were purified using the Endofree Maxi Plasmid purification kit (Qiagen) according to the manufacturer's instructions. The quality and quantity of pGFP and pβGal were determined using Biotek Take 3 microplate reader (BioTek, Synergy HT).

Preparation and Characterization of PgP/Nucleic Acid Polyplexes.

PgP/pDNA polyplexes were prepared at various N/P (nitrogen atoms of polymer/phosphorus atoms of pDNA) ratios ranging from 5 to 30. DNA (20 µg pDNA) and varying amounts of PgP were separately diluted in 500 µl of deionized water. After 10 min, solutions were mixed and incubated for 30 min at 37° C. bPEI/pDNA at N/P ratio 5/1 was prepared for comparison. PgP/siRNA complex at N/P ratio of 30/1 and PEI/siRNA at N/P ratio of 5/1 were prepared in nuclease-free water.

Polyplexes were initially characterized immediately after preparation. Particle size (PS) was determined by dynamic laser light scattering (DLS) using Zeta PALS (Brookhaven Instruments Corp, Holtsville, N.Y.) and reported as effective mean diameter. ζ-potential (ZP) was measured electrophoretically using the same apparatus. In order to evaluate the effect of serum on particle size, PgP/pDNA and PEI/pDNA prepared at N/P ratio of 30/1 and 5/1, respectively, were diluted in 10% serum-containing media and PS measured by DLS. PgP/pDNA and PgP/siRNA prepared at N/P ratio of 30/1 were imaged by transmission electron microscopy (TEM, Hitachi H-7600, Tokyo, Japan). After polyplex formation, a small drop (5 □l) of sample solution was placed onto a carbon coated copper grid (CF300-CU, Electron Microscopy Sciences, PA), blotted with filter paper to remove excessive water, and dried at room temperature. The specimens were vapor-stained with 0.5% Ruthenium tetroxide ($RuO_4$) solution (Electron Microscopy Sciences, PA) to improve the contrast, and imaged by TEM at an acceleration voltage of 100 kV and magnifications of ×50K and ×200K.

Gel Retardation Assay

Gel retardation assays were performed to confirm the ability of PgP to neutralize the negative charge of pDNA and provide protection from degradation. First, PgP/pDNA polyplexes were prepared at various N/P ratios in deionized water and incubated for 30 min at 37° C. In the second study, PgP/pDNA at N/P ratio of 30/1 was prepared and incubated in 10% serum-containing media for 3 days at 37° C. Naked DNA was included in both studies for comparison. The samples were electrophoresed on a 1% (w/v) agarose gel for 90 min at 80 V. The gel was stained with ethidium bromide (0.5 µg/ml) for 30 min and imaged on a UV illuminator (Alpha Innotech FluorChem SP imager) to visualize the migration of polyplexes and control pDNA.

Cell Culture

C6 (rat glioblastoma) and B35 (rat neuroblastoma) cells were grown in DMEM/F12 supplemented with 10% FBS and 100 IU/ml penicillin/100 µg/ml streptomycin at 37° C. under 5% $CO_2$. Cells were trypsinized and plated in 12-well plates (0.9~1.1×$10^5$ cells/well).

Chicken eggs were obtained from Clemson University's Morgan Poultry Center and incubated at 37° C. with light rocking. Primary E8 chick forebrain neurons (CFNs) were prepared as described by Heidemann et. al, *Methods in cell biology* 2003; 71:51-65. Briefly, after removal of the meninges, the forebrains were isolated and incubated in 0.25% trypsin for 5 minutes at 37° C. The trypsin was then aspirated and the tissue was triturated; centrifuged; resuspended in BME supplemented with 10% FBS, 6 mg/mL D-glucose, 2 mM L-glutamine, and 1% antibiotic; and plated in 12-well plates (0.9~1.1×$10^6$ cells/well) pre-coated with 0.01% Poly-L-lysine. Transfection efficiency and cytotoxicity of PgP/pGFP polyplexes in serum-free and 10% serum conditions C6, B35, or CFN cells were plated in 12-well plates and cultured overnight. PgP/pGFP polyplexes (2 µg of pGFP) were prepared at charge (N/P) ratios ranging from 5/1 to 30/1. For the serum-free condition, the cells were transfected in media without serum for 4 hrs and then the media were removed and replaced by fresh media containing 10% FBS. The cells were incubated for an additional 44 hrs. For the serum condition, the cells were transfected in media containing 10% FBS for 24 hrs; then the media were removed and replaced by fresh media containing 10% FBS. The cells were incubated an additional 24 hrs. GFP expression was measured by flow cytometry (Guava easyCyte, Millipore) and the results were expressed as % transfected cells. Transfection efficiency of PgP/pGFP polyplexes at different N/P ratios was compared with that of bPEI/pGFP at an N/P ratio of 5/1 as a positive control and non-transfected cells were used as a control. Cytotoxicity relative to non-transfected control was analyzed in parallel experiments by MTT assay. At 48 hours post-transfection, media were replaced with 1 ml of fresh DMEM without serum containing 240 µl of MTT (Thiazolyl Blue Tetrazolium Bromide, Sigma-Aldrich) solution in PBS (2 mg/ml). Plates were incubated an additional 4 hours at 37° C. MTT-containing medium was removed, and 1.5 ml of DMSO was added to dissolve the formazan crystals formed by live cells. Absorbance was measured at 570 nm. The cell viability (%) was calculated according to the following equation:

$$\text{Cell viability (\%)}=(OD_{570\ (sample)}/OD_{570\ (control)})\times 100\%$$

Neuron-Specific Beta-3-Tubulin Staining

To confirm neuronal transfection, transfected CFN cultures were fixed with 4% paraformaldehyde after 48 hrs transfection, stained by immunocytochemistry using a monoclonal beta-III-tubulin (Abcam) primary antibody and Alexa Fluor 594-conjugated goat anti-mouse IgG secondary antibody, and digitally imaged using an inverted epifluorescent microscope (Zeiss Axiovert 200, Göttingen, Germany).

Effect of Polymer Concentration on Cytotoxicity

To characterize the dose-dependent cytotoxicity of PgP, B35 and C6 cells were transfected using various concentrations of PgP/pGFP prepared at N/P ratio of 30/1. At 48 hours post-transfection, cell viability was evaluated as described above.

Time Course Study of Polyplex Stability and Transfection Efficiency

To evaluate the polyplex stability over time, PgP/pGFP was prepared at N/P ratio of 30/1 and stored at 4° C. for up to 7 days. At pre-determined time points, polyplex stability was evaluated by gel retardation assay and transfection efficiency measured in B35 cells in 10% serum condition.

Transfection Efficiency Using siGLO Red

The siGLO Red transfection indicator (siGLO®, Thermo Fisher Scientific), consisting of a fluorescently labeled siRNA duplex with a chemical modification for nuclear localization, was used to evaluate siRNA transfection efficiency. PgP/siGLO Red complexes (1 µg siGLO Red) at various N/P ratio were transfected in B35 cells in 10% serum condition. bPEI/siGLO at N/P 5/1 and RNAiMAX (Life Technologies) were used as positive controls. The cells were incubated at 37° C. for 24 hrs and then the media were replaced with fresh media containing 10% FBS. At 48 hours post-transfection, siGLO Red-transfected cells were counted by flow cytometry and the results expressed as % transfected cells. Cytotoxicity relative to untransfected cells control was analyzed in parallel experiments by MTT assay.

Silencing Efficiency of PgP/GFP siRNA after Co-Transfection of bPEI/pGFP Complexes To evaluate PgP as a siRNA delivery carrier, B35 cells were co-transfected with bPEI/pGFP at an N/P ratio of 5/1 and PgP/GFP siRNA (Ambion) complexes at N/P ratio of 30/1. The cells were first transfected with bPEI/pGFP (2 µg of pGFP) in serum-free condition as described above. At 4 hrs post-transfection, the media were removed and replaced by fresh media containing 10% FBS. PgP/GFP siRNA complexes at N/P ratio 30/1 (1 µg of siRNA) were co-transfected in the bPEI/pGFP-transfected B35 cells in 10% serum condition and then incubated for 24 hrs. RNAiMAX/GFP siRNA polyplexes prepared according to the manufacturer's protocol and bPEI/GFP siRNA (N/P ratio of 5/1) were used as controls. The level of GFP fluorescence was measured by flow cytometry. GFP-silencing efficiency of PgP/GFP siRNA polyplexes was calculated relative to the level of GFP fluorescence obtained from bPEI/pGFP (N/P: 5/1) transfection.

Transfection Efficiency of PgP/pβ-Gal Polyplexes in 10% Serum Media Condition In Vitro To evaluate PgP as a nucleic acid carrier in vivo, plasmid-β-Galactosidase (pβ-Gal) was used to avoid potential interference of tissue autofluoresecence with GFP analysis. Polyplexes at an N/P ratio of 30/1 were prepared using both pGFP and pβ-Gal in three different conditions to test the effects of the polyplex preparation volume and injection through a Hamilton syringe (G 26) on transfection. The three preparation conditions were 1) mixing 50 µl of pDNA(2 µg) with 50 µl of PgP (Low conc: used above for in vitro studies), 2) mixing 10 µl of pDNA(10 µg) with µl of PgP (High Conc.: planned for in vivo studies) and then diluting to 500 µl, and 3) mixing 10 µl of pDNA(10 µg) with 10 µl of PgP and passing it through a Hamilton syringe (G 26) (Hamilton syringe: simulation of polyplex injection in vivo), and then diluted to 500 µl. C6 cells were trypsinized and plated in 12-well plates. Transfection was performed in 10% serum condition as described above (Section 2.6.2). One hundred µl (2 µg pDNA) of each of three polyplexes were transfected in C6 cells. GFP expression was evaluated by flow cytometry and β-Gal expression was evaluated by staining β-Gal+ cells using a β-Gal staining kit (Life Technologies) at 48 days post-transfection.

Transfection Efficiency of PgP/pβ-Gal Polyplexes in Rat Spinal Cord In Vivo

All surgical procedures and postoperative care will be conducted according to NIH guidelines for the care and use of laboratory animal (NIH publication No. 86-23, revised 1996) and under the supervision of the Clemson University Animal Research Committee. Sprague Dawley rats (male, 200 gm) were anesthetized with isoflurane gas. Their backs were shaved and prepared with betadine solution, chlorhexidine, and sterile water. A 4 cm longitudinal incision was made over the dorsal mid-thoracic region and the T9 spinous process was identified and removed using an orthopedic bone cutter and then the ligamentum flavum was removed to expose the intervertebral space. PgP/pβ-gal complexes (10 µg pβ-gal, 20 µl) were prepared at an N/P ratio of 30/1 as described above (Section 2.8) and injected into the exposed dorsal T9 spinal cord using a 26-gauge Hamilton syringe (Hamilton Company, Reno, Nev., USA). bPEI/pβ-gal at an N/P ratio of 5/1 was used as positive control and naked pβ-gal was used as negative control. Following injection, the paraspinal muscles were closed with 4-0 vicryl suture and the skin was closed with 3-0 silk suture. At 7 days after polyplex injection, animals were anesthetized by isoflurane gas and sacrificed via cardiac perfusion with 4% paraformaldehyde solution. The retrieved spinal cords were fixed with 4% paraformaldehyde solution and 10 µm thick sections cut longitudinally and mounted on positively charged glass slides. To evaluate transfection efficiency, sections were stained using a β-Gal staining kit (Life Technologies) to detect β-Gal+ transfected cells.

Statistical Analysis

The results were analyzed using Student's t-test for pairwise comparisons and ANOVA for multiple comparisons (significance level: $p<0.05$).

Results

Synthesis and Characterization of Poly (Lactide-Co-Glycolide)-g-Polyethylenimine (PgP)

The amphiphilic graft copolymer PgP was synthesized by conjugating the carboxyl groups of PLGA to the amine groups of bPEI through amide bonds. The structure and grafting ratio of PLGA to bPEI were confirmed by $^1$H-NMR ($\delta=2.4\sim3.5$ (m, PEI backbone $—CH_2$), $\delta=1.4\sim1.6$ (d, 3H, PLGA $—CH_3$), $\delta=4.3$ (q, 1H, PLGA $—CH$), $\delta=3.9$ (s, 2H, PLGA $—CH_2$)). The ratio of the integrals of the PEI backbone ($\delta=2.4\sim3.5$) to the methylene of PLGA ($\delta=3.9$) indicated that approximately three PLGA (MW: 4 kDa) were grafted to each PEI. The molecular weight of PgP was determined as approximately 38,168 by GPC using dextran standards. The critical micellar concentration (CMC) of PgP determined by dye dissolution method was 0.69 mg/ml ($1.86\times10^{-5}$ M).

Preparation and Characterization of PgP/Nucleic Acid Polyplexes

Figure 2A:
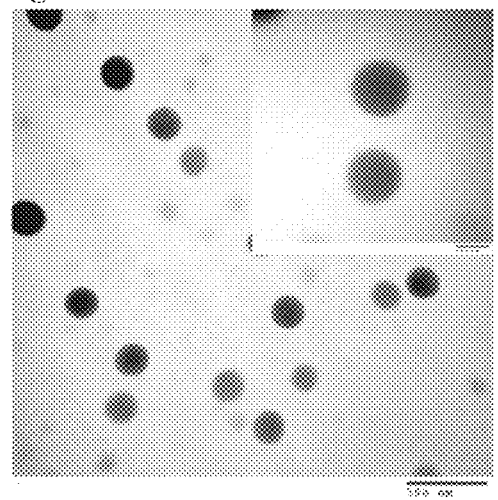
FIG. 2A shows transmission electron microscopy images of PgP/pDNA prepared at N/P ratio of 30/1. Scare bars indicate 500 nm (main image) and 100 nm (enlarged, inset image).
Figure 2B:
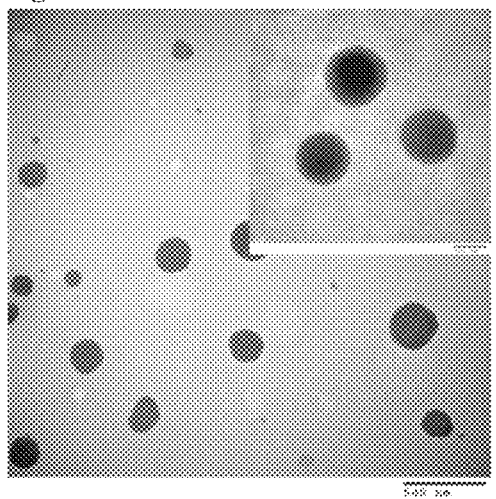
FIG. 2B shows transmission electron microscopy images of PgP/siRNA prepared at N/P ratio of 30/1. Scare bars indicate 500 nm (main image) and 100 nm (enlarged, inset image).

The particle size, polydispersity, and surface charge of PgP/pDNA and bPEI/pDNA polyplexes at various N/P ratios are shown in Table 3. The mean particle size of PgP/pDNA polyplexes at N/P ratio of 5/1 was ~340 nm and larger than the bPEI control (~160 nm) at the same N/P ratio. PgP/pDNA particle size significantly decreased relative to the N/P 5/1 group at ratios of 10/1 and higher, ranging between ~150-180 nm. The zeta potential at N/P ratio 2.5/1 was +14.07 mV for bPEI/pDNA polyplexes, while that of PgP/pDNA was −14.94 mV. At N/P ratios of 5/1 and higher, both bPEI/pDNA and PgP/pDNA polyplexes were positively charged, indicating that negatively charged pDNA was completely neutralized by polycationic polymers. The particle size of bPEI/pDNA (N/P ratio of 5/1) and PgP/pDNA (N/P ratio of 30/1) polyplexes were also measured after exposure to 10% serum-containing media. Particle size of bPEI/pDNA (317.8±13.6 nm, PDI: 0.281±0.009) and PgP/pDNA (258.7±2.9 nm, PDI: 0.212±0.021) increased relative to previous measurements in water by approximately 101% and 50%, respectively. PgP/siRNA (N/P ratio of 30/1) and bPEI/siRNA (N/P ratio of 5/1) formed polyplexes of similar particle size (~200 nm) in water. Both PgP/siRNA and bPEI/siRNA were positively charged and the zeta potential of bPEI/siRNA at N/P ratio of 5/1 was significantly higher than PgP/siRNA at N/P ratio of 30/1 (Table 3). TEM imaging of PgP/pDNA and PgP/siRNA prepared at 30/1 N/P ratio provided confirmation of particle size analysis and showed that both groups of polyplexes formed particles with spherical morphology (FIGS. 2A and 2B).

Figure 4A:
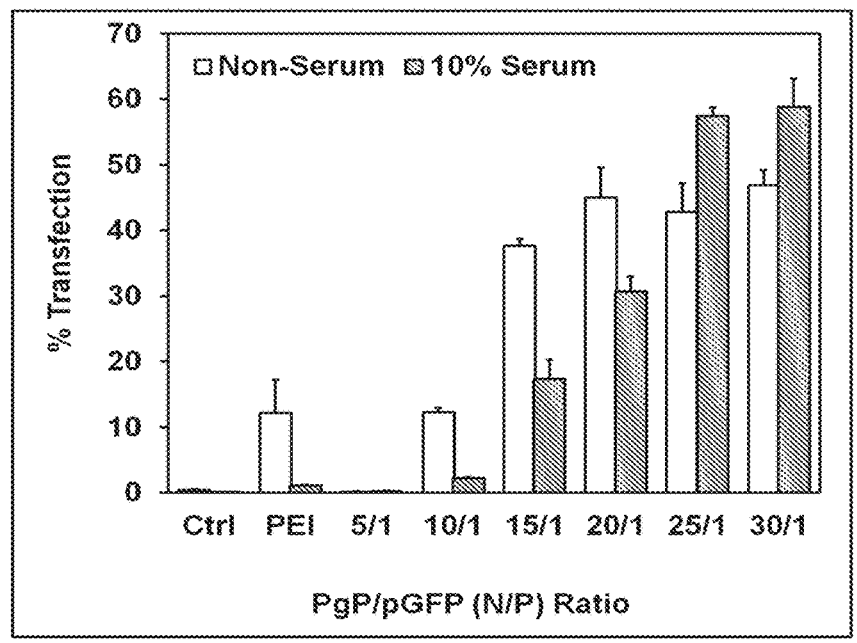
FIG. 4A shows a graph of the percent of transfection after transfection of PgP/pGFP polyplexes at varying N/P ratios in C6 neuroglioma cells in serum-free and 10% serum conditions. bPEI/pGFP at N/P ratio of 5/1 was used as a positive control. Data represent the mean±SEM (n=6). *: P<0.05 (10% Serum), †: P<0.05 (Serum-free) compared to bPEI.
Figure 4B:
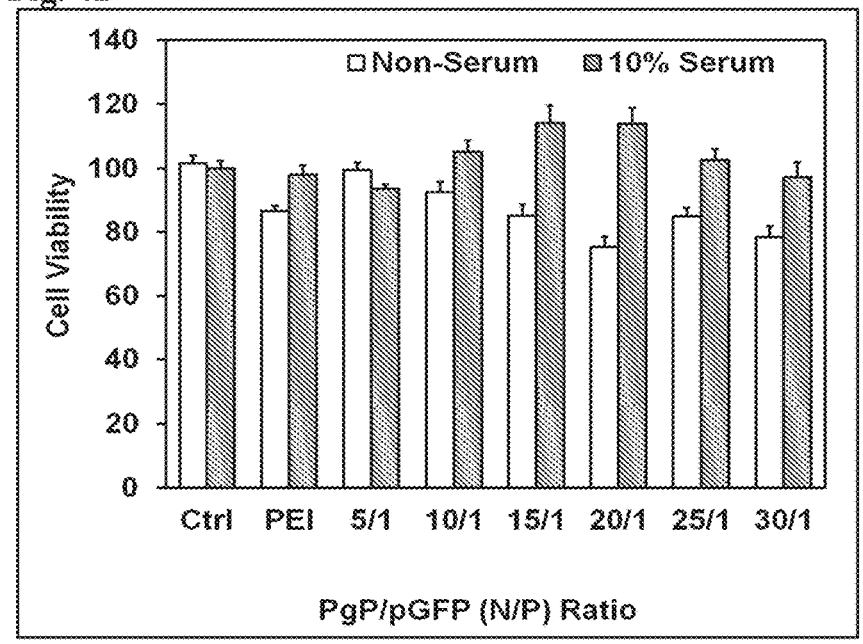
FIG. 4B shows a graph of cell viability after transfection of PgP/pGFP polyplexes at varying N/P ratios in C6 neuroglioma cells in serum-free and 10% serum conditions. bPEI/pGFP at N/P ratio of 5/1 was used as a positive control. Data represent the mean±SEM (n=6). *: P<0.05 (10% Serum), †: P<0.05 (Serum-free) compared to bPEI.
Figure 4C:
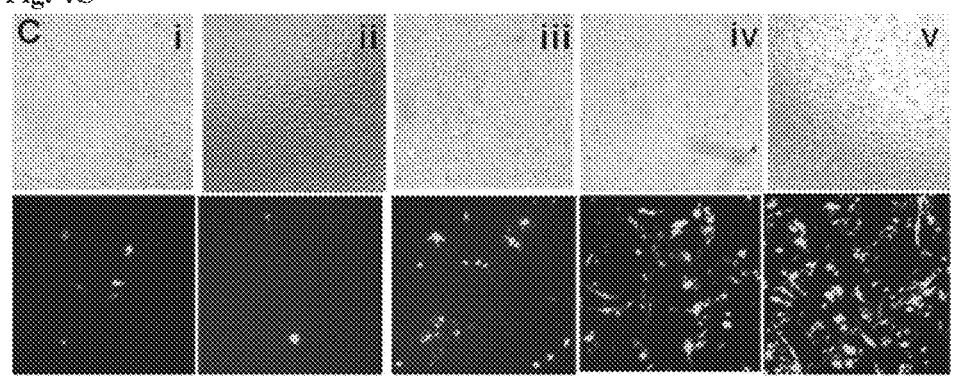
FIG. 4C shows representative images of C6 cells after transfection with PgP/pGFP polyplexes at various N/P ratios in 10% serum condition (Top: Phase contrast, Bottom: Fluorescence). Panel i) bPEI/pGFP at N/P ratio of 5/1, panels ii-v) PgP/pGFP at N/P ratios of 10/1, 15/1, 25/1 and 30/1, respectively. Original magnification: 100×.

13% for bPEI control (FIG. 4A). In the presence of 10% serum, transfection efficiency also increased with increasing N/P ratio and was significantly higher than the bPEI control at all N/P ratios. PgP achieved a maximum transfection efficiency of 59% (N/P ratio 30/1) in the presence of serum, while that of the bPEI control (2%) was significantly reduced relative to serum-free conditions. Cell viability was modestly but significantly decreased after transfection in serum-free conditions with PgP/pGFP at N/P ratios of 15 and greater (FIG. 4B). However, no significant differences in cell viability relative to non-transfected control were observed after transfection in the presence of serum, indicating that PgP/pDNA polyplexes were non-toxic under these more physiologically relevant conditions. FIG. 4C shows representative images of C6 cells transfected at varying N/P ratio in the 10% serum condition.

In B35 cells, the transfection efficiency of PgP/pGFP polyplexes also increased with increasing N/P ratio in both serum-free and 10% serum condition and reached 68.3% and 75.1% at N/P ratio of 30/1, respectively, while the transfec-

TABLE 3

Mean particle size (PS), zeta potential (ZP), and polydispersity index (PDI) of PgP/nucleic acids polyplexes.

| | PEI/pDNA | PgP/DNA | | | |
|---|---|---|---|---|---|
| N/P ratio | 5 | 5 | 10 | 15 | 20 |
| Particle Size (nm) | 157.43 ± 8.13 | 340.57 ± 13.68 | 146.87 ± 2.51 | 150.90 ± 2.69 | 167.1 ± 3.04 |
| Zeta Potential (mV) | 40.20 ± 0.81 | 27.25 ± 9.53 | 44.12 ± 2.28 | 46.35 ± 1.84 | 47.97 ± 0.51 |
| PDI | 0.148 ± 0.01 | 0.176 ± 0.05 | 0.140 ± 0.01 | 0.136 ± 0.03 | 0.135 ± 0.02 |

| | PgP/DNA | | PEI/siRNA | PgP/siRNA |
|---|---|---|---|---|
| N/P ratio | 25 | 30 | 5 | 30 |
| Particle Size (nm) | 177.173 ± 1.67 | 177.63 ± 1.95 | 213.87 ± 39.24 | 201.42 ± 4.17 |
| Zeta Potential (mV) | 49.57 ± 1.34 | 48.28 ± 0.85 | 44.13 ± 1.33 | 30.63 ± 1.60 |
| PDI | 0.125 ± 0.02 | 0.136 ± 0.03 | 0.234 ± 0.104 | 0.238 ± 0.03 |

Figure 3A:
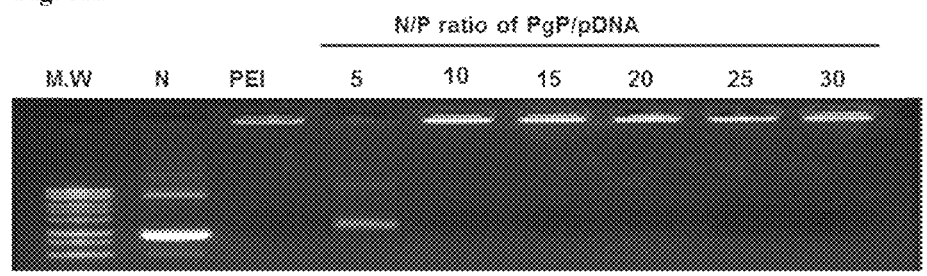
FIG. 3A shows an image of an agarose gel for PgP/pDNA polyplexes prepared at varying N/P ratios: Molecular weight Marker (Lane 1), naked pDNA (lane 2), bPEI/pDNA at N/P ratio of 5/1 (lane 3), and PgP/pDNA prepared at N/P ratios of 5/1, 10/1, 15/1, 20/1, 25/1, and 30/1 (lane 4, 5, 6, 7, 8, and 9), respectively.
Figure 3B:
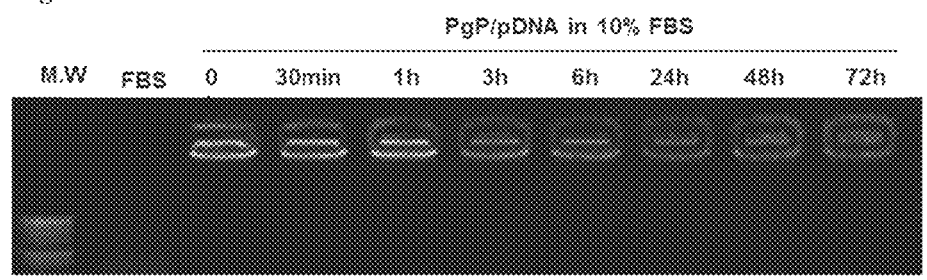
FIG. 3B shows an image of an agarose gel for PgP/pDNA polyplexes (N/P ratio of 30/1) at various time points (0, 30 min, 1, 3, 6, 24, 48, and 72 hours) during incubation in 10% serum-containing media.

Formation of polyelectrolyte complexes and neutralization of pDNA's negative charge was evaluated by gel retardation assay. Complete retardation of electrophoretic mobility was observed for bPEI/pDNA polyplexes prepared at 5/1 N/P ratio and PgP/pDNA polyplexes prepared at N/P ratios greater than or equal to 10/1 (FIG. 3A). Polyplexes incubated in 10% serum-containing media remained detectable in gel retardation assays for up to 3 days (FIG. 3B), while naked pDNA was undetectable after 30 minutes.
Transfection Efficiency and Cytotoxicity of Polyplexes In Vitro.

To evaluate the feasibility of PgP as a gene delivery carrier for CNS applications, the transfection efficiency of PgP/pGFP polyplexes at different N/P ratios in various neural cell types including C6, B35, and primary E8 chick forebrain neurons (CFNs) in both serum-free and 10% serum condition was tested. Transfection efficiency of PgP/pGFP polyplexes was compared with that of bPEI/pGFP at an N/P ratio of 5/1 as a positive control.

Figure 5A:
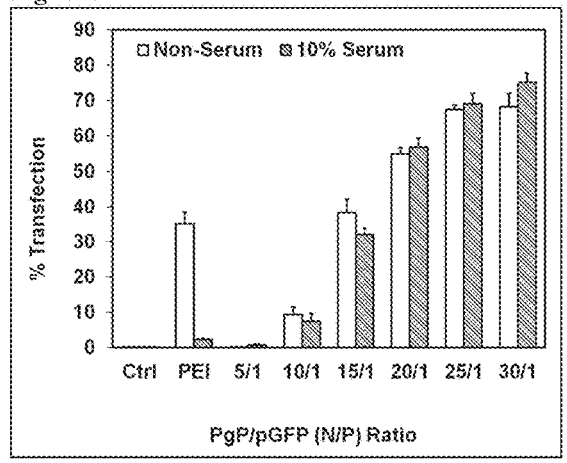
FIG. 5A shows a graph of the percent of transfection after transfection of PgP/pGFP polyplexes prepared at varying N/P ratios in B35 neuroblastoma cells in serum-free and 10% serum conditions. Data represent the mean±SEM (n=6). *: P<0.05 (10% Serum), †: P<0.05 (Serum-free) compared to bPEI/pGFP at N/P ratio of 5/1.
Figure 5B:
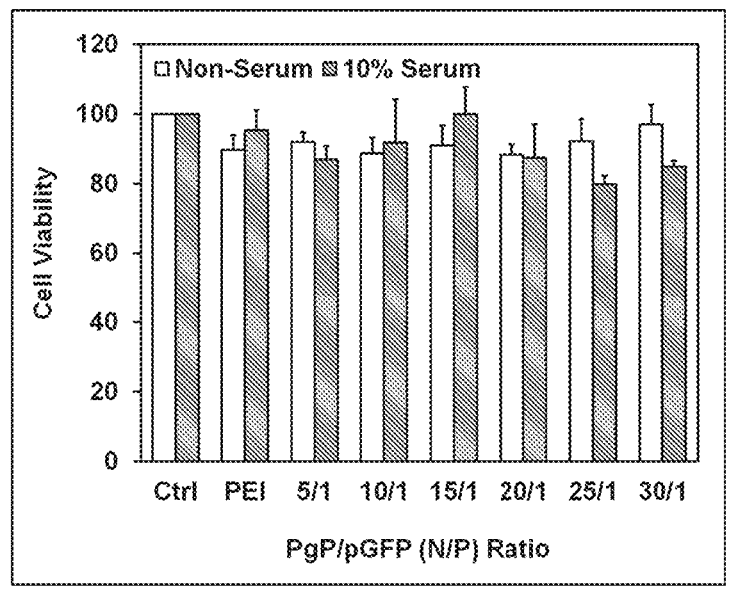
FIG. 5B shows a graph of cell viability after transfection of PgP/pGFP polyplexes prepared at varying N/P ratios in B35 neuroblastoma cells in serum-free and 10% serum conditions. Data represent the mean±SEM (n=6). *: P<0.05 (10% Serum), †: P<0.05 (Serum-free) compared to bPEI/pGFP at N/P ratio of 5/1.

FIGS. 4A-4C show the transfection efficiency and cytotoxicity of PgP/pGFP polyplexes in C6 cells. Transfection efficiency in serum-free media increased with increasing N/P ratio, attaining 47% at N/P ratio of 30/1 compared to tion efficiency of bPEI was significantly reduced from 35.3% in the serum-free condition to 2.27% in the 10% serum condition (FIG. 5A). PgP/pGFP polyplexes were also generally non-toxic in B35 cells, with significant changes in cell viability only observed at N/P ratios of 25/1 and 30/1 in the 10% serum condition (FIG. 5B). While exposure to serum reduces the performance of most nonviral vectors, these results demonstrate that PgP achieved significantly higher transfection efficiency than bPEI in the 10% serum condition medium at all N/P ratios in both C6 and B35 cell lines.

Figure 6A:
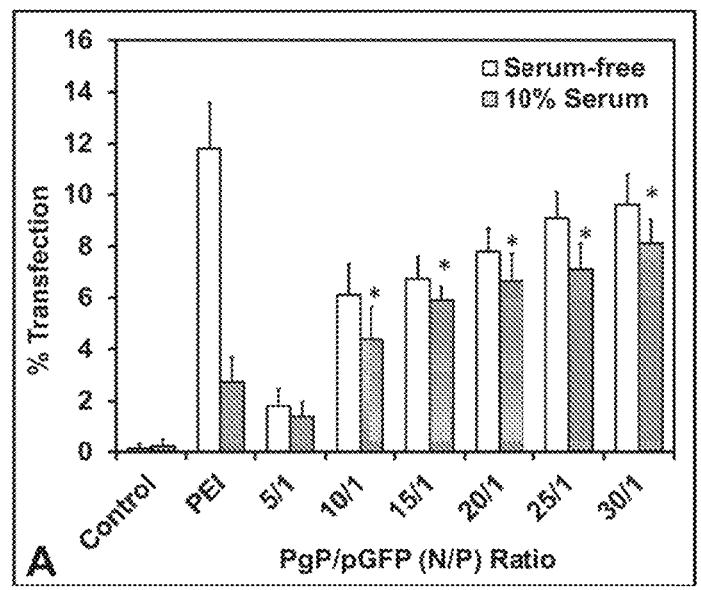
FIG. 6A shows a graph of the percent of transfection after transfection of PgP/pGFP polyplexes in primary E8 Chick forebrain neurons (CFNs) in serum-free and 10% serum conditions. Data represent the mean±SEM (n=6). *: P<0.05 (10% Serum), †: P<0.05 (Serum-free) compared to bPEI/pGFP at N/P ratio of 5/1.
Figure 6B:
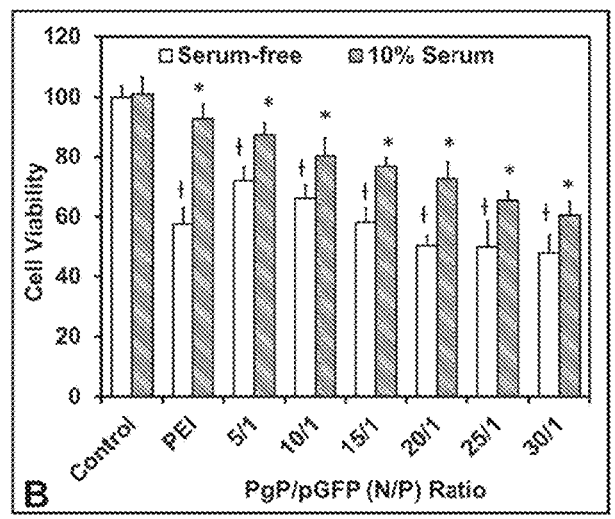
FIG. 6B shows a graph of cell viability after transfection of PgP/pGFP polyplexes in primary E8 Chick forebrain neurons (CFNs) in serum-free and 10% serum conditions. Data represent the mean±SEM (n=6). *: P<0.05 (10% Serum), †:P<0.05 (Serum-free) compared to bPEI/pGFP at N/P ratio of 5/1.
Figure 6C:
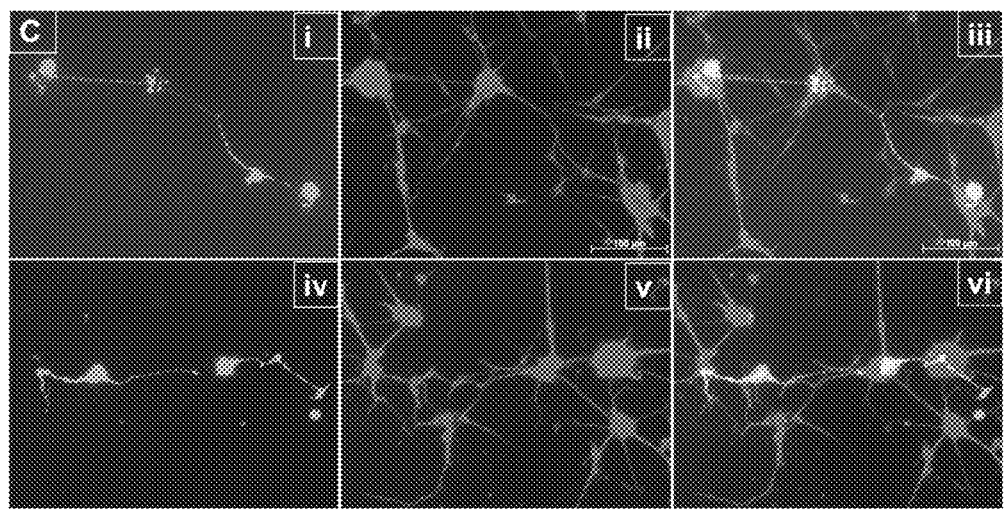
FIG. 6C shows representative images of GFP-transfected/beta-III-tubulin+primary E8 CFNs after transfection with PgP/pGFP, panel i: GFP transfection, panel ii: beta-III-tubulin staining, iii: overlay). Original magnification, 200×.

The feasibility of PgP as a gene delivery carrier to non-dividing primary E8 chick forebrain neurons was also evaluated. In serum-free conditions, transfection efficiency of bPEI/pGFP at N/P ratio of 5/1 (11.8%) was higher than that of PgP/pGFP complexes below 20/1 N/P ratio (9.62%), but didn't show any significant difference above 25/1 N/P ratio (FIG. 6A). In the 10% serum condition, transfection efficiency increased as the PgP/pGFP N/P ratio increased and the transfection efficiency was significantly higher at N/P ratios of 10/1 and above than the bPEI/pGFP control. The transfection efficiency of PgP/pGFP at N/P ratio of 30/1 (8.12%) was 3 times higher than that of the bPEI control (2.73%) in 10% serum condition ($P<0.05$). In both serum-free and 10% serum conditions, cytotoxicity increased as the PgP/pGFP N/P ratio increased (FIG. 6B). In the case of bPEI/pGFP at N/P 5/1, the cytotoxicity was very high in non-serum condition while it was less toxic in 10% serum condition, likely a result of low transfection. Representative images of GFP-transfected (grey), beta-III-tubulin+ (grey) primary E8 CFNs are shown in FIG. 6C.

Effect of the Polymer Concentration on Cytotoxicity

Figure 7A:
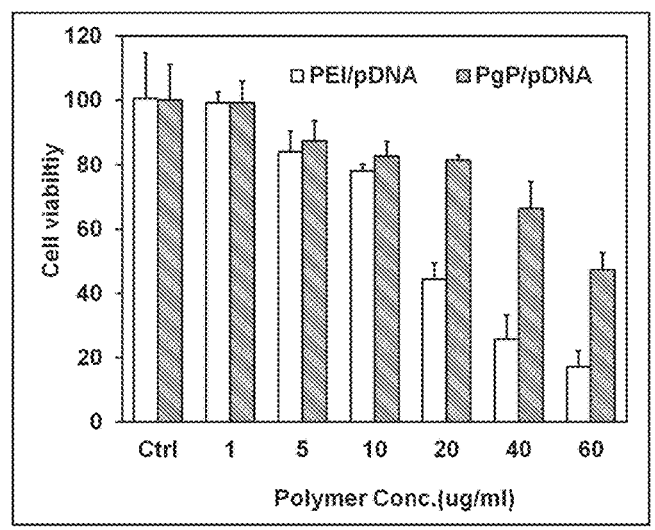
FIG. 7A shows a graph of cell viability of C6 glioma cells at 48 hours after transfection with varying concentrations of PgP/pGFP (N/P of 30/1) and bPEI/pGFP (N/P of 5/1) polyplexes in 10% serum condition. Data represent the mean±STD (n=4).
Figure 7B:
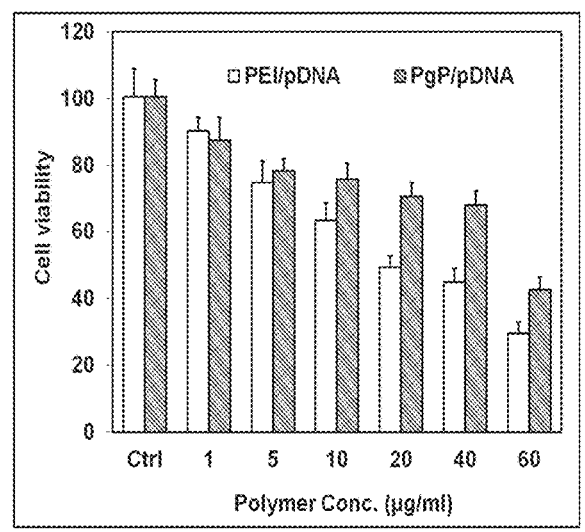
FIG. 7B shows a graph of cell viability of B35 neuroblastoma cells at 48 hours after transfection with varying concentrations of PgP/pGFP (N/P of 30/1) and bPEI/pGFP (N/P of 5/1) polyplexes in 10% serum condition. Data represent the mean±STD (n=4).

The cytotoxicity of PgP/pDNA (N/P ratio of 30/1) and bPEI/pDNA (N/P ratio of 5/1) polyplexes as a function of polymer concentration was also evaluated (FIGS. 7A and 7B). In both C6 cells and B35 cells, PgP/pDNA showed higher viability than bPEI/pDNA at all polymer concentrations and it was significantly different at higher concentrations (>20 µg/ml in C6 cells and >10 µg/ml in B35 cells).

Time Course Study of Polyplex Stability and Transfection Efficiency

Figure 8A:
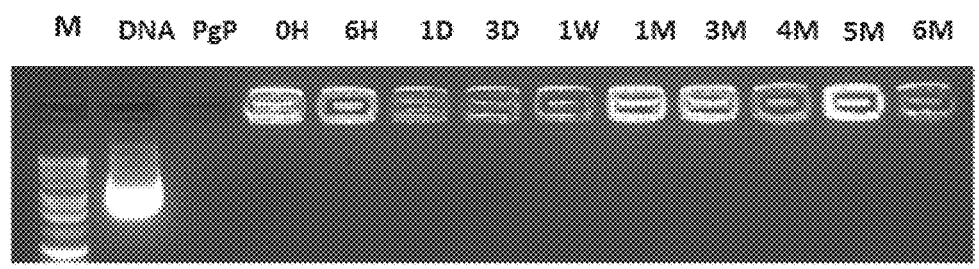
FIG. 8A shows an image of an agarose gel from the time course study of polyplex shelf-stability. PgP/pGFP (N/P of 30/1) polyplexes were prepared and stored at 4° C. for 6 months. The stability of polyplexes over time was evaluated by agarose gel electrophoresis: Molecular weight Marker (Lane 1), naked DNA (Lane 2), PgP (Lane 3), fresh polyplex (lane 4), 6 hours, 1 day, 3 days, 1 week, 1 month, 3 months, 4 months, 5 months, and 6 months (lane 5-13), respectively.
Figure 8B:
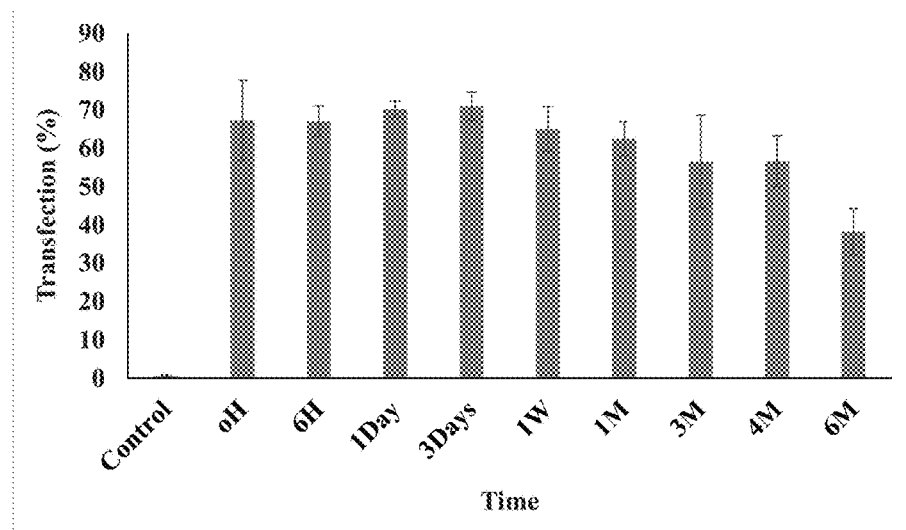
FIG. 8B shows a graph of transfection efficiency of polyplexes stored at 4° C. for 6 months. B35 cells were transfected with PgP/pGFP (N/P of 30/1) polyplexes at various time points during storage in 10% serum condition. Data represent the mean±SEM (n=6).

PgP/pGFP polyplexes prepared at N/P ratio of 30/1 and stored at 4° C. were stable and retarded in the wells at all time points and no degraded or dissociated DNA was observed (FIG. 8A). Stored polyplexes maintained high transfection efficiency in B35 cells in 10% serum condition that was not significantly different from freshly prepared polyplex controls at any time point (FIG. 8B).

Gene Knockdown Efficiency of PgP/GFP siRNA In Vitro

Figure 9A:
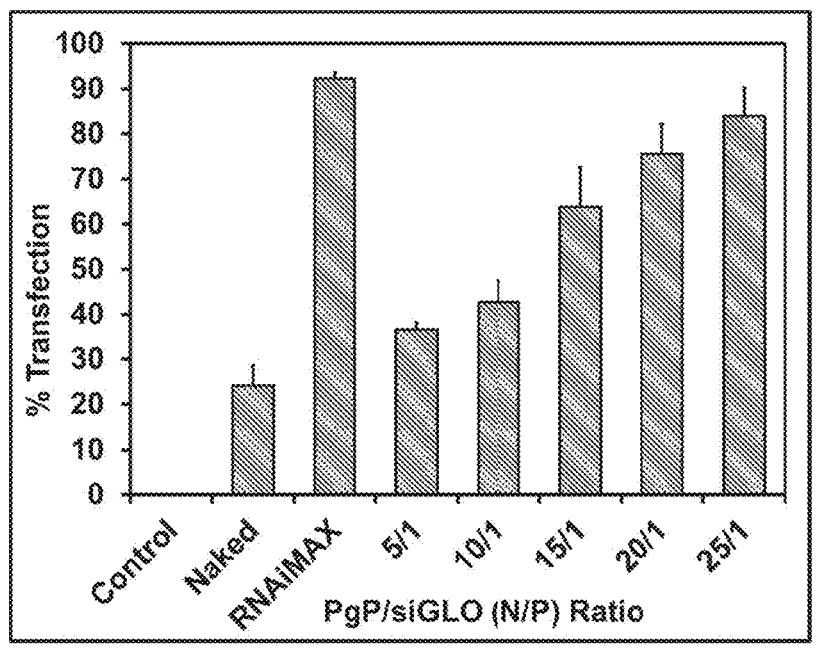
FIG. 9A shows a graph of transfection efficiency after transfection of PgP/siGLO red (1 g siGLO red/well) at varying N/P ratios in B35 cells in 10% serum condition. Data represent the mean±SEM (n=6). * P<0.05 compared to naked siGLO-red.
Figure 9B:
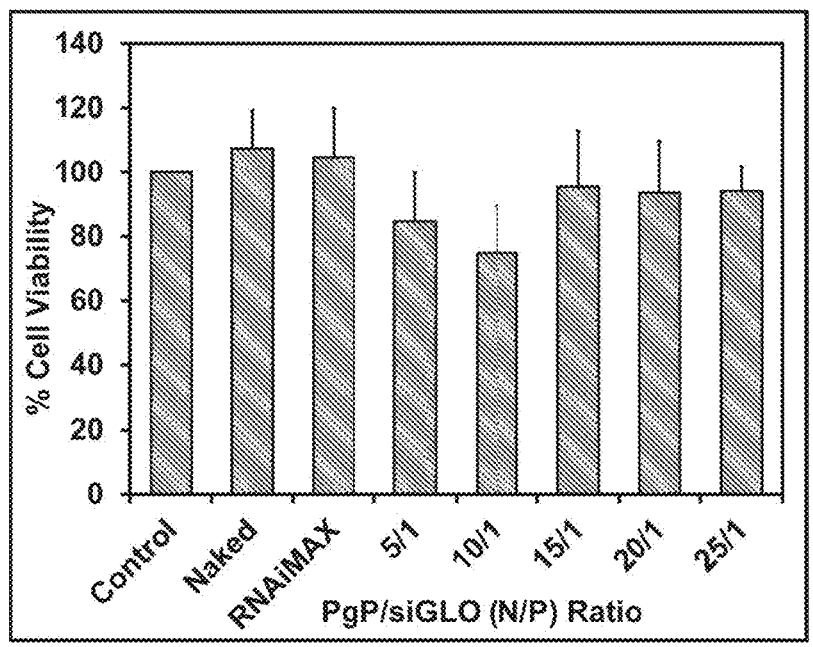
FIG. 9B shows a graph of cell viability after transfection of PgP/siGLO red (1 µg siGLO red/well) at varying N/P ratios in B35 cells in 10% serum condition. Data represent the mean t SEM (n=6). * P<0.05 compared to naked siGLO-red.
Figure 10A:
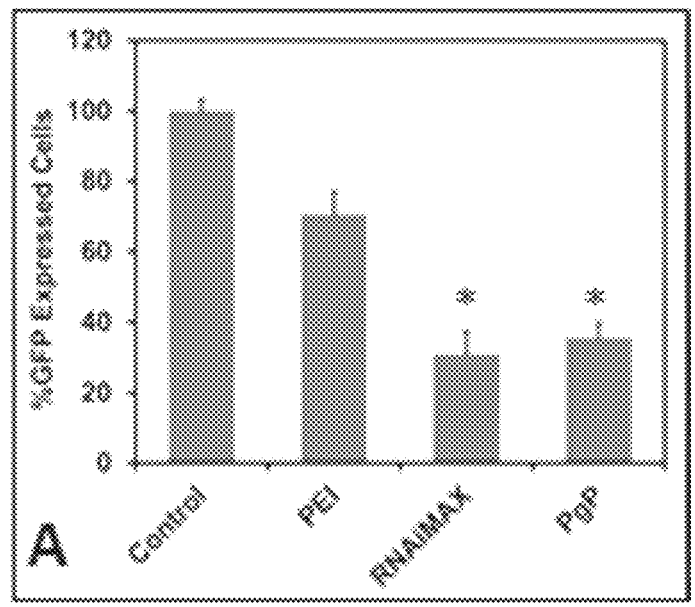
FIG. 10A shows a graph of percent of GFP knockdown after co-transfection with PgP/GFP siRNA at N/P ratio of 30/1, bPEI/GFP siRNA at N/P ratio of 5/1, and RNAiMAX/GFP siRNA controls relative to control transfected with bPEI/pGFP only. Data represent the mean±SEM (n=6) * P<0.05 compared to bPEI/pGFP at N/P ratio of 5/1.
Figure 10B:
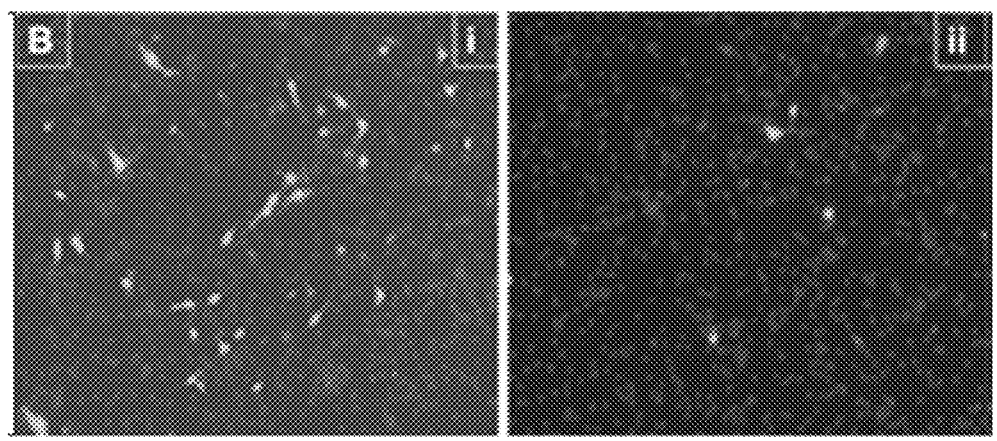
FIG. 10B shows representative images of GFP expression in B35 cells after transfection with PEI/pGFP at N/P of 5/1 alone panel (i) and after co-transfection with PgP/GFP siRNA at N/P ratio of 30/1 panel (ii), Grey: DAPI stained nuclei, Original magnification, 100×.

Intracellular delivery of siRNA was first evaluated by transfecting B35 cells with PgP/siGLO red transfection indicator at varying N/P ratios in 10% serum condition. PgP/siGLO red at an N/P ratio of 25/1 showed approximately 79% transfection efficiency, which was not significantly different from RNAimax (94%), while naked siGLO showed very low transfection (17%) (FIG. 9A). No significant differences in cell viability were observed relative to the non-transfected control (FIG. 9B). In the next study, gene knockdown efficiency was evaluated by co-transfection of PgP/GFP siRNA, bPEI/GFP siRNA, and RNAiMAX/GFP siRNA in bPEI/pGFP-transfected B35 cells. The relative GFP knockdown efficiency of PgP/GFP siRNA polyplexes at N/P ratios of 30/1 was ~65%, which was similar to that obtained with RNAiMAX/GFP siRNA (70%) (FIG. 10A). FIG. 10B shows representative images of GFP expression after serum-free transfection with bPEI/pGFP at N/P of 5/1 (FIG. 10B, panel i) and after co-transfection with PgP/GFP siRNA at N/P ratio of 30/1 in 10% serum (FIG. 10B, panel ii).

Transfection Efficiency of PgP/pβ-Gal Polyplexes in 10% Serum Media Condition In Vitro In order to minimize the sample volume required for injection into the spinal cord, polyplexes for in vivo studies were prepared at higher concentrations (10 µg pDNA/20 µl) than used for earlier in vitro studies (2 µg pDNA/100 µl). Therefore, in vitro tests were first performed to compare the transfection efficiency of pβ-Gal and pGFP polyplexes prepared at increased concentration and after passage through a Hamilton syringe (26G) to our conventional preparation and transfection procedure. GFP transfection measured by flow cytometry showed no significant differences between polyplexes prepared at low concentration without syringe passage and those prepared at high concentration with and without passage through a Hamilton syringe. These results demonstrate the PgP/pDNA polyplexes can be prepared at increased concentration and injected through small diameter syringe for in vivo delivery without loss of bioactivity.

Transfection of PgP/pβ-Gal Polyplexes in Rat Spinal Cord In Vivo

Figure 11A:
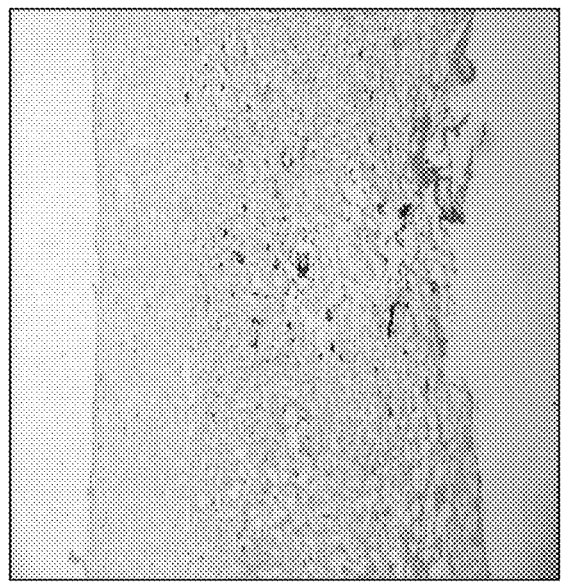
FIG. 11A shows an image of β-Gal transfected cells in rat T9 spinal cord at 7 days post-injection of naked pβ-Gal at 10 µg pβ-Gal per animal, original magnification: 40×.
Figure 11B:
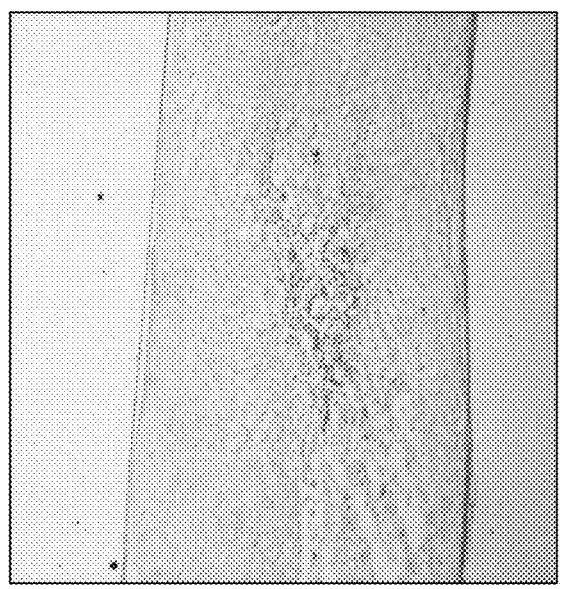
FIG. 11B shows an image of bPEI/pβ-Gal polyplexes at N/P of 5/1 at 10 µg pβ-Gal per animal, original magnification: 40×.
Figure 11C:
FIG. 11C shows an image of PgP/pβ-Gal polyplexes at N/P of 30/1 at 10 µg pβ-Gal per animal, original magnification: 40×.

Based on the in vitro studies in which transfection efficiency generally increased with increasing N/P ratio without substantially increasing cytocoxity in the presence of serum, a 30/1 N/P ratio for the spinal cord injection model was used. pβ-Gal was used for the in vivo model in order to avoid tissue autofluorescence confounding the interpretation of GFP transfection. Transfection efficiency in the rat spinal cord was observed in the order of PgP/pβ-Gal>>bPEI/pβ-Gal>naked pβ-Gal (FIGS. 11A-C). Representative images of β-Gal staining 7 days after injection of naked pβ-Gal (FIG. 11A), bPEI/pβ-Gal polyplexes (FIG. 11B), and PgP/pβ-Gal polyplexes (FIG. 11C). These results demonstrate that PgP nonviral vectors can achieve efficient transfection of neural cells in vivo.

Example 2

Neuron-specific nanotherapeutics for combinatorial therapy of drug and small interfering RNA (siRNA) targeting both extrinsic and intrinsic barriers were developed to promote axonal regeneration. The approach is based upon 1) anti-NgR1 antibody (Ab) conjugated to the nanoparticle surface will specifically deliver the nanotherapeutics to neurons and interfere with the function of existing NgR1 receptors by antagonizing the binding of myelin-associated inhibitors. 2) RhoA siRNA will be used to block the common intracellular signal transduction pathways responsible for both myelin- and CSPG-mediated growth inhibition and 3) rolipram (Rn), a phosphodiesterase 4 (PDE4) inhibitor will be employed to increase intrinsic neuronal growth capacity by preventing injury-induced reductions in cAMP levels. The belief is that these neuron-specific nanotherapeutics will improve axonal regeneration and functional recovery following SCI. Experiments are described below that support the use of such particles for neuron-specific nanotherapeutics.

Figure 12:
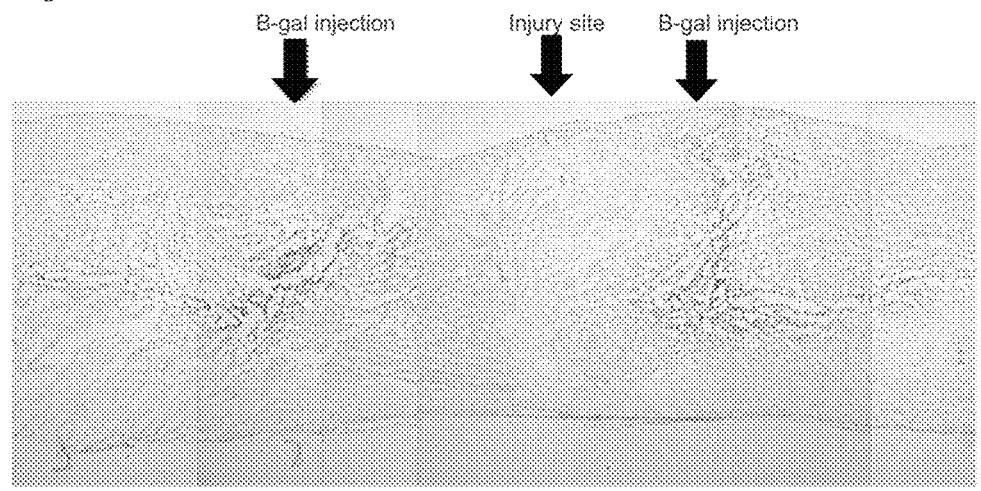
FIG. 12 shows an image of beta-gal expression in SCI at 7 days after PgP-12k/pβ-Gal injection in spinal cord injury site.
Figure 13A:
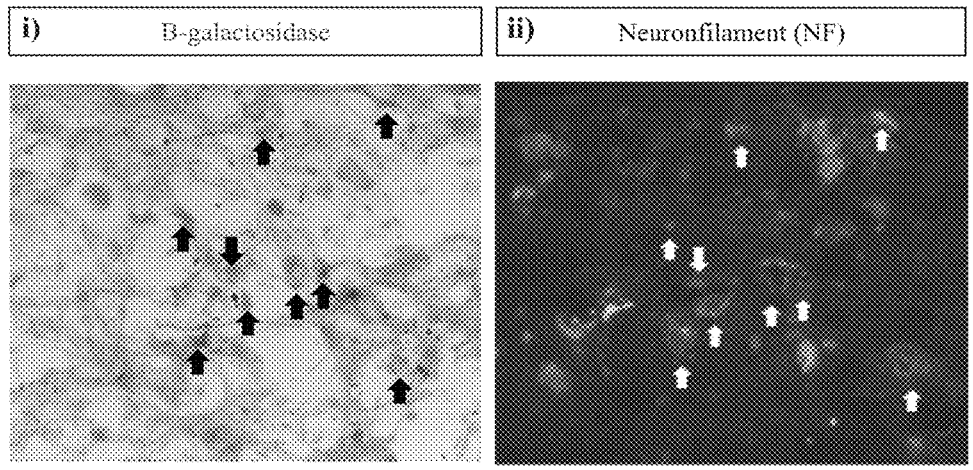
FIG. 13A shows an image of cells stained using a β-Gal staining kit (Life Technologies) to detect β-Gal+ transfected cells (panel i) and with neuron-specific neurofilament antibody to detect neuron cells (panel ii).
Figure 13B:
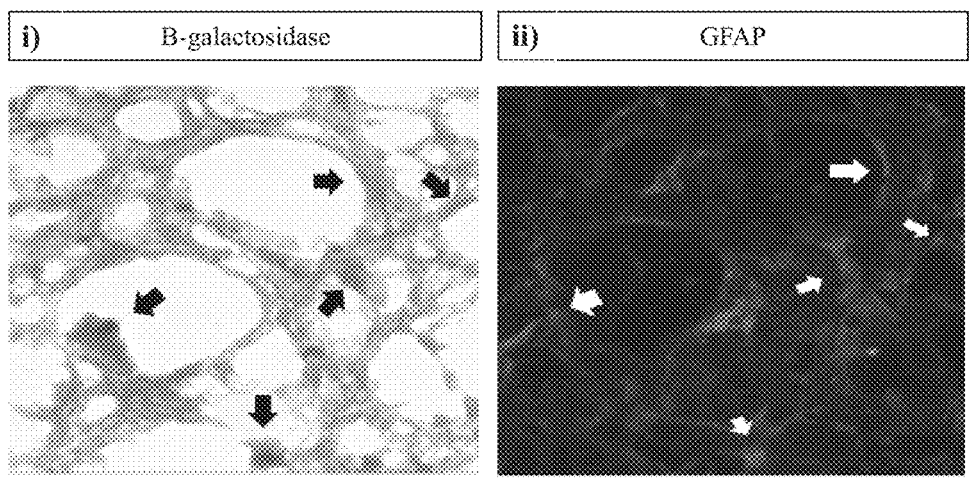
FIG. 13B shows an image of cells stained sing a β-Gal staining kit (Life Technologies) to detect β-Gal+ transfected cells (panel i) and with glial fibrillar acidic protein (GFAP) antibodies to detect astrocytes (panel ii).

Transfection Efficiency of PgP/pβ-Gal Polyplexes in Rat Compression Spinal Cord Injury Model In Vivo Sprague Dawley rats (male, 200 gm) were anesthetized with isoflurane gas. Their backs were shaved and prepared with betadine solution, chlorhexidine, and sterile water. The T9 spinous process were identified and a 4-cm longitudinal incision over the dorsal mid-thoracic region will be made using a #10-blade scalpel. The T9 spinous process will be removed using orthopedics bone cutter and rongeurs, and the ligamentum flavum will be removed, thereby exposing the intervertebral space. A vascular clip was inserted through the dorsal T8-T9 intervertebral space and spinal cord was compressed via vascular clip for 10 min (page 24). Following clip compression, PgP/pβ-gal complexes (10 µg pβ-gal, 20 µl) were prepared at an N/P ratio of 30/1 and injected into the injured dorsal T9 spinal cord using a 26-gauge Hamilton syringe. bPEI/pβ-gal at an N/P ratio of 5/1 and naked pβ-gal were used as controls. Following injection, the paraspinal muscles were closed with 4-0 vicryl suture, and the skin was closed with 3-0 silk suture. At 7 days after polyplex injection, animals were anesthetized by isoflurane gas and sacrificed via cardiac perfusion with 4% paraformaldehyde solution. The retrieved spinal cords were fixed with 4% paraformaldehyde solution and 10 µm thick sections cut and mounted on positively charged glass slides. To evaluate transfection efficiency, sections were stained using a β-Gal staining kit (Life Technologies) to detect β-Gal+ transfected cells. FIG. 12 shows β-galalctosidase expression by transfected cells in black at 7 days post-injection of PgP/pβ-Gal polyplex in rat compression SCI model. To identify the β-Gal+ cells, the neuron cells and astrocytes were stained using neuron-specific neurofilament and glial fibrillar acidic protein (GFAP) antibodies, respectively. FIGS. 13A and 13B, panels i and ii show that many β-Gal+ cells were neurons and a few β-Gal+ cells were astrocytes.

Evaluation of RhoA Knockdown in B35 Neuroblastoma Cells In Vitro after Transfection with PgP-/RhoA siRNA Polyplexes.

Figure 14:
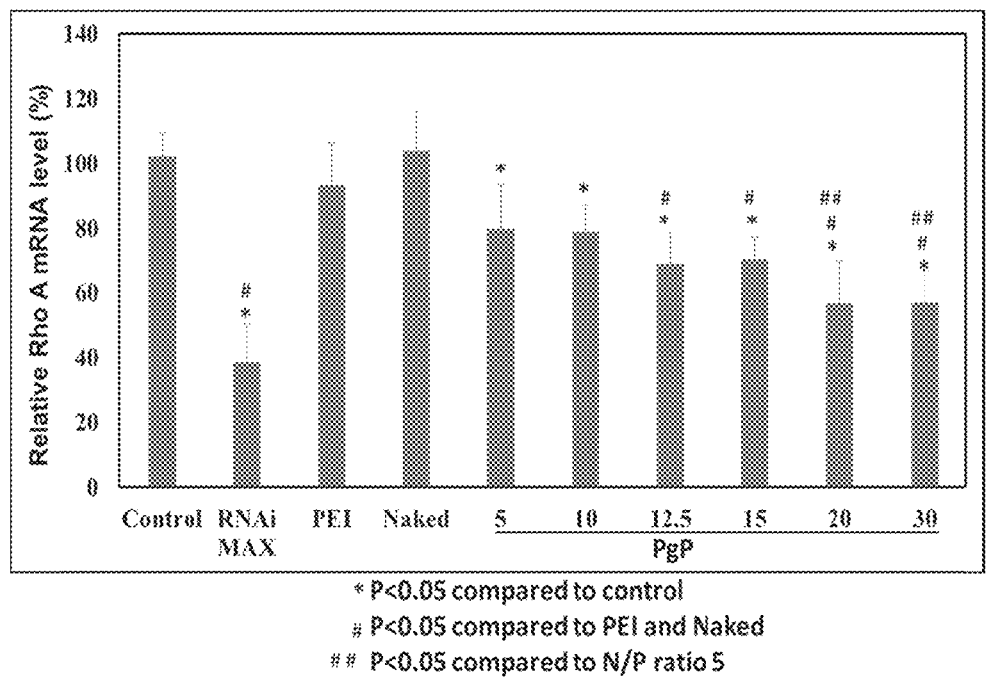
FIG. 14 shows a graph of the silencing efficiency of PgP/RhoA siRNA on B35 cells in 10% serum condition.

B35 cells were transfected with PgP/RhoA siRNA (Silencer® Select siRNAs, Life Technologies) polyplex formed at the various N/P ratios in 10% serum condition. bPEI/RhoA siRNA at an N/P ratio of 5/1, RNAiMax/RhoA siRNA, and RhoA siRNA alone were used as controls. At 48 hours post-transfection, total RNA were extracted and two-step real-time PCR was performed with target-specific primers. Relative changes in RhoA gene expression levels were analyzed by the delta-delta $C_T$ method using beta-2-microglobulin as an internal standard. Silencing efficiency increased with increasing N/P ratio and was significantly higher than that of bPEI (~7%) at all N/P ratios. The relative silencing efficiency of PgP/RhoA siRNA at N/P ratio of 30/1 was approximately 44% and it was slightly lower than that of RNAiMAX/RhoA siRNA) (~62%). FIG. 14 shows a graph of silencing efficiency of PgP/RhoA siRNA on B35 cells in 10% serum.

Intracellular Trafficking Study

Figure 15:
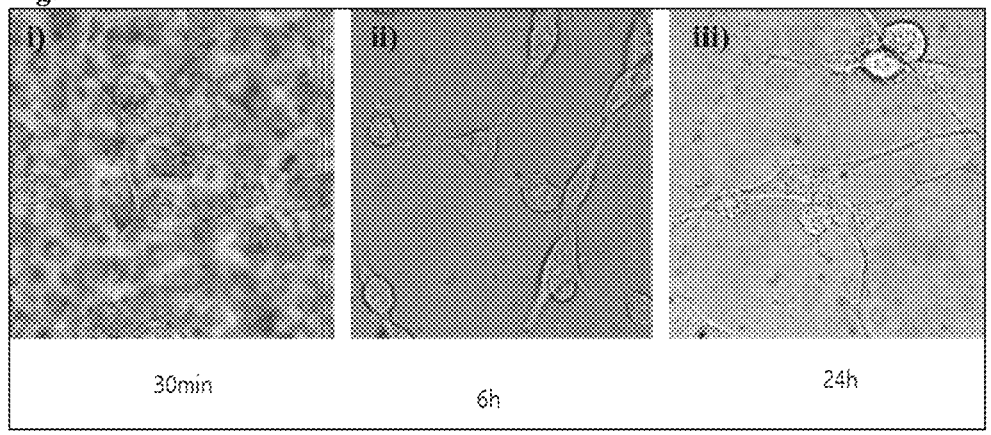
FIG. 15 shows images illustrating the intracellular trafficking of PgP/siRNA-Cy5 polyplexes at N/P ratio of 30/1 in B35 cells in 10% serum condition at 30 minutes (panel i), 6 hours (panel ii), and 24 hours (panel iii).

To evaluate the intracellular uptake of PgP/siRNA polyplexes, Cy-5 was conjugated to scrambled siRNA using Label IT siRNA Tracker Intracellular Localization Kit followed by manufacture's protocol. B35 neuroblastoma cells were incubated for 24 hrs with PgP/Cy5-siRNA (1 μg Cy5-siRNA, N/P ratio of 30/1) in 10% serum condition as described above. During incubation, B35 cells were washed, fixed, and examined by confocal laser scanning microscopy (Nikon) to analyze the uptake and intracellular distribution of PgP/Cy5-siRNA at 0.5, 2, 6, and 24 hrs. The images taken with the microscope show the PgP/Cy5-siRNA polyplexes on the cell surface at early time points (at 30 min, FIG. 15, panel i) and then in the cytosol at late time points (at 6 hrs and 24 hrs, FIG. 15, panels ii and iii, respectively) post-transfection.

Figure 16:
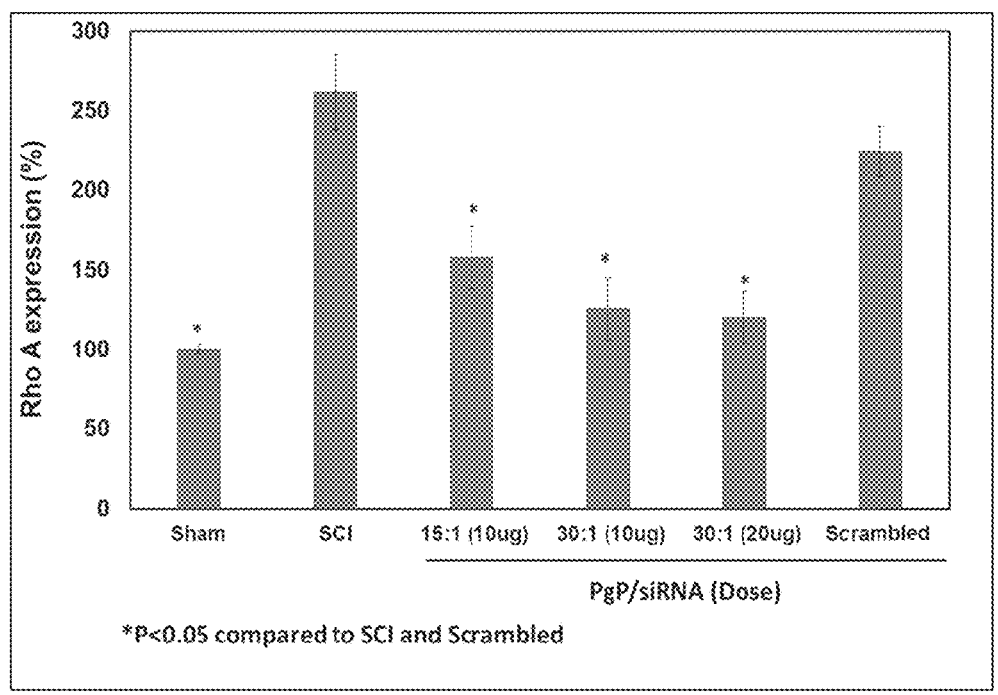
FIG. 16 shows a graph of RhoA level expression (%) in rat SCI model after local injection of PgP/RhoA siRNA in the spinal cord injury region.

Evaluation of RhoA Expression Knockdown after Injection of PgP/RhoA siRNA Polyplexes in Rat Compression Spinal Cord Injury Model In Vivo Rat compression spinal cord injury model was generated as described above and PgP/RhoA siRNA polyplex were prepared at the two different N/P ratios and two dose of siRNAs (N/P ratio (g RhoA siRNA):15/1 (10 μg), 30/1 (10 μg), and 30/1 (20 μg)) and injected into the injured dorsal T9 spinal cord using a 26-gauge Hamilton syringe. PgP/scrambled siRNA at an N/P ratio of 30/1 (10 μg siRNA), untreated SCI animal group, and sham animal group were used as controls. Following the injection, the paraspinal muscles were closed with 4-0 vicryl suture, and the skin was closed with 3-0 silk suture. At 7 days after polyplex injection, the spinal cord (0.5 cm-long piece from the center of the injury) was retrieved. Total RNA was extracted and two-step real-time PCR were performed with target-specific primers. Relative changes in RhoA gene expression levels were analyzed by the delta-delta $C_T$ method using beta-2-microglobulin as an internal standard. RhoA gene expression in untreated SCI animal group was increased 2.61-fold at 7 days. However, the RhoA gene knockdown was achieved in all PgP/RhoA siRNA injected animal groups compared to untreated SCI animal group and the order of RhoA gene suppression was 30/1 (20 μg)>30/1 (10 μg)>15/1 (10 μg). FIG. 16 shows a graph of RhoA expression in rat SCI model after injection of PgP/RhoA siRNA.

Rolipram (Rm) Loading Efficiency

Figure 17:
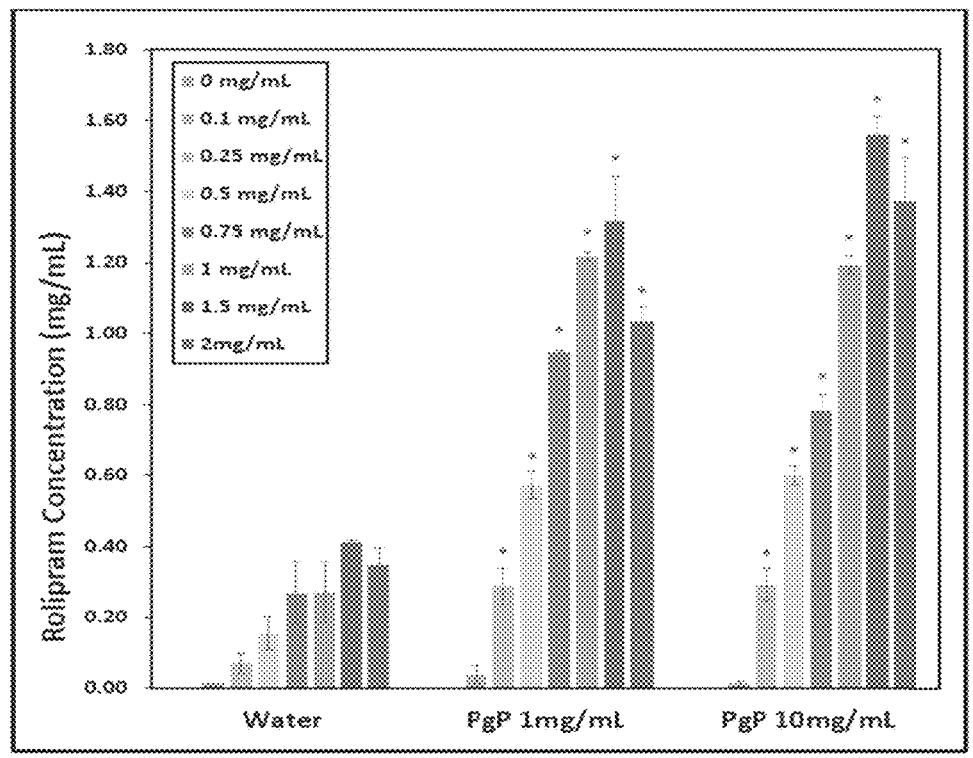
FIG. 17 shows a graph of Rolipram (Rm) loading efficiency for water, PgP 1 mg/mL, and PgP 10 mg/mL (Rolipram concentration (mg/mL) for the bars from right to left for each of water, PgP 1 mg/mL, and PgP 10 mg/mL are 2 mg/mL, 1.5 mg/mL, 1 mg/mL, 0.75 mg/mL, 0.5 mg/mL, 0.25 mg/mL, 0.1 mg/mL, and 0 mg/mL).

To evaluate the rolipram loading efficiency, various PgP (1 mg and 10 mg of PgP/1 ml) particles were prepared. Varying amount of rolipram was dissolved in ethanol and then added in PgP solutions and incubated overnight to allow the ethanol evaporation. The amount of rolipram in PgP solution was measured by HPLC (Waters System) using a Waters Symmetry C18 column with mobile phase water: acetonitrile (60:40). The rolipram loading efficiency of PgP was calculated as follows. % Loading efficiency=(Amount of Rolipram loaded/amount of Rolipram added)×100. FIG. 17 shows a graph of rolipram loading efficiency. The amount of loaded rolipram in PgP increased with the length of hydrophobic polymer core in PgP and the order of % Rm loading efficiency was PgP-50k>PgP-25>PgP-12k.

Figure 18:
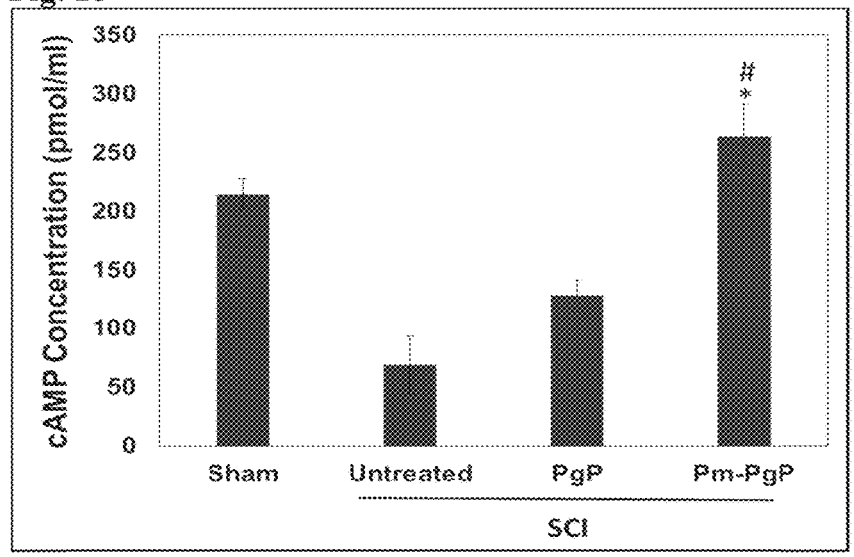
FIG. 18 shows a graph of cAMP level in spinal cord at 1 day after local injection of Rm-PgP in the SCI region (n=6).

Evaluation of cAMP Level in Injured Spinal Cord after Local Injection of Rm-PgP:

Rm-PgP (1 mg of rolipram/1 ml PgP (1 mg/ml)) were prepared by solvent evaporation method described above. 10 ul of Rm-PgP were injected at the injury site after SCI. PgP alone, injury only, and sham animal group were used as controls. At 1 day after injection, the spinal cord 8 mm rostral and 8 mm caudal to the lesion site will be rapidly dissected at 4° C. and frozen in liquid nitrogen. Tissue will be briefly sonicated on ice in 20 volumes of 0.1 N HCl and 500 μM 3-isobutyl-1-methylxanthine (IBMX). The level of cAMP will be quantified by ELISA assay (R & D system). It was observed that cAMP level was restored to Sham animal group in Rm-PgP treated group while cAMP level was dramatically decreased in untreated SCI animal group (FIG. 18).

Loading of Hydrophobic DIR Dye in PgP (DiR-PgP)

To evaluate the retention of locally injected PgP and biodistribution of PgP nanoparticle after systemic injection, 50 ug of DIR (1,1'-Dioctadecyl-3,3,3',3'-Tetramethylindotricarbocyanine Iodide) was dissolved in 100 ul acetone and added in 1 ml PgP (1 mg/ml) solution and 1 ml water, respectively and incubated overnight to allow the acetone evaporation. To remove the undissolved DIR, the solutions were filtered by syringe filter (0.25 um). In case of PgP solution, the hydrophobic dye, DIR was dissolved in the PgP and showed green color, while DIR was not dissolved in water and removed by filtration. This demonstrated that the hydrophobic drug can be loaded in hydrophobic core of PgP micelle.

Figure 19:
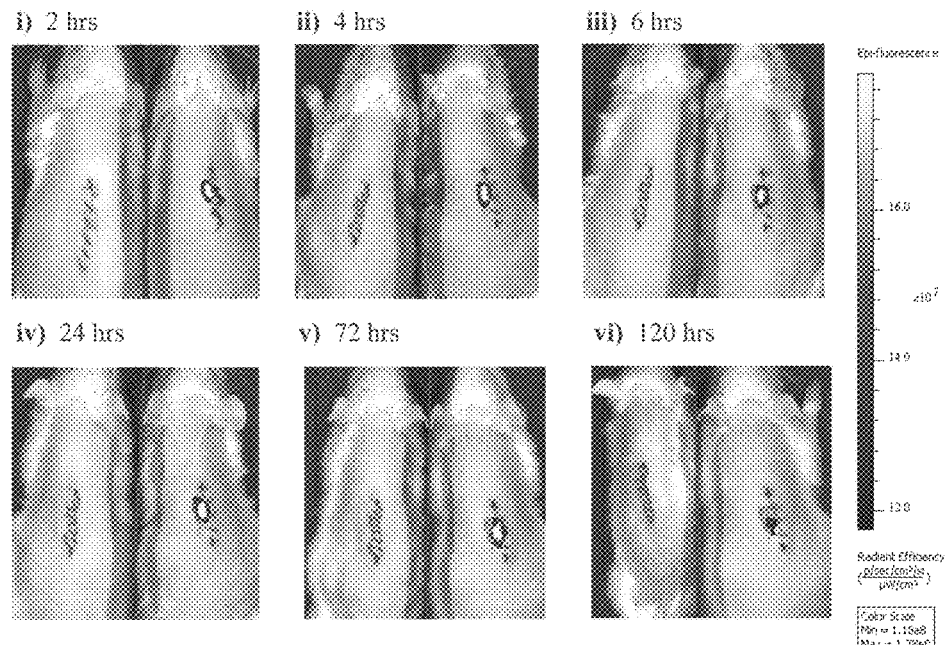
FIG. 19 shows images from live animal fluorescence imaging for Sprague Dawley rats (70-100 gm) after local injection of DIR-PgP/pDNA (10 µg pDNA/rat) at 2 hrs (panel i), 4 hrs (panel ii), 6 hrs (panel iii), 24 hrs (panel iv), 72 hrs (panel v), and 120 hrs (panel vi).

Biodistribution of DIR-PgP/pDNA after Local and Systemic Injection in Rat Spinal Cord Injury Model Rat compression spinal cord injury model was generated as described previously. DIR-PgP/pDNA polyplexes (N/P ratio of 30/1, 10 μg pDNA/rat) were prepared as described above and locally injected in the T9 spinal cord injury lesion by Hamilton syringe. Localization and retention of DIR-PgP/pDNA polyplex were assessed immediately following injection by live animal fluorescence imaging system (Quantum FX microCT Imaging System, PerkinElmer). At a predetermined time point, the animals were sacrificed and the spinal cord was retrieved and the retention of DIR-PgP/pDNA polyplex were also assessed by live animal fluorescence imaging system ex vivo. DIR-PgP/pDNA polyplexes were retained at the injection site up to 5 days (FIG. 19). FIG. 19 shows images from live animal fluorescence imaging for Sprague Dawley rats (70-100 gm) after local injection of DIR-PgP/pDNA (10 μg pDNA/rat) at 2 hrs (panel i), 4 hrs (panel ii), 6 hrs (panel iii), 24 hrs (panel iv), 72 hrs (panel v), and 120 hrs (panel vi).

Figure 20:
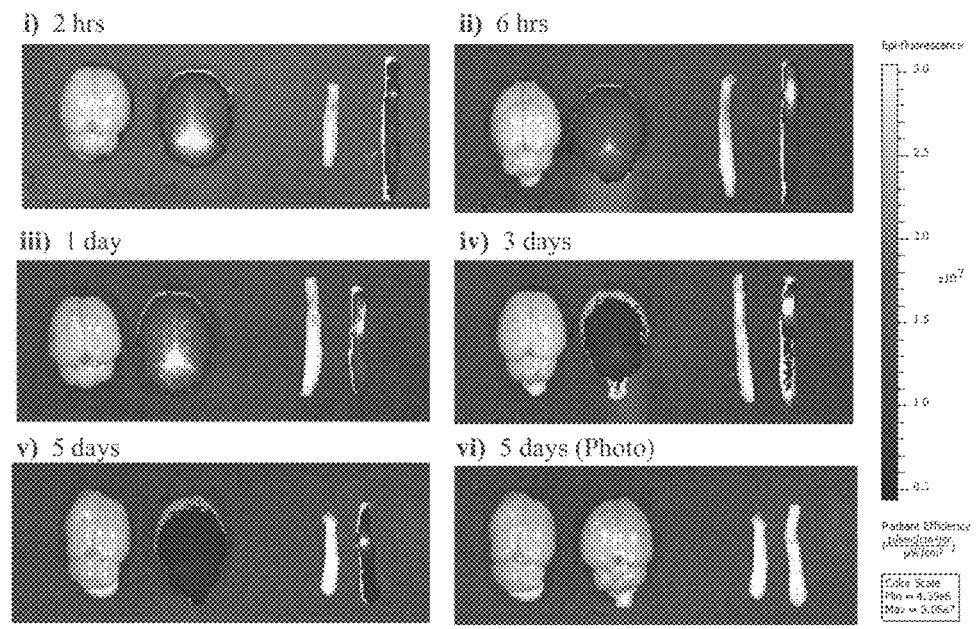
FIG. 20 shows images of brain and spinal cord retrieved from Sprague Dawley rats (70-100 gm) after local injection DIR-PgP/pDNA (10 µg pDNA/rat) at 2 hrs (panel i), 6 hrs (panel ii), 1 day (panel iii), 3 days (panel iv), 5 days (panel v), and 5 days (photo, panel vi).
Figure 21A:
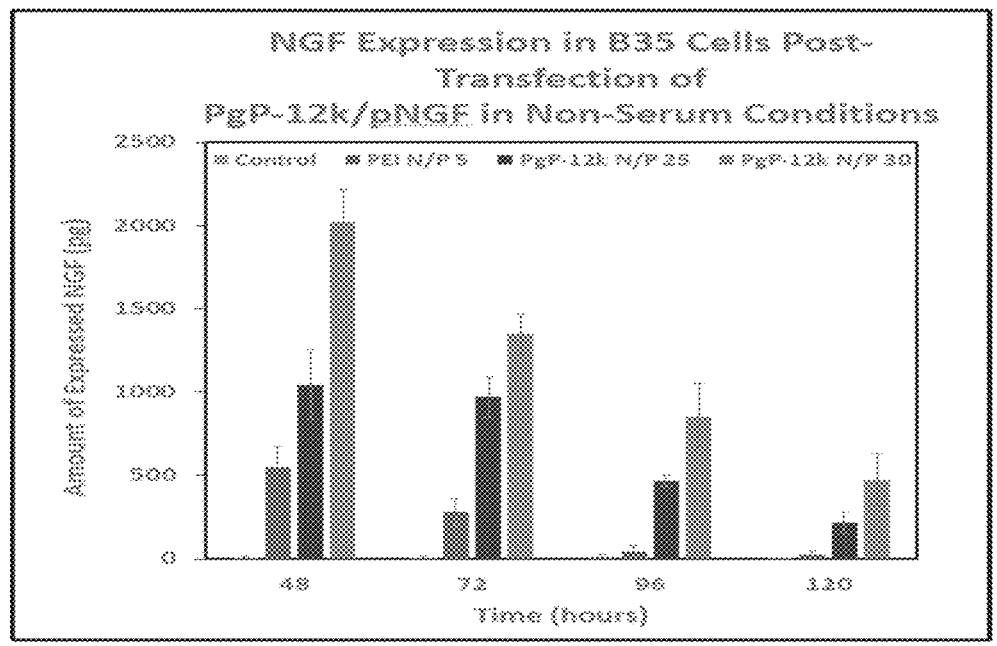
FIG. 21A shows a graph of the amount of NGF expression (pg/ml) over 120 hours transfecting with PgP12k/pBLAST44-hNGF complexes in B35 cells using non-serum conditions. Bars from right to left for each of time point are: PgP-12k N/P 30, PgP-12k N/P 25, PEI N/P 5, and control.
Figure 21B:
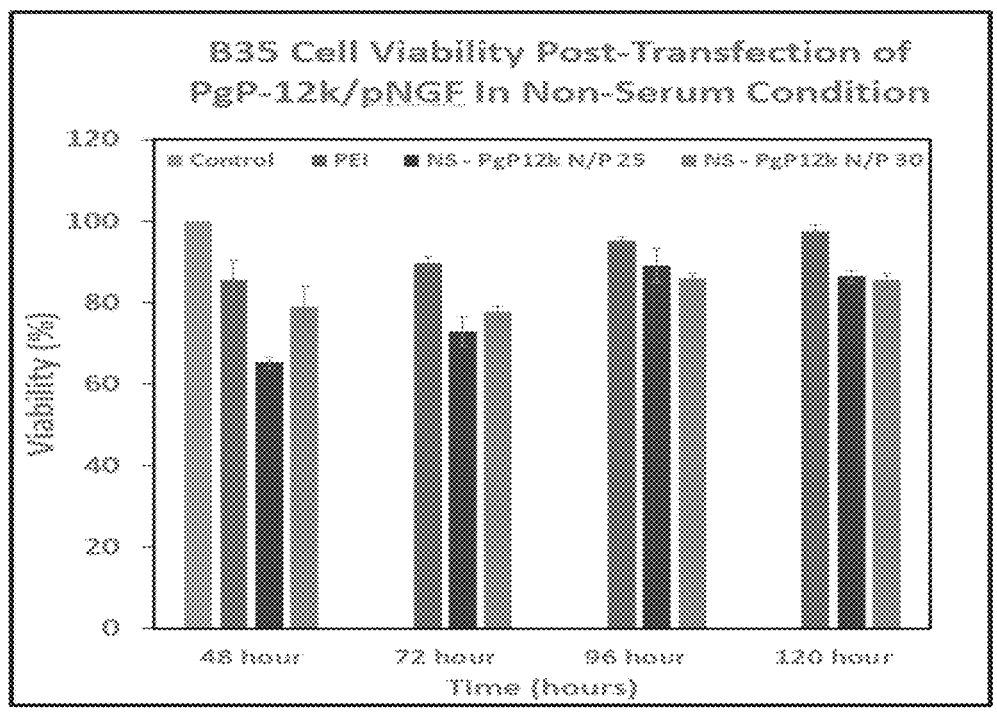
FIG. 21B shows a graph of the percent cell viability over 120 hours transfecting with PgP12k/pBLAST44-hNGF complexes in B35 cells using non-serum conditions. Bars from right to left for each of time point are: PgP-12k N/P 30, PgP-12k N/P 25, PEI, and control.
Figure 21C:
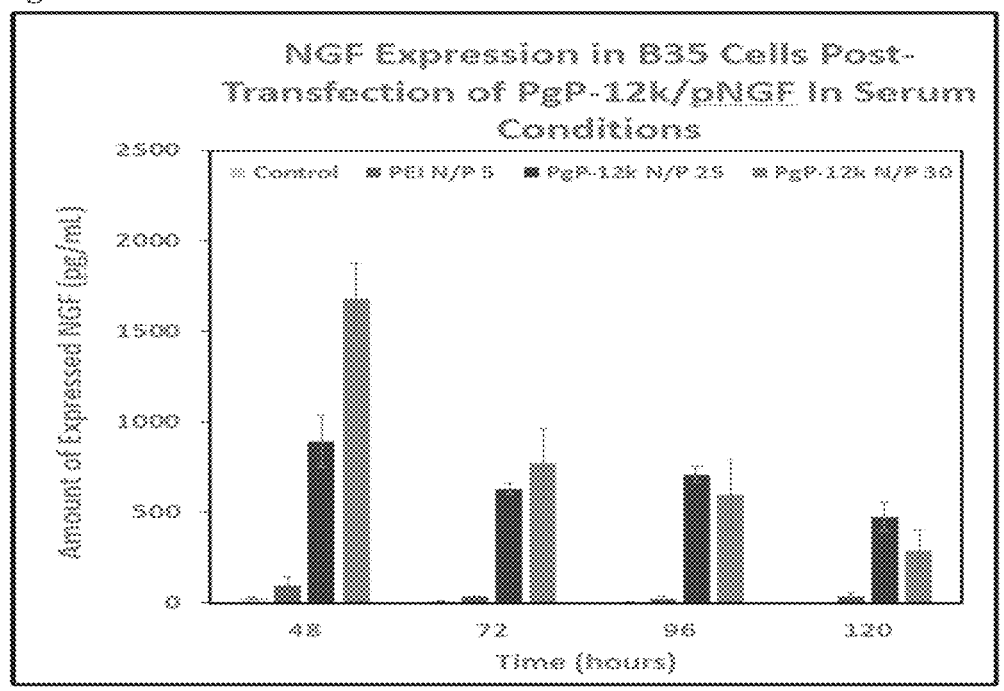
FIG. 21C shows a graph of the amount of NGF expression (pg/mL) over 120 hours transfecting with PgP12k/pBLAST44-hNGF complexes in B35 cells using 10% FBS conditions. Bars from right to left for each of time point are: PgP-12k N/P 30, PgP-12k N/P 25, PEI N/P 5, and control.
Figure 21D:
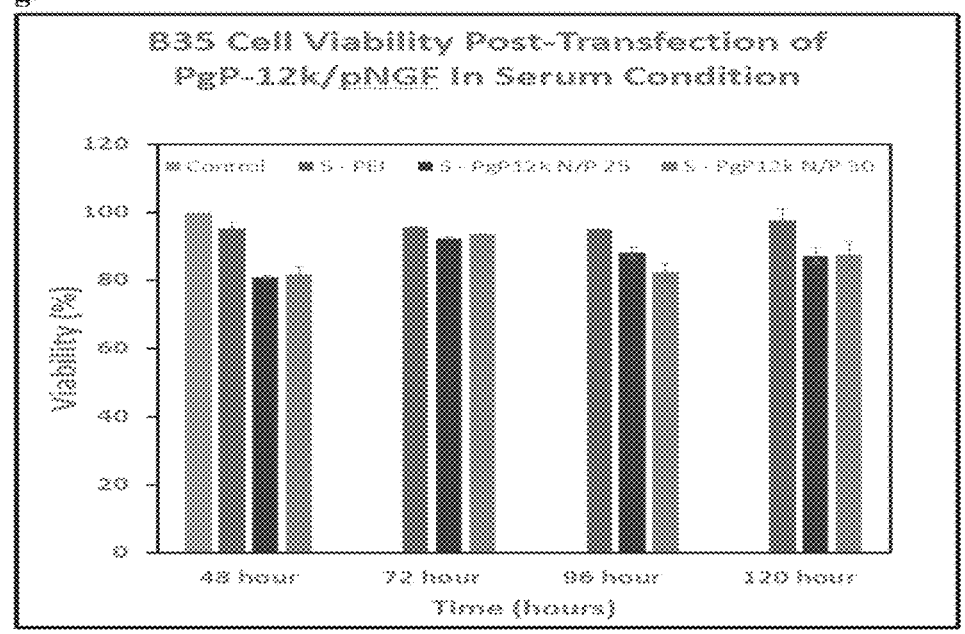
FIG. 21D shows a graph of the percent cell viability over 120 hours transfecting with PgP12k/pBLAST44-hNGF complexes in B35 cells using 10% FBS conditions. Bars from right to left for each of time point are: PgP-12k N/P 30, PgP-12k N/P 25, PEI, and control.
Figure 22A:
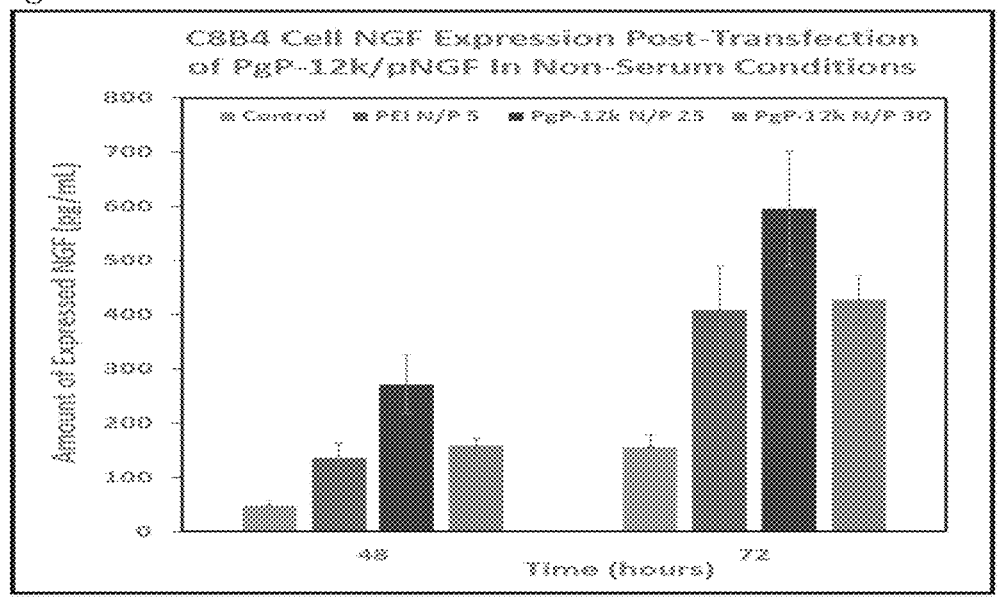
FIG. 22A shows a graph of the amount of NGF expression (pg/ml) over 72 hours transfecting with PgP12k/pBLAST44-hNGF complexes in C8-B4 (microglia) cells using non-serum conditions. Bars from right to left for each of time point are: PgP-12k N/P 30, PgP-12k N/P 25, PEI N/P 5, and control.
Figure 22B:
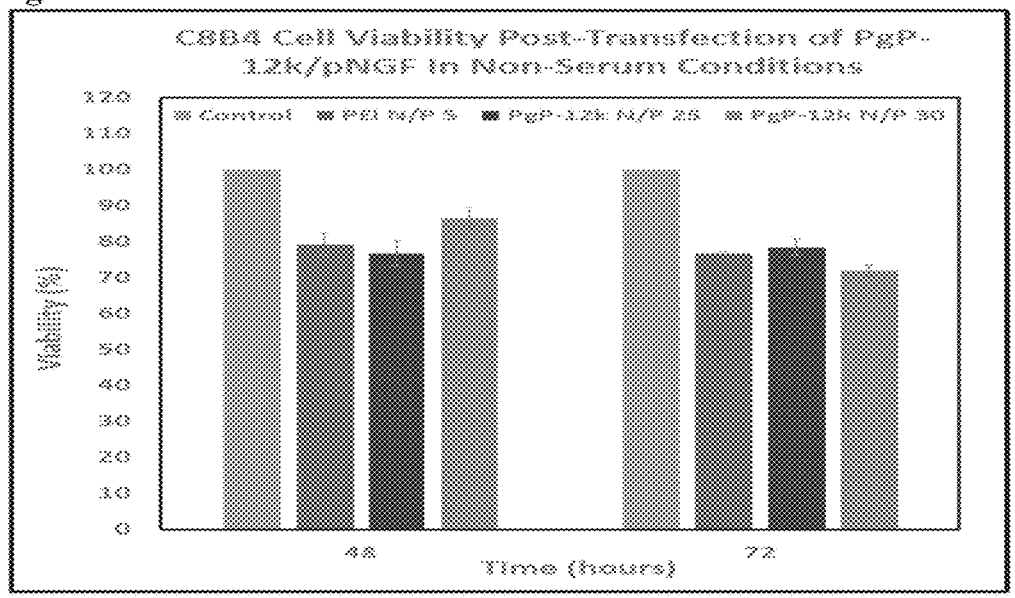
FIG. 22B shows a graph of the percent cell viability over 72 hours transfecting with PgP12k/pBLAST44-hNGF complexes in C8-B4 cells using non-serum conditions. Bars from right to left for each of time point are: PgP-12k N/P 30, PgP-12k N/P 25, PEI N/P 5, and control.
Figure 22C:
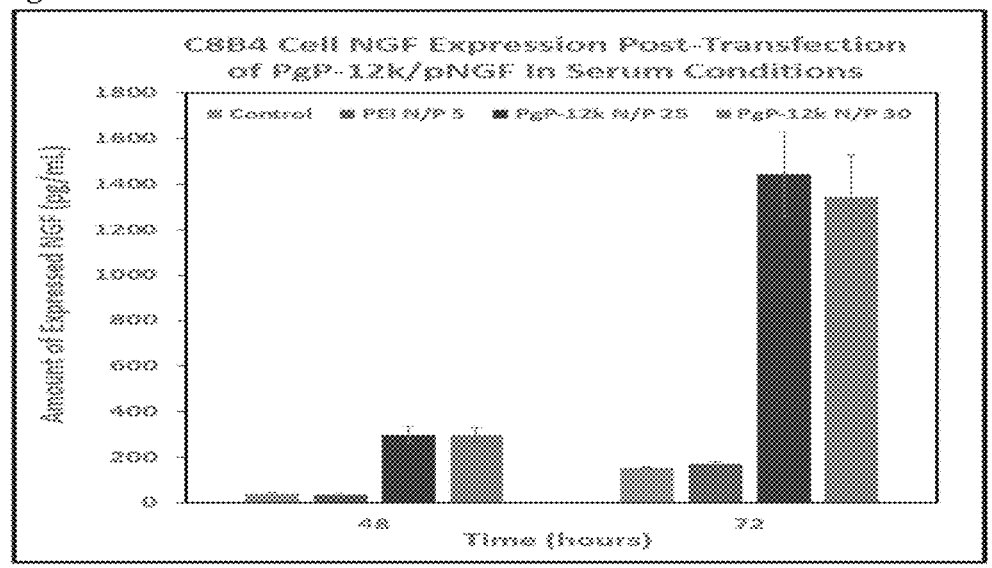
FIG. 22C shows a graph of the amount of NGF expression (pg/mL) over 72 hours transfecting with PgP12k/pBLAST44-hNGF complexes in C8-B4 cells using 10% FBS conditions. Bars from right to left for each of time point are: PgP-12k N/P 30, PgP-12k N/P 25, PEI N/P 5, and control.
Figure 22D:
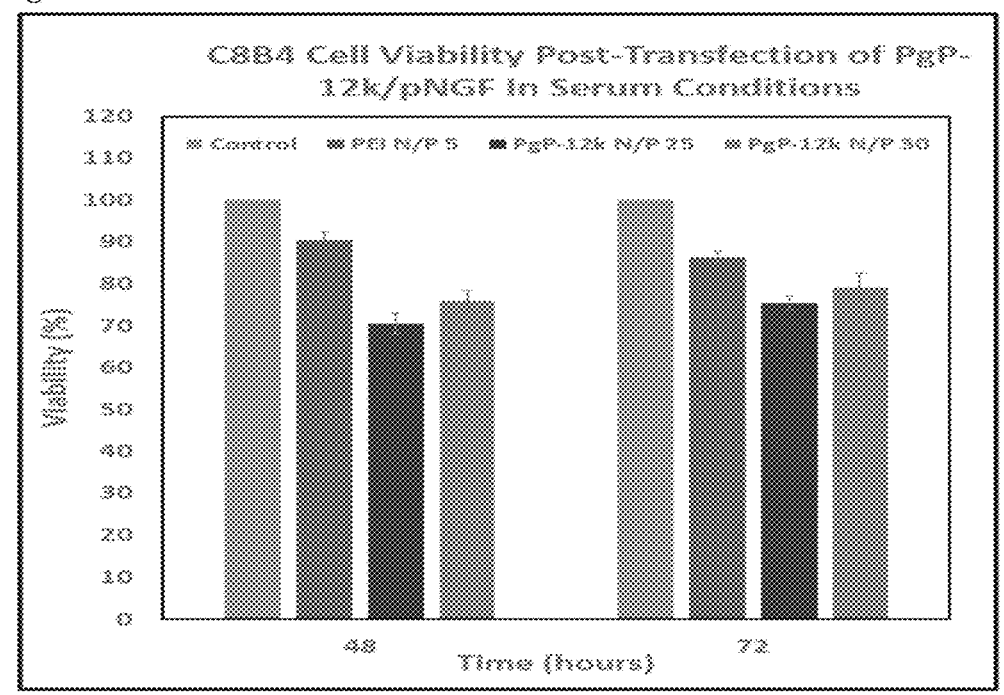
FIG. 22D shows a graph of the percent cell viability over 72 hours transfecting with PgP12k/pBLAST44-hNGF complexes in C8-B4 cells using 10% FBS conditions. Bars from right to left for each of time point are: PgP-12k N/P 30, PgP-12k N/P 25, PEI N/P 5, and control.

Rat compression spinal cord injury model was generated as described previously and DIR-PgP/pDNA polyplexes (N/P ratio of 30/1, 500 µg pDNA/rat) were prepared as described above and injected by tail vein. The biodistribution of DIR-PgP/pDNA polyplex were assessed immediately following injection by live animal fluorescence imaging system (Quantum FX microCT Imaging System, PerkinElmer). At a predetermined time point, the animals were sacrificed and the organs were retrieved and the distribution of DIR-PgP/pDNA polyplex were also assessed by live animal fluorescence imaging system ex vivo. DIR-PgP/pDNA polyplexes were distributed in the brain and spinal cord and detected up to 5 days (FIG. 20). FIG. 20 shows images of retrieved brain and spinal cord from Sprague Dawley rats (70-100 gm) after local injection of DIR-PgP/pDNA (10 µg pDNA/rat) at 2 hrs (panel i), 6 hrs (panel ii), 1 day (panel iii), 3 days (panel iv), 5 days (panel v), and 5 days (photo, panel vi).

Evaluate cAMP Level and Neurite Outgrowth in Cortical Neurons Exposed to In Vitro Hypoxia Condition after Transfection with Rm-PgP.

To generate hypoxia condition as a SCI model in vitro, rat primary cerebellar neurons (CBN) were isolated from P3 pubs and plated on the PLL/Laminin coated well plate. After 3 days culture, the cells were incubated in hypoxia gas chamber (95% N2 and 5% O2) for 24 hours and then the cells were treated with Rm-PgP and PgP without rolipram. Cells treated with free rolipram dissolved in DMSO were used as a positive control and cells maintained under normal atmospheric conditions were used as a negative control. The cells were incubated an additional 24 hrs in hypoxia condition and then fixed for neurite length evaluation. The neurite lengths were measured using ImageJ software program after 3-3 tubulin staining. Neurite length of CBN cells cultured in hypoxia condition was significantly different with the neurite length of CBN cells cultured in normoxia condition, while neurite length of CBN cells in normoxia were not significantly different in free Rm in DMSO, Rm-loaded PgP, and PgP only group. It was also observed that neurite length in the group treated with PgP alone (no Rm) was also significantly higher than the hypoxia group. This result helps confirm the cytocompatibility of the delivery carrier.

Example 3

Traumatic brain injury (TBI) represents one of the leading causes of disability and death following injury with an estimated 2.5 to 6.5 million patients suffering from long term effects 1. The presentation of TBI involves both a primary and a secondary injury. The primary injury is a direct result of the traumatic event, and is closely followed by inflammatory response. The progression of inflammatory response is marked by the increased production of various cytokines acting in either neuroprotective or neurotoxic roles. Several key neurotoxic cytokines are inhibited by physiologically normal levels of cyclic adenosine monophosphate (cAMP). Rolipram, a hydrophobic drug used in treatment of traumatic CNS injury, prevents the degradation of cAMP and is able to inhibit production of potentially neurotoxic cytokines. Additional treatment for TBI is the administration of exogenous nerve growth factor (NGF), which has shown neuroprotective function and can reduce edema following primary injury. For simultaneous delivery of rolipram and pNGF, amphiphilic copolymers composed of poly(lactide-co-glycolide)-g-polyethylenimine (PgP) were designed. Here, the rolipram loading efficiency and transfection efficiency and duration of PgP/pNGF polyplexes in B-35 neuroblastoma cells is presented.

Transfection of PgP/pBLAST44-hNGF Complexes in Neuroblastoma Cells and Immortalized Microglia:

PgP/pNGF complexes (2 µg pNGF/well) were prepared at two N/P (No. of nitrogen/No. of phosphate) ratios of 25/1 and 30/1 selected according to past data3. pBLAST44-hNGF: NGFB (InvivoGen). Transfection conditions: B35 (neuroblastoma) cells and C8-B4 (microglia) cells were transfected in media containing and void of 10% FBS. The FBS negative condition was allowed to incubate at 37° C. for 4 hrs and the 10% FBS condition for 24 hrs; at which time media was replaced. Data acquisition occurred 48 hours post transfection. Transfection Efficiency—measured by ELISA assay using Human beta-NGF DuoSet kit (R&D Systems). Cytotoxicity was analyzed by MTT assay. The formazan crystals formed by live cells were dissolved in DMSO and absorbance was measured at 570 nm. % Cell Viability=(OD570 (sample)/OD 570 (control))*100

Loading of Rolipram Through Evaporative Method:

Three different molecular weights of PgP were dissolved at 1 and 10 mg/mL in water. Rolipram stock solution prepared in ethanol at 20 mg/mL and then serial diluted. 50 uL of Rolipram stock was added to 500 uL of PgP solution. Following 6 hours incubation, ethanol was evaporated overnight. Rolipram content was evaluated with Waters HPLC.

Transfection of PgP12k/pBLAST44-hNGF polyplexes achieved increased NGF expression over PEI controls in both B35 neuroblastoma cells and C8-B4 microglia (FIGS. 21A-21D and FIGS. 22A-22D). With both N/P ratio 25/1 and 30/1 there was not significant loss in cell viability for either cell line. Transfection of PgP12k/pBLAST44-hNGF polyplexes at N/P ratio of 30/1 resulted in the highest level of NGF expression in B35 cells, however the N/P ratio 25/1 achieved slightly higher expression in C8-B4 cells.

The loading of Rolipram in PgP-12k achieved higher concentrations of Rolipram solubilized in aqueous environment. The efficiency of this loading per amount of Rolipram added to solution was highest (86%) in a 1 mg/mL PgP-12k solution (FIG. 17). While not wishing to be bound to any particular theory, the observed decrease in loading ability of a 10 mg/mL PgP-12k solution could result from the increased amount of hydrophilic groups present in a more concentrated PgP-12k solution.

It is demonstrated that PgP/pBLAST44-hNGF polyplexes can successfully transfect expression of NGF in both B35 and C8-B4 cells without significant loss in cell viability. The PgP polymer also demonstrated the ability to increase the solubility of the hydrophobic drug Rolipram in water and presented a four-fold increase in solubility.

Example 4

Primary tumors centralized to the brain and spinal cord are among the most difficult to treat due to the fragile nature of the surrounding tissue. This issue is compounded by the introduction of drug resistant lines, such as glioblastoma, and leads to low survival amongst the diagnosed. Temozolomide (TMZ), a DNA alkylating drug, is commonly used to treat glioblastoma (GBM), but is rendered ineffective against the drug resistant lines by the overexpression of O-6-methlygunaine-DNA methyl transferase (MGMT), a DNA repair protein1. Small interfering RNAs (siRNAs) have been investigated as a precursor treatment for drug resistant cancers because of their ability to down regulate their target protein by preventing translation. The approach is to develop polymeric micelle as a dual delivery carrier for treatment of GBM. Amphiphilic copolymer poly (lactide-co-glycolide)-g-polyethylenimine (PgP) was synthesized and characterized. The synthesis and evaluation of the amphiphilic co-polymer, poly (lactide-co-glycolide)-graft-polyethylenimine (PLGA-g-PEI:PgP) is described above, as a nucleic acid carrier using pGFP in C6 (glioblastoma) cells and primary chick forebrain neuron cells. Here, the feasibility of PgP as a nucleic acid delivery carrier using pGFP and siGLO® transfection indicator in B35 (Rat neuroblastoma) cells and T98G (Human Glioblastoma) cells in both 10% serum condition and non-serum condition in vitro is demonstrated.

Methods:

PgP/pGFP complexes (2 μg pGFP) and PgP/siGLO® complexes (0.5 and 1 μg siGLO®) were prepared at different N/P (No. of nitrogen/No. of phosphate) ratios ranging from 5/1 to 30/1, respectively. (PgP: poly (lactide-co-glycolide)-g-polyethylenimine was synthesized and characterized in 4D Lab. (pGFP: MonsterGreen Fluorescent Protein phMGFP Vector (Promega). siGLO®: Red transfection indicator (Thermo Fisher Scientific). Transfection in 10% serum condition: (B35 and T98G cells were transfected in media containing 10% FBS and allowed to incubate at 37° C. for 24 hrs; at which time media was replaced. (Transfection in non-serum condition: (B35 and T98G cells were transfected in media containing no FBS and allowed to incubate at 37° C. for 4 hrs; at which time media was replaced. Transfection efficiency was measured at 48 hours by flow cytometry using a Millipore easyCyte flow cytometer with guavaCyte software Cytotoxicity was analyzed by MTT assay at 48 hours. The formazan crystals formed by live cells were dissolved in DMSO and absorbance was measured at 570 nm. % Cell Viability=(OD570 (sample)/OD 570 (control))*100

Figure 23:
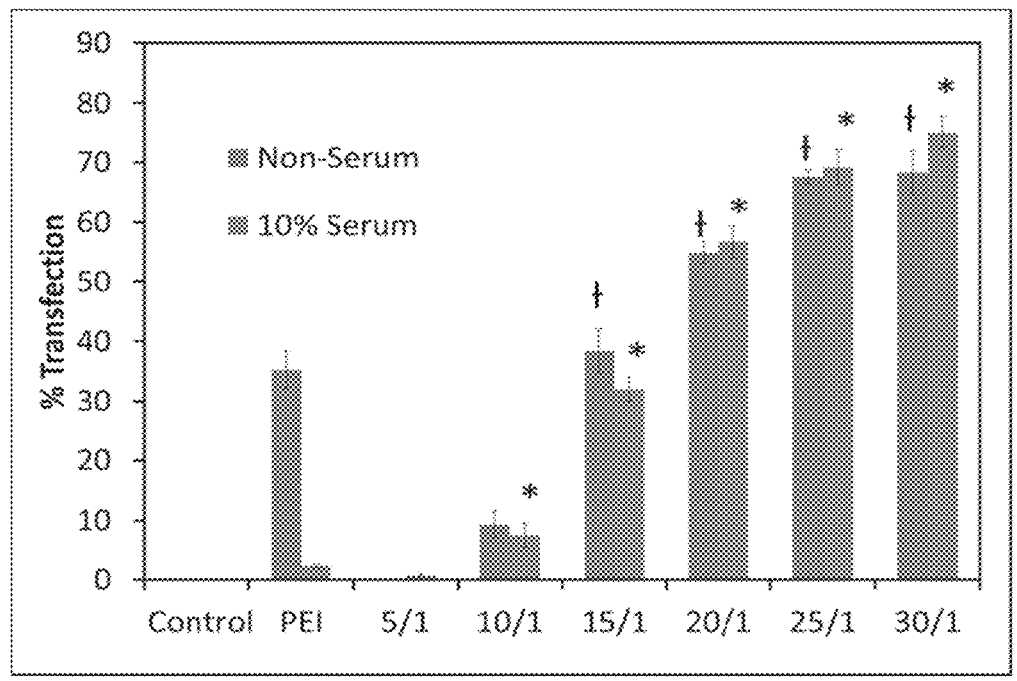
FIG. 23 shows a graph of the percent of transfection in B35 cells PEI at N/P Ratio 5/1; PgP12K/pGFP at N/P ratios shown; SEM shown, n=6. Bars for each complex: left=non-serum; right=10% serum.
Figure 24A:
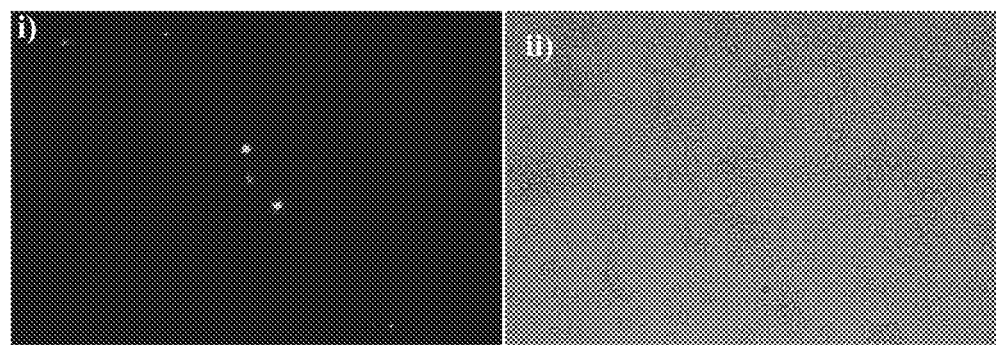
FIG. 24A shows images of PEI/pGFP 5/1 transfection of B35 (Neuroblastoma) cells (40×) in 10% serum conditions through fluorescent microscopy (panel i) and phase contrast microscopy (panel ii).
Figure 24B:
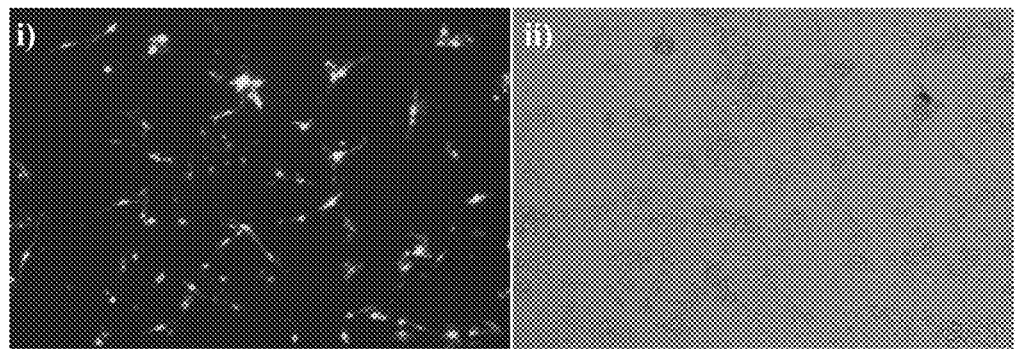
FIG. 24B shows images of PgP12K/pGFP 30/1 transfection of B35 cells (40×) in 10% serum conditions through fluorescent microscopy (panel i) and phase contrast microscopy (panel ii).
Figure 25:
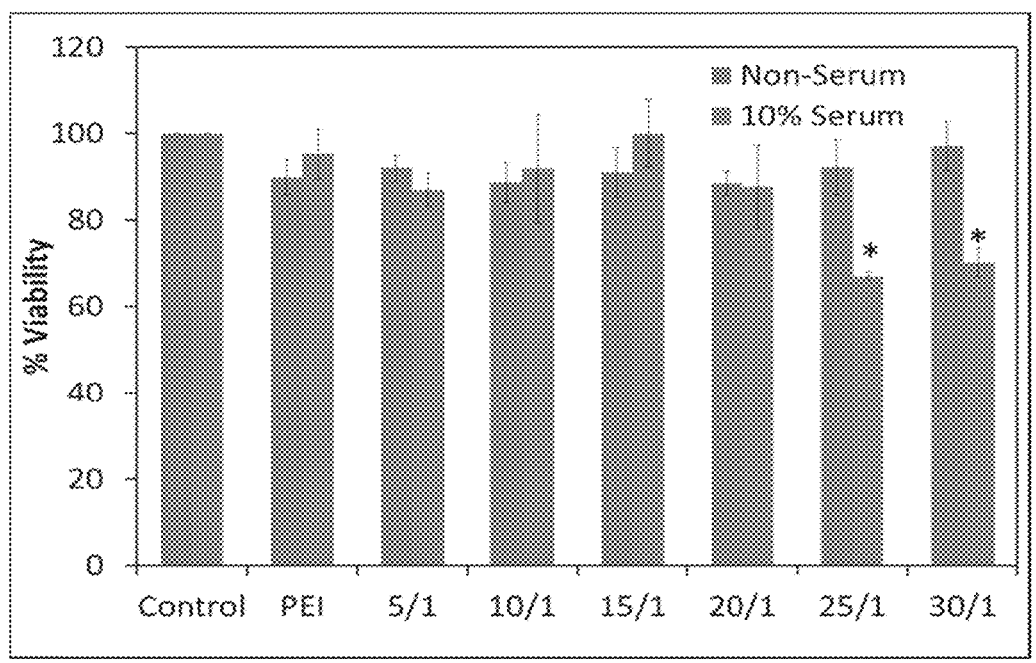
FIG. 25 shows a graph on the cytotoxicity in B35 cells PEI at N/P Ratio 5/1; PgP12K/pGFP at N/P ratios shown; SEM shown, n=6. Bars for each complex: left=non-serum; right=10% serum.

In 10% Serum Condition, PgP-12K transfect pGFP significantly better than PEI does (FIG. 23). This is best demonstrated in FIGS. 24A and 24B as cells transfected with PgP-12K at N/P 30/1 (FIG. 24B, panel i (fluorescence) and panel ii (phase contrast)) show high fluorescence while those transfected with PEI at N/P 5/1 (FIG. 24A, panel i (fluorescence) and panel ii (phase contrast)) show minimal fluorescence. Transfection percentage increase with increasing N/P ratio in the cells exposed to PgP-12K/pGFP complexes and aside from the highest N/P ratio transfections, PgP-12K shows minimal cytotoxicity despite the increasing polymer load (FIG. 25). PgP-12K is effective in delivering pGFP in both serum and non-serum conditions unlike PEI which is only effective in non-serum conditions (FIG. 23).

Figure 26A:
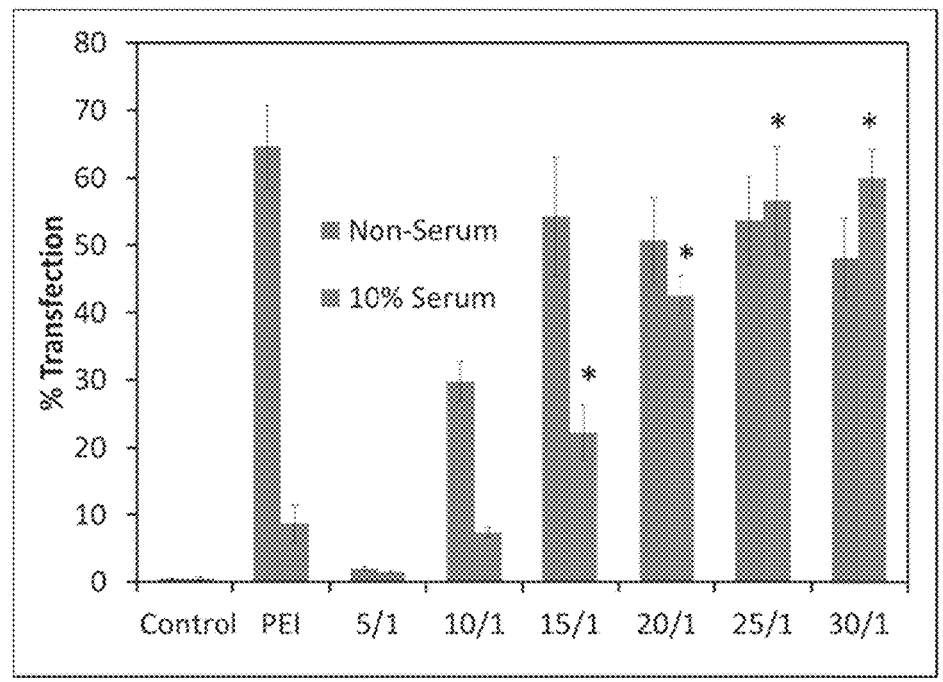
FIG. 26A shows a graph of the percent transfection in T98G (Glioblastoma) cells PEI at N/P Ratio 5/1; PgP12K/pGFP at N/P ratios shown; SEM shown, n=6. Bars for each complex: left=non-serum; right=10% serum.
Figure 26B:
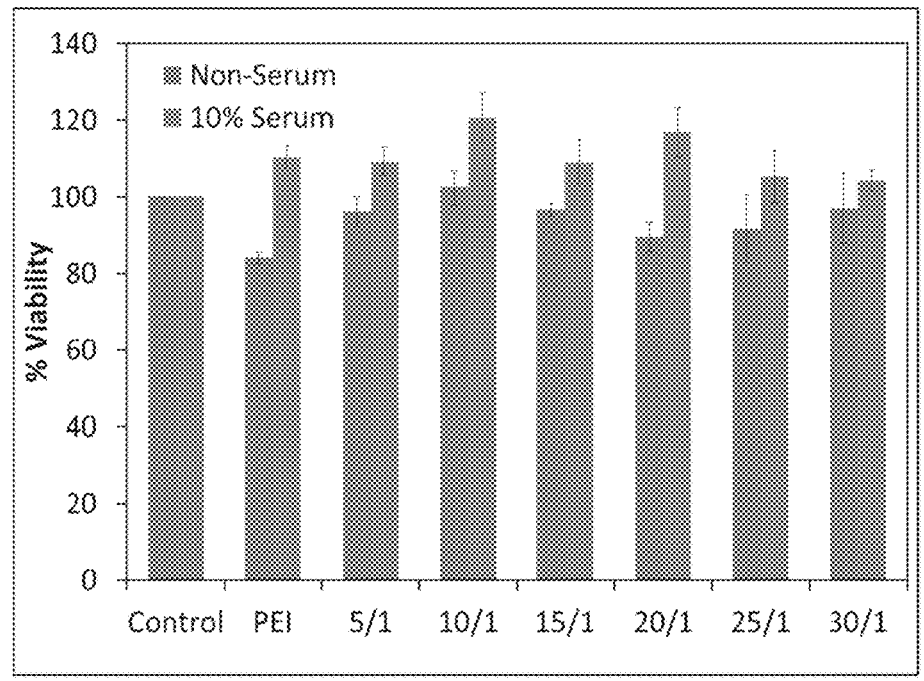
FIG. 26B shows a graph on the cytotoxicity in T98G cells PEI at N/P Ratio 5/1; PgP12K/pGFP at N/P ratios shown; SEM shown, n=6. Bars for each complex: left=non-serum; right=10% serum.
Figure 27A:
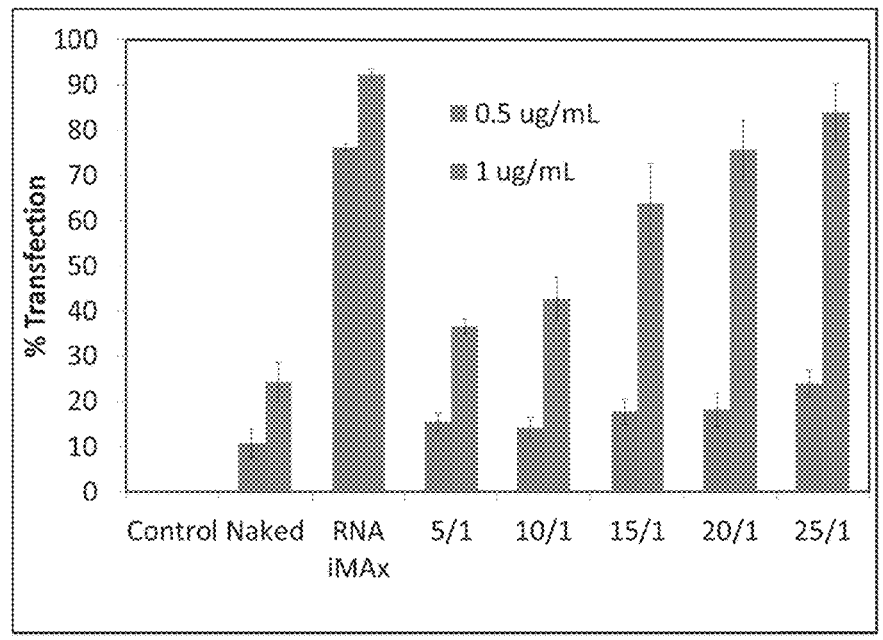
FIG. 27A shows a graph of the percent transfection in B35 cells PgP12K/siGLO at N/P ratios shown; SEM shown, n=6. Bars for each complex: left=0.5 µg/mL; right=1 µg/mL.
Figure 27B:
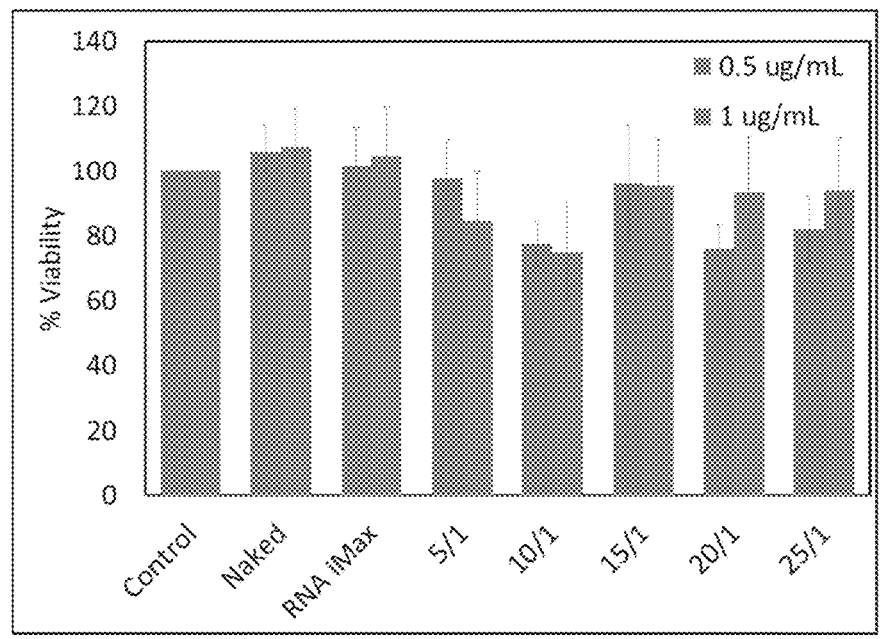
FIG. 27B shows a graph on the cytotoxicity in B35 cells PgP12K/siGLO at N/P ratios shown; SEM shown, n=6. Bars for each complex: left=0.5 µg/mL; right=1 µg/mL.

The T98G cells show a similar trend to B35 in that percent transfection increases as the N/P increases (FIG. 26A). However, there is no drop off in viability as the amount of polymer increases (FIG. 26B). siGLO transfection increased in experiments with using 1 μg siGLO (FIG. 27A) and shows minimal cytotoxicity (FIG. 27B) across all 1 μg siGLO transfection.

PgP shows promise as carrier for plasmid DNA to multiple brain cancer lines (B35, T98G). It shows significant improvement in transfection compared to PEI in a 10% serum condition, and shows consistent transfection across both 10% serum and non-serum conditions.

Future work may involve the use of PgP as a carrier for MGMT siRNA and the loading of Temozolomide into PgP with the eventual goal of simultaneously delivering MGMT siRNA and TMZ to brain cancer cells.

Example 5

A polymeric micelle delivery system was developed that combines targeted chemical drug delivery with siRNA directed towards overcoming drug resistance a treatment for drug resistant cancers. This multi-functional polymeric nanoparticle system consists of three components, 1) amphiphilic copolymers, poly(lactide-co-glycolide)-g-polyethylenimine (PgP), 2) therapeutics, including anticancer drug and siRNA targeted to PgP, and 3) tumor-specific targeting moiety such as an antibody, folic acid, or transferrin. It is demonstrated that PgP is an efficient nucleic acid carrier for both pGFP and siGLO® in breast cancer cells (MCF-7, MDA-MB468, MDA-MB 435 WT, and MDA-MB 435 ADR cells). This system addresses multiple drug resistance as it has exhibited the ability to deliver genetic agents that result in protein downregulation. Further studies include addition of a targeting moiety (Folic acid) to deliver anticancer drug and siRNA targeting P-gP for the efficient treatment of drug resistant cancer.

Cell Culture Conditions:

All cells were grown in their respective media supplemented with 10% FBS and 100 IU/ml penicillin/100 ug/ml streptomycin at 37° C. under 5% $CO_2$. Cell media conditions were as follows: MCF-7, EMEM supplemented with 10 ug/mL insulin, MDA-MB-468, DMEM, MDA-MB-435 (WT) and MDA-MB-435 (ADR), RPMI 1640; drug resistance was maintained by treating cells with 0.2 ug/mL of Doxorubicin containing media a minimum of once a week.

Transfection Efficiency and Cytotoxicity of PgP/Nucleic Acids in Human Breast Cancer Cells:

The transfection efficiency of PgP/nucleic acid particles was examined in various breast cancer cells (i.e., MCF-7, MDA-MB 468, MDA-MB-435 WT, and MDA-MB-435 ADR. PgP/pGFP complexes (2 μg pGFP/well) and PgP/siGLO® complexes (0.5 and 1 μg siGLO®/well) were prepared at different N/P ratios ranging from 5/1 to 30/1, respectively. All cells were transfected in media containing 10% FBS and allowed to incubate at 37° C. for 24 hrs; at which time media was replaced. Data acquisition occurred 48 hours post transfection.

Transfection efficiency was measured by flow cytometry using a Millipore easyCyte flow cytometer with guavaCyte software. Cytotoxicity was analyzed by MTT assay same as above described. % Cell Viability=(OD570 (sample)/OD 570 (control))*100 Transfection efficiency of PgP/pGFP polyplexes increased with increasing N/P ratios.

Figure 28A:
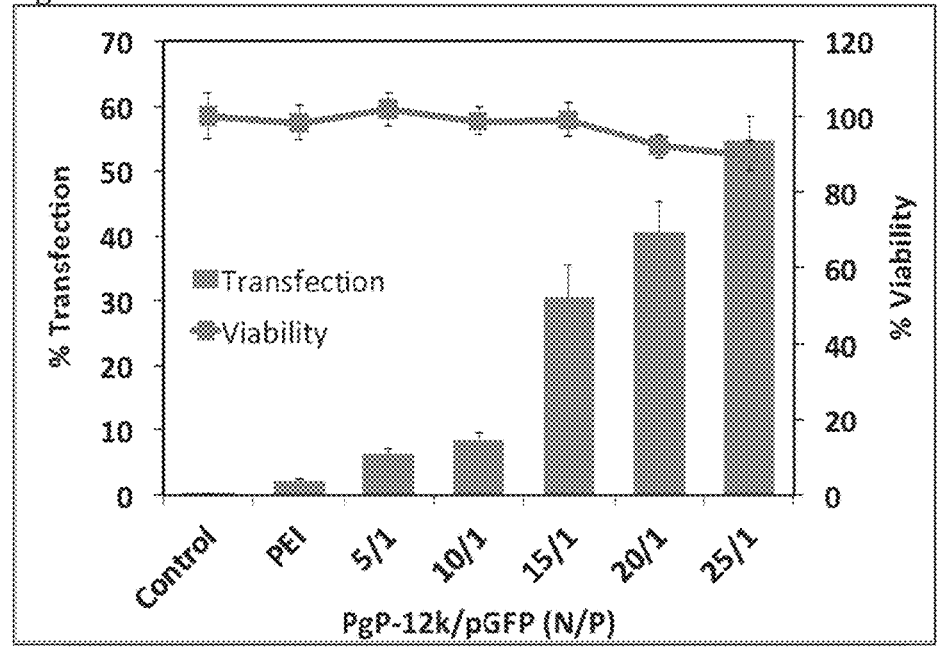
FIG. 28A shows a graph of GFP expression and cell viability of MCF-7 (n=12) after transfection with PgP/pGFP complexes, 10% serum (PEI/pGFP 5/1 used as positive control) (bar=transfection efficiency; line=cell viability).
Figure 28B:
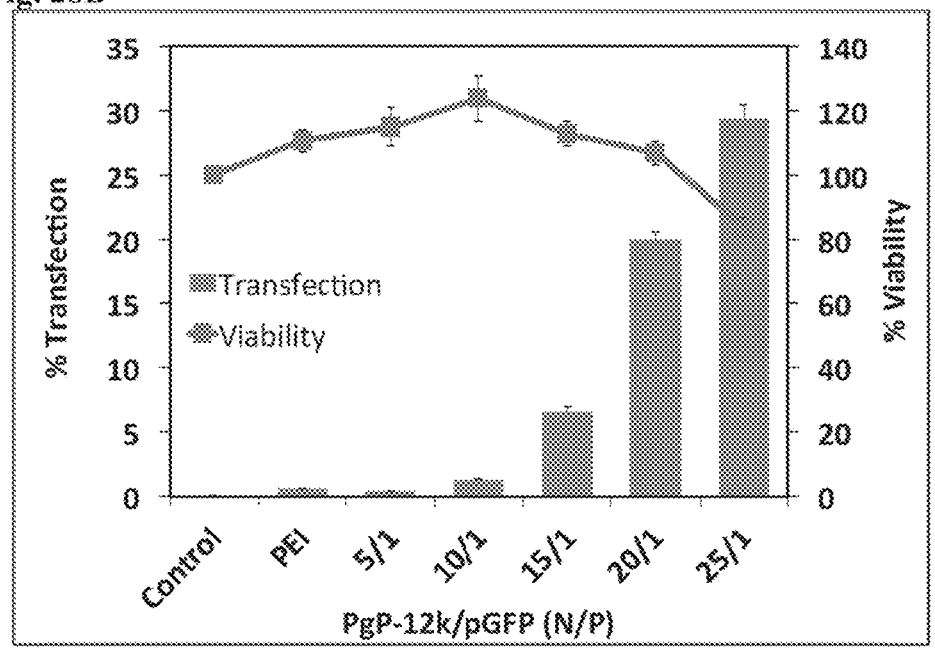
FIG. 28B shows a graph of GFP expression and cell viability of MDA-MD-468 (n=9) after transfection with PgP/pGFP complexes, 10% serum condition (PEI/pGFP 5/1 used as positive control) (bar=transfection efficiency; line=cell viability).

Transfection efficiency of PgP/pGFP polyplex at an N/P ratio of 25/1 was approximately 23.8/77.1 times higher than that of PEI in MCF-7/MDA-MB-468 cells respectively. Complexes at all N/P ratios exhibited low cytotoxicity and maintained cell viabilities above 80% (FIGS. 28A and 28B). Strong visual characteristics of PgP/pGFP transfection at N/P ratios 5/1 through 30/1 were seen in images of transfected MCF-7 cells with PgP/pGFP complexes in 10% serum condition.

Figure 29A:
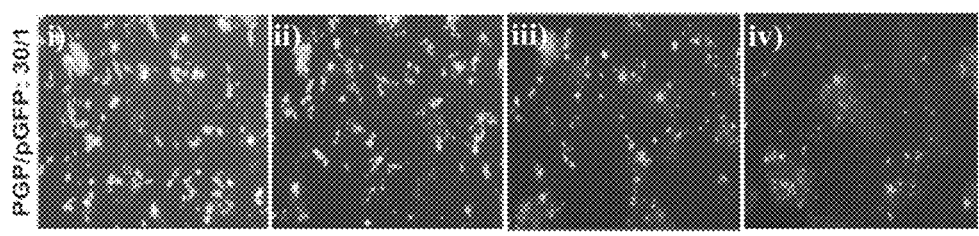
FIG. 29A shows images from a-time course study on GFP expression in MCF-7 cells with PgP/pGFP: 30/1 in 10% serum condition at 4 days (panel i), 8 days (panel ii), 14 days (panel iii), and 20 days (panel iv).
Figure 29B:
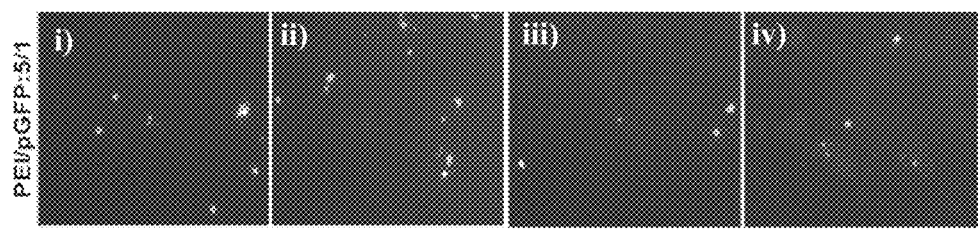
FIG. 29B shows images from a-time course study on GFP expression in MCF-7 cells with PgP/pGFP: 5/1 in 10% serum condition at 4 days (panel i), 8 days (panel ii), 14 days (panel iii), and 20 days (panel iv).

Time-course study of GFP expression in MCF-7 cells after transfection of PgP/pGFP in 10% serum condition were performed and strong GFP expression was maintained for over 20 days for transfected MCF-7 cells using PgP/pGFP at N/P ratio of 30/1 (FIG. 29A, 4 days (panel i), 8 days (panel ii), 14 days (panel iii), and 20 days (panel iv)) compared to PEI/pGFP at N/P ratio of 5/1 (FIG. 29B, 4 days (panel i), 8 days (panel ii), 14 days (panel iii), and 20 days (panel iv)).

Figure 30A:
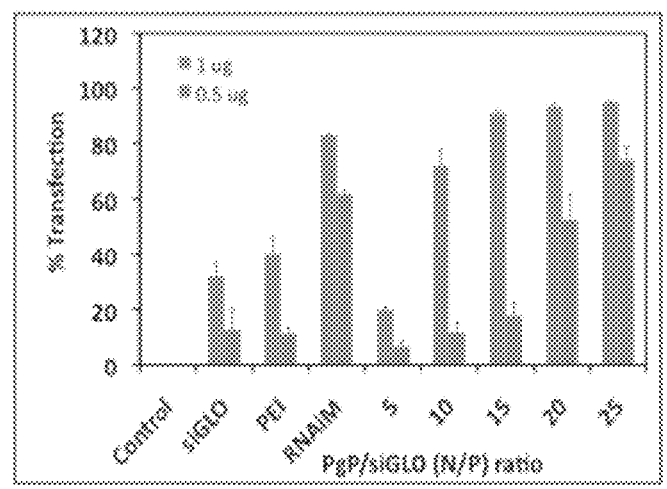
FIG. 30A shows a graph of siGLO transfection after transfection with PgP/siGLO complexes (n=4) MCF-7 cells in 10% serum condition (PEI/pGFP 5/1 used as positive control). Bars for each complex: left=1 µg/mL; right=0.5 µg/mL.
Figure 30B:
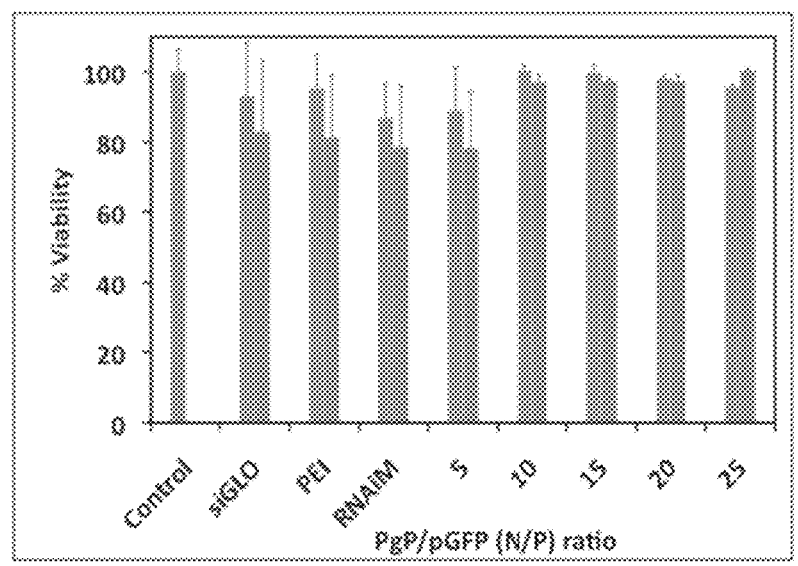
FIG. 30B shows a graph of cell viability after transfection with PgP/siGLO complexes (n=4) MCF-7 cells in 10% serum condition (PEI/pGFP 5/1 used as positive control). Bars for each complex: left=1 g/mL; right=0.5 µg/mL.
Figure 31A:
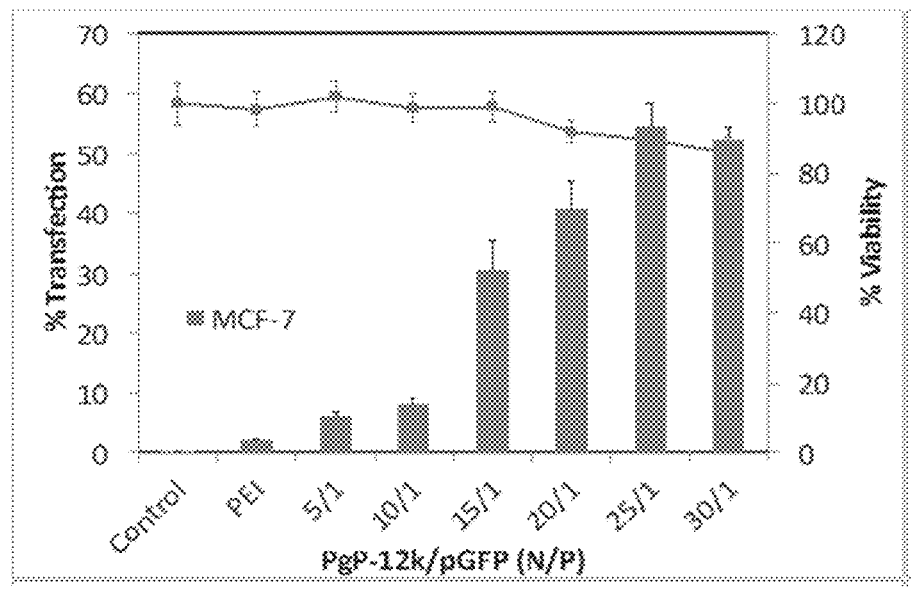
FIG. 31A shows a graph of transfection efficiency and cytotoxicity for PgP-12k/pGFP in MCF-7 cells (bar=transfection efficiency; line=cell viability).
Figure 31B:
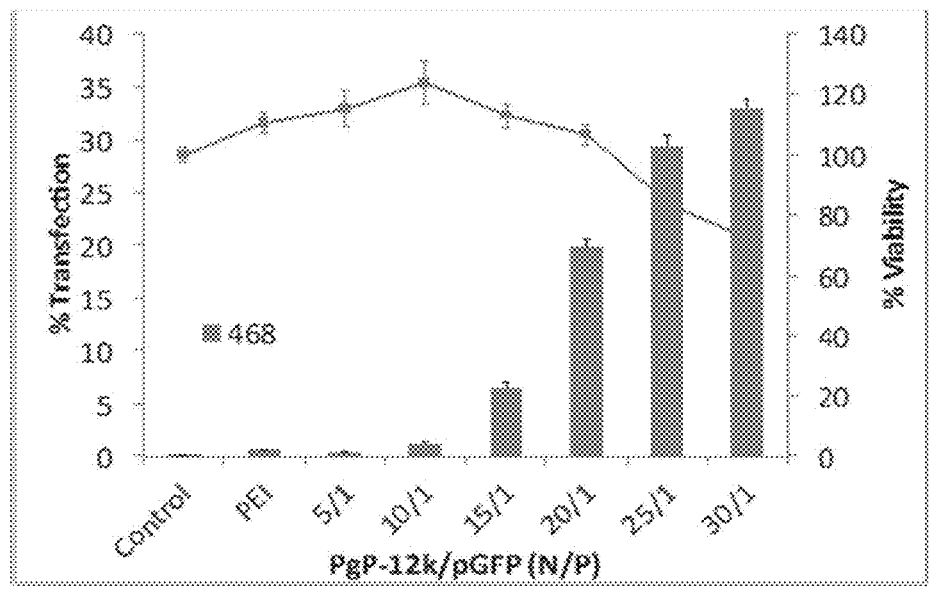
FIG. 31B shows a graph of transfection efficiency and cytotoxicity for PgP-12k/pGFP in 468 cells (bar=transfection efficiency; line=cell viability).
Figure 31C:
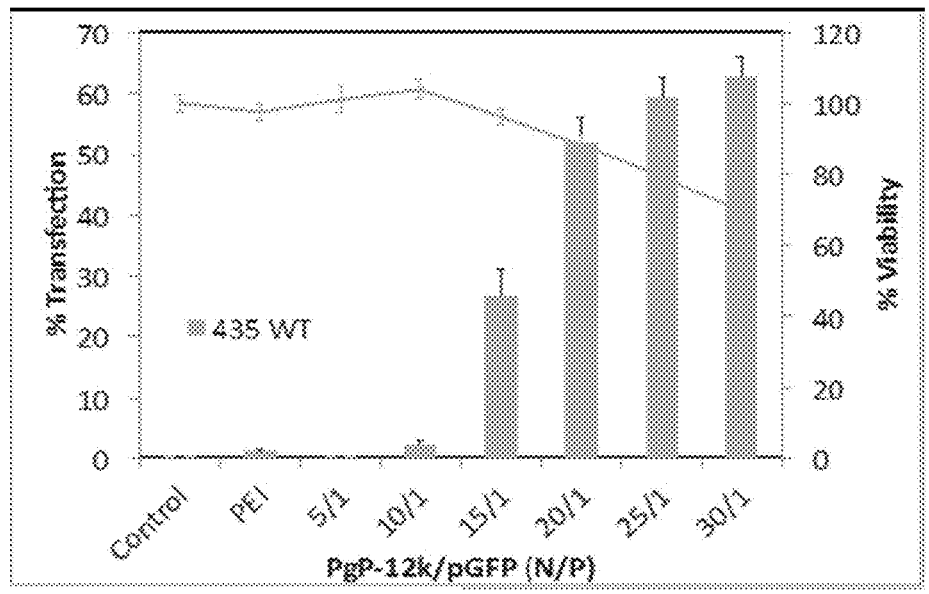
FIG. 31C shows a graph of transfection efficiency and cytotoxicity for PgP-12k/pGFP in 435 WT cells (bar=transfection efficiency; line=cell viability).
Figure 31D:
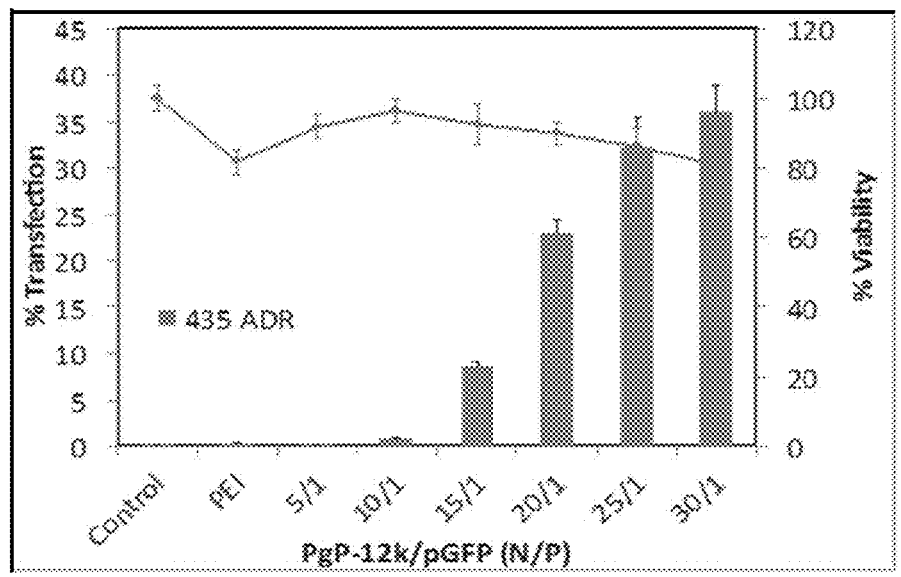
FIG. 31D shows a graph of transfection efficiency and cytotoxicity for PgP-12k/pGFP in 435 ADR cells (bar=transfection efficiency; line=cell viability).

Transfection efficiency of PgP/siGLO® polyplexes increased with an increasing N/P ratio and was higher than that of PEI at N/P ratio of 5/1 without any significant cytotoxicity at all N/P ratios (FIG. 30A). PgP/siGlo complexes at N/P of 10/1 or above showed greater transfection efficiency than PEI/siGLO® complex at N/P ratio of 5/1 without significant cytotoxicity (FIG. 30B). PgP/siGLO® complexes at N/P of 15/1 or above showed similar transfection efficiency with RNAiMax (Invitrogen), which is known as the best commercial transfection reagent for RNAi.

These results demonstrate that the PgP polymeric micelle is a promising carrier for both plasmid DNA and siRNA capable of transfecting breast cancer (MCF-7, MDA-MB-468) cells at high rates in 10% serum condition. It is also demonstrated that transfection duration is long lasting relative to other non-viral methods.

Transfection Conditions for Different MW of PgPs:

The efficiency of 3 different MW of PgPs (PgP-12k, PgP-25k, and PgP-50k) as a gene delivery carrier were assessed by transfections with various PgP/pDNA polyplexes in 10% serum containing media. The particles were prepared as described above in Example 1. bPEI/pDNA at N/P of 5/1 was used as a positive control. Polyplexes were prepared by mixing PgP and pDNA (Beta-gal or GFP, 2 ug/well) in various N/P ratios and then allowing them to incubate for 30 minutes at 37° C. Cells ($9 \times 10^5$ cells/well) were plated in 12-well plates and cultured overnight. The cells were transfected with various PgP/pDNA polyplexes in media containing 10% serum for 24 hrs; then media was removed and replaced by fresh media containing 10% FBS. Cells were then incubated an additional 24 hrs. GFP expression was measured by flow cytometry (Guava easyCyte, Millipore) and the results were expressed as % transfected cells, while beta-gal was assessed according using beta-gal staining kit (Life Technologies, Grand Island, N.Y.). Cytotoxicity was analyzed by MTT assays in parallel experiments as described in Example 1.

Figure 32A:
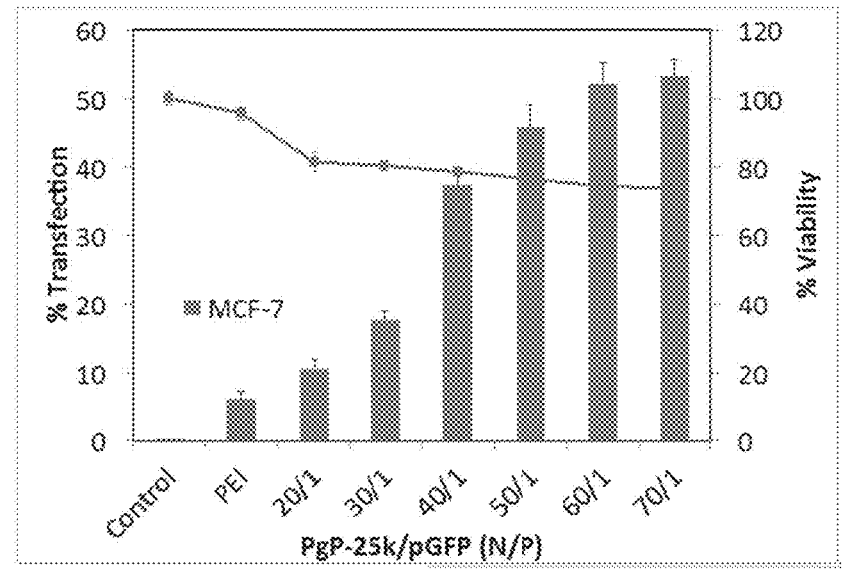
FIG. 32A shows a graph of transfection efficiency and cytotoxicity for PgP-25k/pGFP in MCF-7 cells (bar=transfection efficiency; line=cell viability).
Figure 32B:
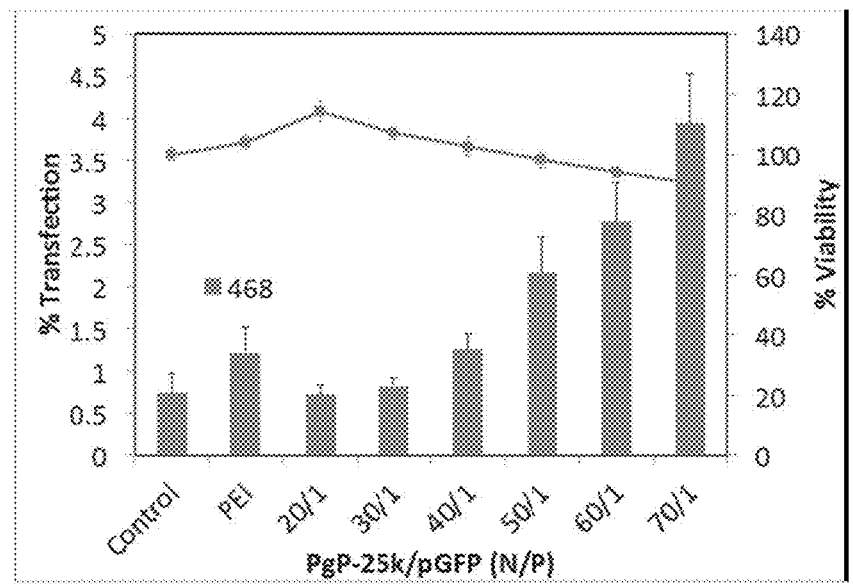
FIG. 32B shows a graph of transfection efficiency and cytotoxicity for PgP-25k/pGFP in 468 cells (bar=transfection efficiency; line=cell viability).
Figure 33A:
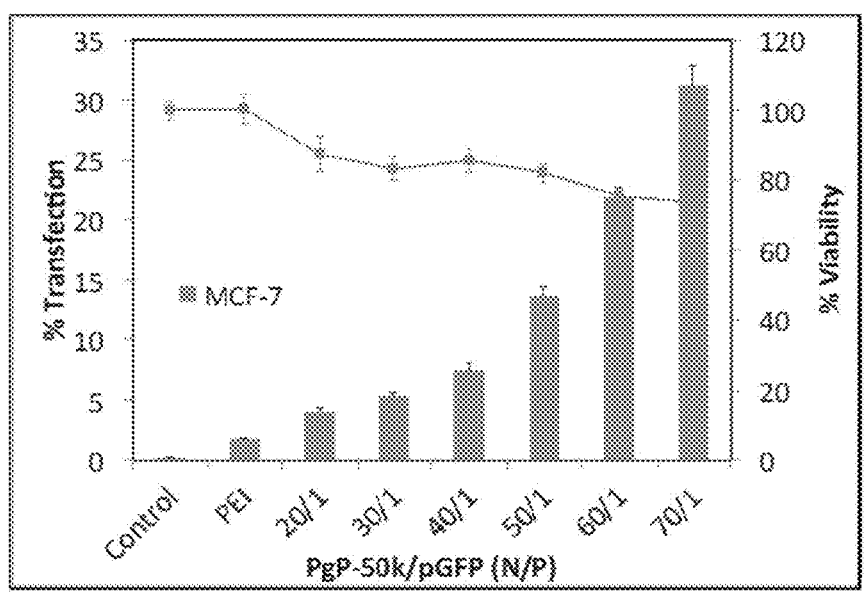
FIG. 33A shows a graph of transfection efficiency and cytotoxicity for PgP-50k/pGFP in MCF-7 cells (bar=transfection efficiency; line=cell viability).
Figure 33B:
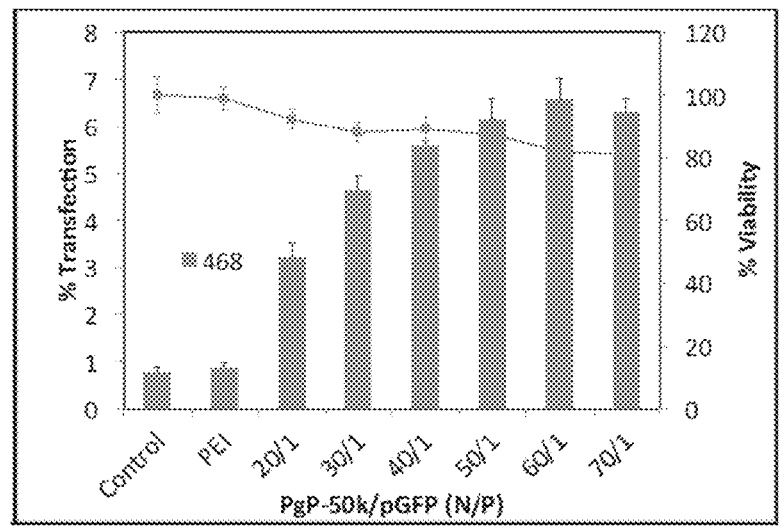
FIG. 33B shows a graph of transfection efficiency and cytotoxicity for PgP-50k/pGFP in 468 cells (bar=transfection efficiency; line=cell viability).

FIGS. 31A-31D illustrate the transfection efficiency and cytotoxicity of PgP-12k/pGFP for various breast cancer cells types. FIGS. 32A and 32B illustrate the transfection efficiency and cytotoxicity of PgP-25k/pGFP for various breast cancer cells types. FIGS. 33A and 33B illustrate the transfection efficiency and cytotoxicity of PgP-50k/pGFP for various breast cancer cells types.

Figure 34:
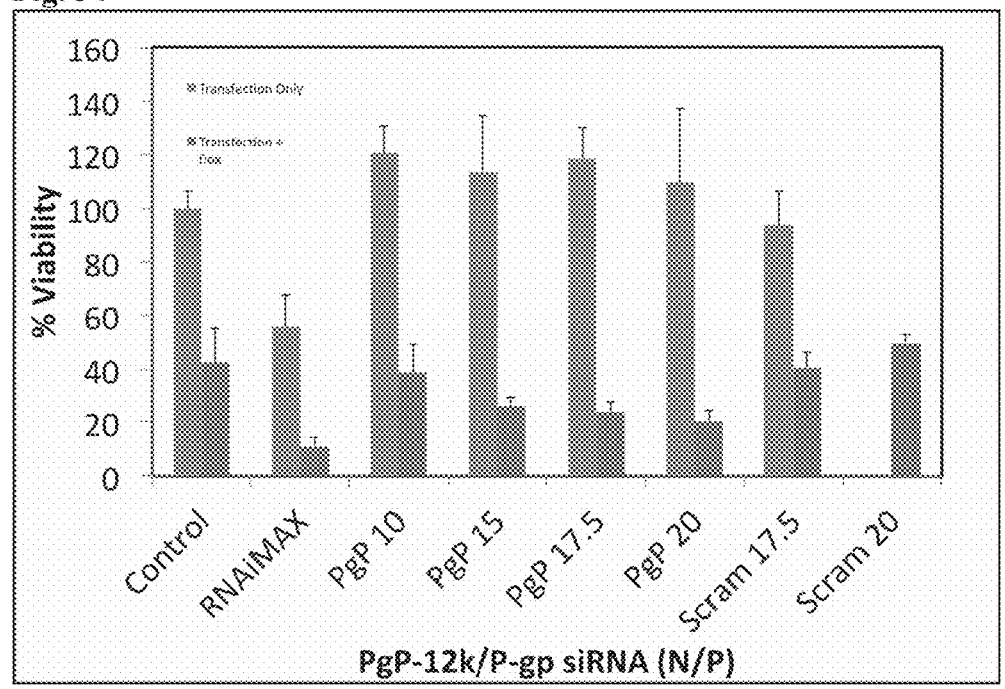
FIG. 34 shows a graph of cell viability for PgP/P-gp siRNA at various N/P ratio in MDA-MB-435 (ADR) cells with/without doxorubicin co-treatment. at Cells were transfected with PgP-12k/P-gp siRNA polyplexes (1 ug siRNA/48 well) prepared at various N/P ratios and 48 hours post transfection media containing 50 ug/mL doxorubicin was added to treatment group. PgP/Scrambled siRNA polyplex was used as negative control (1 ug siRNA/48 well) and RNAiMax/P-gp siRNA polyplex was used as a positive control. Cell viability was assessed 96 hours post transfection. *=P<0.01 vs DOX treated control (for each complex: left bar=transfection only; right bar=transfection+Dox).
Figure 35:
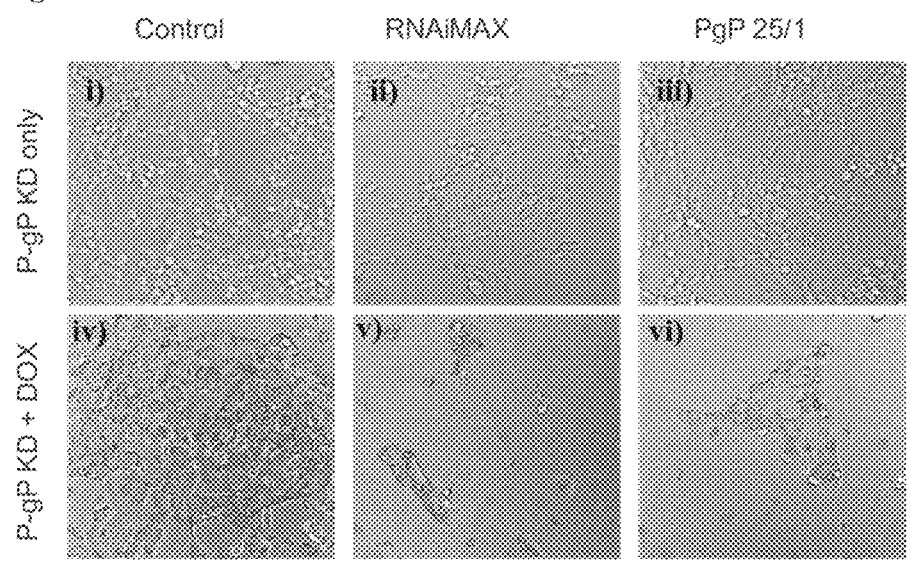
FIG. 35 shows representative images of MDA-MB-435 (ADR) cells after transfection with polyplexes with/without doxorubicin (DXR) co-treatment. Untreated control (panel i), RNAiMAX/P-gpsiRNA (panel ii), PgP-12k/P-gp siRNA (panel iii), control+DXR (panel iv), RNAiMAX/P-gp siRNA.+DXR (panel v) (PgP-12k/P-gp siRNA+DXR (panel vi).

Synergisitc Effect of P-Gp Knockdown on Doxorubicin Efficacy in MDA-MB-ADR Cells MDA-MB-435 ADR cells were transfected with PgP-12k/P-gp siRNA polyplexes at various N/P ratios (1 ug of siRNA or per 48 well) in 10% serum condition with/without doxorubicin co-treatment. Lipofectamine/P-gp siRNA complex was used as a positive control and scrambled siRNA/P-gp siRNA was used as a negative control. Media containing transfection reagent were changed 24 hours post transfection. After two-day post-trasfection, 50 ug/mL Doxorubicin were added in the DXR treated groups and incubated for additional 48 hrs. Cell viability of each group was assessed via MTT assay (FIG. 34). PgP-12k/P-gp siRNA complexes with DXR group showed higher cell death than that with Doxorubicin untreated group while PgP-12k/scrambled siRNA complexes did not, implying target specificity of therapeutic siRNA delivery via PgP-12k while not adding significant cytotoxicity in cells that remain naïve to Doxorubicin. FIG. 35 shows the representative images of MDA-MB-435 (ADR) cells after transfection with polyplexes with/without doxorubicin (DXR) co-treatment. Untreated control (FIG. 35, panel i), RNAiMAX/P-gpsiRNA (FIG. 35, panel ii), PgP-12k/P-gp siRNA (FIG. 35, panel iii), control+ DXR (FIG. 35, panel iv), RNAiMAX/P-gp siRNA.+DXR (FIG. 35, panel v) (PgP-12k/P-gp siRNA+DXR (FIG. 35, panel vi).

Figure 36:
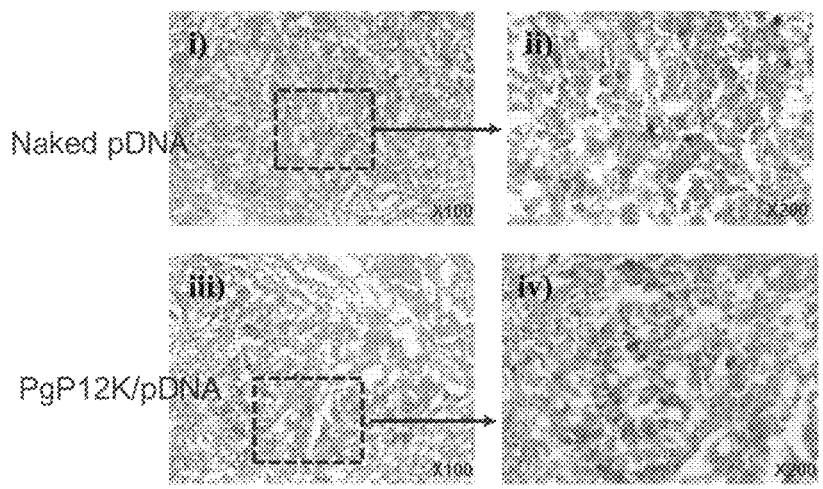
FIG. 36 shows images of β-Gal expressing cells after intratumoral injection of naked pβ-Gal and PgP/pβ-Gal polyplexes in athymic nude mouse breast cancer model in vivo. Naked pβ-Gal injection: panel i (100×) and panel ii (200×, enlargement of highlighted region), PgP/pβ-Gal polyplexes: panel iii (100×) and panel iv (200×, enlargement of highlighted region).

Transfection Efficiency of PgP/pβ-Gal Polyplexes in a Thymic Nude Mouse Breast Cancer Model In Vivo To evaluate the PgP as a therapeutic gene carrier in vivo, mouse breast cancer model was generated. Athymic nude mice (female, 25 gm) were anesthetized with isoflurane gas. An injection containing 2 million MDA-MB-435 ADR cells in 50 ul PBS was injected into four mammary fat pad per mouse. After 1 week post-injection of tumor cell, PgP/pβ-gal complexes (10 μg pβ-gal, 20 μl) were prepared at an N/P ratio of 30/1 and injected into the tumor. bPEI/pβ-gal at an N/P ratio of 5/1 was used as positive control and naked pβ-gal was used as negative control. At 7 days after polyplex injection, animals were anesthetized by isoflurane gas and sacrificed. Tumors were excised and embedded in OCT and sectioned. To evaluate transfection efficiency, sections were stained using a β-Gal staining kit (Life Technologies) to detect β-Gal+ transfected cells. FIG. 36 shows representative images of b-gal expressed cells after intratumoral injection of naked pβ-gal (panel i (100×) and panel ii (400× of window)) and PgP/pβ-gal complexes (panel iii (100×) and panel iv (400× of window)).

The foregoing is illustrative of the present invention, and is not to be construed as limiting thereof. The invention is defined by the following claims, with equivalents of the claims to be included therein.

That which is claimed:

1. A particle comprising poly(lactide-co-glycolide)-graft-polyethylenimine (PLGA-g-PEI (PgP)) and at least one targeting moiety, therapeutic agent, or nucleic acid,
    wherein the particle is a micelle having an interior core and a shell having an exterior surface;
    wherein PLGA-g-PEI forms the micelle, and at least a portion of PLGA of PLGA-g-PEI forms at least a portion of the interior core and at least a portion of PEI of PLGA-g-PEI forms at least a portion of the exterior surface of the shell;
    wherein the PLGA in the PLGA-g-PEI has a molecular weight in a range of about 1 kDalton to about 10 kDaltons and the PLGA has a ratio of lactide to glycolide of 50:50;
    wherein particle has a mole ratio of PLGA to PEI of 1:1 to 6:1 (PLGA:PEI).

2. The particle of claim 1, wherein at least a portion of the interior core is hydrophobic and at least a portion of the exterior surface of the shell is hydrophilic.

3. The particle of claim 1, wherein the particle comprises the at least one targeting moiety and the at least one targeting moiety is covalently conjugated to a portion of the exterior surface of the shell.

4. The particle of claim 3, wherein the at least one targeting moiety comprises at least one tissue-specific targeting moiety.

5. The particle of claim 1, wherein the particle comprises the at least one nucleic acid and the at least one nucleic acid is electrostatically bound to a portion of the exterior surface of the shell.

6. The particle of claim 1, wherein the particle is a nanoparticle having a diameter in a range of about 10 nm to about 200 nm.

7. The particle of claim 1, wherein the particle has an increased transfection efficiency in serum compared to a commercially available non-viral vector.

8. The particle of claim 1, wherein the PEI in the PLGA-g-PEI has a molecular weight in a range of about 2 kDaltons to about 35 kDaltons.

9. The particle of claim 1, wherein the PLGA in the PLGA-g-PEI has a molecular weight in a range of about 1 kDalton to about 5 kDaltons.

10. The particle of claim 1, wherein the PLGA-g-PEI has a molecular weight in a range of about 30 kDaltons to about 125 kDaltons.

11. The particle of claim 1, wherein the PLGA-g-PEI has a hydrophobic lipophilic balance in a range of about 4 to about 16.

12. A method of delivering at least one therapeutic agent and/or at least one nucleic acid to a target, the method comprising:
administering the particle of claim 1 to the target, wherein the particle comprises the at least one therapeutic agent and/or at least one nucleic acid, thereby delivering the at least one therapeutic agent and/or the at least one nucleic acid to the target.

13. The method of claim 12, wherein the at least one targeting moiety is directed to and/or specific for the target.

14. The method of claim 12, wherein the at least one therapeutic agent and the at least one nucleic acid are simultaneously delivered to the target.

15. A method of promoting axonal regeneration and/or treating a central nervous system (CNS) injury in a subject, the method comprising:
administering the particle of claim 1 to the subject, thereby promoting axonal regeneration and/or treating a CNS injury in the subject.

16. A method of treating cancer in a subject, the method comprising:
administering the particle of claim 1 to the subject, thereby treating cancer in the subject.

17. A method of increasing the therapeutic efficiency of at least one therapeutic agent and/or nucleic acid in a subject, the method comprising:
administering the particle of claim 1 to the subject, wherein the particle comprises the at least one therapeutic agent and/or nucleic acid, thereby increasing the therapeutic efficiency of the at least one therapeutic agent and/or nucleic acid in the subject.

18. The particle of claim 1, wherein the particle comprises the at least one therapeutic agent and the interior core of the particle comprises the at least one therapeutic agent.

19. The particle of claim 1, wherein the particle comprises the at least one therapeutic agent and the at least one therapeutic agent is a phosphodiesterase inhibitor.

20. The particle of claim 19, wherein the phosphodiesterase inhibitor is a phosphodiesterase 4 (PDE4) inhibitor.

21. The particle of claim 1, wherein the particle comprises the at least one nucleic acid and the at least one nucleic acid is a small interfering RNA (siRNA).

22. The particle of claim 21, wherein the siRNA is a RhoA siRNA.

23. The particle of claim 1, wherein the particle comprises the at least one therapeutic agent and the at least one therapeutic agent is a phosphodiesterase 4 (PDE4) inhibitor, and wherein the particle comprises at least one nucleic acid and the at least one nucleic acid is a RhoA small interfering RNA (siRNA).

24. The particle of claim 1, wherein the particle comprises the at least one targeting moiety and the at least one targeting moiety is selected from the group consisting of a protein, a cell adhesion molecule, an antibody and/or a fragment thereof, a hormone, a peptide, a nucleic acid, an aptamer, a sugar, a small molecule, and any combination thereof.

25. The particle of claim 24, wherein the at least one targeting moiety comprises a neural cell adhesion molecule.

26. The particle of claim 24, wherein the at least one targeting moiety comprises a L1 cell adhesion molecule.

27. The particle of claim 1, wherein the particle comprises the at least one nucleic acid and the at least one nucleic acid is selected from the group consisting of plasmid DNA (pDNA), small interfering RNA (siRNA), antisense oligonucleotides (ODN), and any combination thereof.

28. The particle of claim 1, wherein the particle comprises the at least one targeting moiety, therapeutic agent, and nucleic acid, and wherein the at least one therapeutic agent is an anticancer drug, the at least one nucleic acid comprises a P-glycoprotein siRNA, and the at least one targeting moiety comprises folic acid.

29. A particle comprising poly(lactide-co-glycolide)-graft-polyethylenimine (PLGA-g-PEI (PgP)) and at least one targeting moiety, therapeutic agent, or nucleic acid,
wherein the particle is a micelle having an interior core and a shell having an exterior surface;
wherein PLGA-g-PEI forms the micelle, and at least a portion of PLGA of PLGA-g-PEI forms at least a portion of the interior core and at least a portion of PEI of PLGA-g-PEI forms at least a portion of the exterior surface of the shell;
wherein the PLGA in the PLGA-g-PEI has a molecular weight in a range of about 20 kDaltons to about 70 kDaltons.

30. The particle of claim 29, wherein the particle comprises at least one therapeutic agent and the at least one therapeutic agent is a phosphodiesterase inhibitor.

31. The particle of claim 30, wherein the phosphodiesterase inhibitor is a phosphodiesterase 4 (PDE4) inhibitor.

32. The particle of claim 29, wherein the particle comprises at least one nucleic acid and the at least one nucleic acid is a small interfering RNA (siRNA).

33. The particle of claim 32, wherein the siRNA is a RhoA siRNA.

34. The particle of claim 29, wherein the particle comprises at least one therapeutic agent and the at least one therapeutic agent is a phosphodiesterase 4 (PDE4) inhibitor, and wherein the particle comprises at least one nucleic acid and the at least one nucleic acid is a RhoA small interfering RNA (siRNA).

35. The particle of claim 29, wherein the particle comprises the at least one targeting moiety and the at least one targeting moiety is selected from the group consisting of a protein, a cell adhesion molecule, an antibody and/or a fragment thereof, a hormone, a peptide, a nucleic acid, an aptamer, a sugar, a small molecule, and any combination thereof.

36. The particle of claim 35, wherein the at least one targeting moiety comprises a neural cell adhesion molecule.

37. The particle of claim 35, wherein the at least one targeting moiety comprises a L1 cell adhesion molecule.

38. The particle of claim 29, wherein the particle comprises the at least one nucleic acid and the at least one nucleic acid is selected from the group consisting of plasmid DNA (pDNA), small interfering RNA (siRNA), antisense oligonucleotides (ODN), and any combination thereof.

39. The particle of claim 29, wherein the particle comprises the at least one targeting moiety, therapeutic agent, and nucleic acid, and wherein the at least one therapeutic agent is an anticancer drug, the at least one nucleic acid comprises a P-glycoprotein siRNA, and the at least one targeting moiety comprises folic acid.

40. A particle comprising poly(lactide-co-glycolide)-graft-polyethylenimine (PLGA-g-PEI (PgP)) and at least one targeting moiety, therapeutic agent, or nucleic acid,
wherein the particle is a micelle having an interior core and a shell having an exterior surface;
wherein PLGA-g-PEI forms the micelle, and at least a portion of PLGA of PLGA-g-PEI forms at least a portion of the interior core and at least a portion of PEI of PLGA-g-PEI forms at least a portion of the exterior surface of the shell;

wherein the PLGA in the PLGA-g-PEI has a molecular weight in a range of about 1 kDalton to about 10 kDaltons and the PLGA has a ratio of lactide to glycolide of 50:50;

wherein particle has a mole ratio of PLGA to PEI of 1:1 to 6:1 (PLGA: PEI); and wherein the particle is stable in an aqueous solution at 25° C. for at least 4 weeks.

41. The particle of claim 40, wherein the particle is stable in the aqueous solution at 4° C. for at least 6 months.

* * * * *

UNITED STATES PATENT AND TRADEMARK OFFICE
CERTIFICATE OF CORRECTION

PATENT NO. : 10,232,050 B1
APPLICATION NO. : 14/966614
DATED : March 19, 2019
INVENTOR(S) : Jeoung Soo Lee Page 1 of 1

It is certified that error appears in the above-identified patent and that said Letters Patent is hereby corrected as shown below:

On the Title Page

Item (56) References Cited, OTHER PUBLICATIONS, Page 2, Column 2, Line 27, 1st Temples cite: Please correct "(2014), Jun. 26, 2017." to read -- (2014). --

In the Specification

Column 3, Line 39: Please correct "1g siGLO" to read -- 1μg siGLO --

Column 3, Line 46: Please correct "mean t SEM" to read -- mean ± SEM --

Column 6, Line 2: Please correct "1g/ml" to read -- 1μg/mL --

Column 7, Line 48: Please correct "+5%" to read -- ±5% --

Column 21, Line 25: Please correct "DH5a" to read -- DH5α --

Column 21, Line 47: Please correct "C-potential" to read -- ζ-potential --

Column 23, Line 59: Please correct "with μl of PgP" to read -- with 10 μl of PgP --

Column 29, Line 47: Please correct "g RhoA" to read -- μg RhoA --

Column 31, Line 33: Please correct "3-3" to read -- β-3 --

Signed and Sealed this
Twenty-seventh Day of August, 2019

Andrei Iancu
*Director of the United States Patent and Trademark Office*